(12) United States Patent
Yoshida et al.

(10) Patent No.: US 11,424,414 B2
(45) Date of Patent: Aug. 23, 2022

(54) ORGANIC ELECTROLUMINESCENT ELEMENT, ELECTRONIC DEVICE, AND COMPOUND

(71) Applicant: IDEMITSU KOSAN CO., LTD., Chiyoda-ku (JP)

(72) Inventors: Kei Yoshida, Sodegaura (JP);
Masatoshi Saito, Sodegaura (JP);
Toshinari Ogiwara, Sodegaura (JP);
Kei Yoshizaki, Sodegaura (JP);
Yuichiro Kawamura, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 357 days.

(21) Appl. No.: 16/497,730

(22) PCT Filed: Mar. 22, 2018

(86) PCT No.: PCT/JP2018/011259
§ 371 (c)(1),
(2) Date: Sep. 25, 2019

(87) PCT Pub. No.: WO2018/180830
PCT Pub. Date: Oct. 4, 2018

(65) Prior Publication Data
US 2021/0098707 A1    Apr. 1, 2021

(30) Foreign Application Priority Data

Mar. 29, 2017 (JP) .............................. JP2017-066380

(51) Int. Cl.
*H01L 51/00* (2006.01)
*C07D 403/14* (2006.01)
(Continued)

(52) U.S. Cl.
CPC ........ *H01L 51/0067* (2013.01); *C07D 403/14* (2013.01); *C09K 11/06* (2013.01);
(Continued)

(58) Field of Classification Search
CPC ............ H01L 51/0067; H01L 51/0072; C07D 403/14; C09K 11/06
See application file for complete search history.

(56) References Cited

U.S. PATENT DOCUMENTS 9,190,623 B2    11/2015  Kwong et al.
2014/0138627 A1    5/2014  Kwong et al.
(Continued)

FOREIGN PATENT DOCUMENTS

JP    2016-111346 A    6/2016
KR    10-2013-0093195 A    8/2013
(Continued)

OTHER PUBLICATIONS

International Search Report dated Jun. 12, 2018 in PCT/JP2018/011259 filed Mar. 22, 2018.
(Continued)

*Primary Examiner* — Anthony Ho
(74) *Attorney, Agent, or Firm* — Oblon, McClelland, Maier & Neustadt, L.L.P.

(57) ABSTRACT

An organic electroluminescence device includes an anode, an emitting layer, and a cathode, in which the emitting layer contains a first compound represented by a formula (1) and a fluorescent second compound. A singlet energy $S_1(M1)$ of the first compound is larger than a singlet energy $S_1(FL)$ of the fluorescent second compound. A is a group represented by a formula (1b).

(Continued)

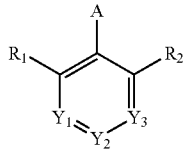

(1)

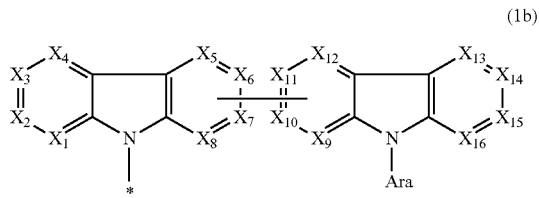

(1b)

34 Claims, 6 Drawing Sheets

(51) Int. Cl.
*C09K 11/06* (2006.01)
*H01L 51/50* (2006.01)
(52) U.S. Cl.
CPC .. *H01L 51/0072* (2013.01); *C09K 2211/1007* (2013.01); *C09K 2211/1018* (2013.01); *H01L 51/5012* (2013.01); *H01L 51/5072* (2013.01)

(56) References Cited

U.S. PATENT DOCUMENTS

2014/0336379 A1 11/2014 Adachi et al.
2016/0163995 A1 6/2016 Kang et al.

FOREIGN PATENT DOCUMENTS

| KR | 10-2015-0135599 | A | 12/2015 |
| KR | 10-2016-0082067 | A | 7/2016 |
| KR | 10-2017-0010715 | A | 2/2017 |
| WO | WO 2012/153780 | A1 | 11/2012 |
| WO | WO 2013/038650 | A1 | 3/2013 |
| WO | WO 2013/081088 | A1 | 6/2013 |
| WO | WO 2015/056965 | A1 | 4/2015 |
| WO | WO 2016/140497 | A2 | 9/2016 |
| WO | WO 2016/181772 | A1 | 11/2016 |

OTHER PUBLICATIONS

Adachi C., "Device Physics of Organic Semiconductors," Kodansha, Apr. 1, 2012, pp. 261-268 (with English Translation).

Uoyama, H. et al., "Highly efficient organic light-emitting diodes from delayed fluorescence," Nature, vol. 492, Dec. 13, 2012, pp. 234-238, 7 pages total.

Lee, S. Y. et al., "High-efficiency organic light-emitting diodes utilizing thermally activated delayed fluorescence from triazine-based donor-acceptor hybrid molecules" Applied Physics Letters, vol. 101, 2012, pp. 093306-1-093306-4 and cover page.

ORGANIC ELECTROLUMINESCENT ELEMENT, ELECTRONIC DEVICE, AND COMPOUND

TECHNICAL FIELD

The present invention relates to an organic electroluminescence device, an electronic device, and a compound.

BACKGROUND ART

When a voltage is applied to an organic electroluminescence device (hereinafter sometimes referred to as an "organic EL device"), holes are injected from an anode into an emitting layer and electrons are injected from a cathode into the emitting layer. The injected holes and electrons are recombined in the emitting layer to form excitons. Here, according to the electron spin statistics theory, singlet excitons and triplet excitons are generated at a ratio of 25%:75%.

A fluorescent organic EL device which uses emission caused by singlet excitons has been applied to a full-color display of a mobile phone, TV and the like. The limited value of an internal quantum efficiency of the organic EL device is believed to be 25%. Accordingly, a material for improving an efficiency of the organic EL device is desired. For instance, Patent Literatures 1 to 3 each disclose a material for an organic EL device.

It is also desired that the organic EL device can emit light more efficiently using triplet excitons in addition to singlet excitons. Based on such a background, a highly efficient fluorescent organic EL device using delayed fluorescence has been proposed and developed.

For instance, TADF (Thermally Activated Delayed Fluorescence) mechanism has been studied. The TADF mechanism utilizes a phenomenon in which inverse intersystem crossing from triplet excitons to singlet excitons is thermally generated by using a material having a small energy gap ($\Delta ST$) between the singlet level and the triplet level. Thermally activated delayed fluorescence is described in, for instance, ADACHI, Chihaya, ed. "Yuki Hando-tai no Debaisu Bussei (Device Physics of Organic Semiconductors)", Kodansha Ltd., published on Apr. 1, 2012, pp. 261-262.

Patent Literatures 1 to 3 fail to disclose an organic EL device emitting light by the TADF mechanism.

CITATION LIST

Patent Literature(S)

Patent Literature 1: Korean Patent Publication No. 10-2016-0082067
Patent Literature 2: International Publication No. WO2015/056965
Patent Literature 3: Korean Patent Publication No. 10-2013-0093195

SUMMARY OF THE INVENTION

Problems to be Solved by the Invention

In order to improve a performance of a full color display using an organic EL device, a compound and an organic EL device which are capable of improving a luminous efficiency have been desired.

An object of the invention is to provide a compound and an organic electroluminescence device which are capable of improving a luminous efficiency, and an electronic device including the organic electroluminescence device.

Means for Solving the Problems

According to an aspect of the invention, an organic electroluminescence device includes an anode, an emitting layer, and a cathode, in which the emitting layer includes a first compound represented by a formula (1) and a fluorescent compound, and a singlet energy $S_1(M1)$ of the first compound is larger than a singlet energy $S_1(FL)$ of the fluorescent compound.

[Formula 1]

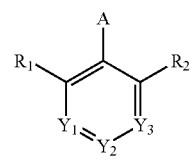

(1)

In the formula (1): $Y_1$, $Y_2$ and $Y_3$ each independently represent C—Ra or a nitrogen atom; at least one of $Y_1$, $Y_2$ and $Y_3$ is a nitrogen atom; $R_1$, $R_2$ and Ra each independently represent a hydrogen atom or a substituent; $R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; a plurality of Ra are mutually the same or different; at least one of $R_1$ and $R_2$ is the substituent; and A is a group represented by one of the following formulae (1a), (1b) and (1c).

[Formula 2]

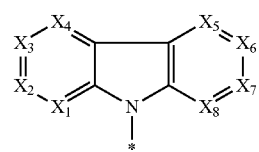

(1a)

[Formula 3]

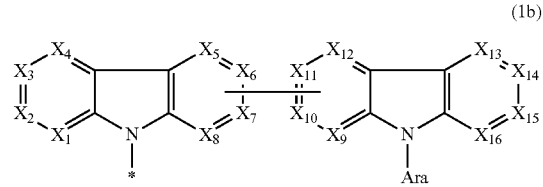

(1b)

[Formula 4]

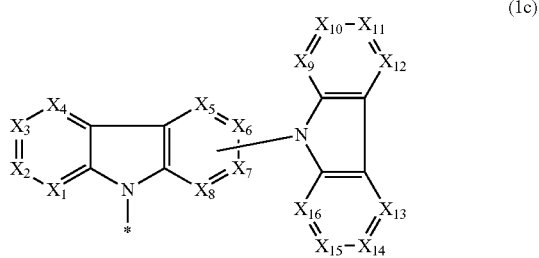

(1c)

In the formulae (1a), (1b) and (1c): $X_1$ to $X_{16}$ each independently represent C—Rb or a nitrogen atom; in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$; in the formula (1c), at least one of $X_5$ to $X_8$ is a carbon atom bonded to a nitrogen atom in a five-membered ring of a nitrogen-containing fused ring including $X_8$ to $X_{16}$.

Rb each independently represents a hydrogen atom or a substituent.

Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of Rb are mutually the same or different.

When a plurality of ones of $X_1$ to $X_8$ are C—Rb and Rb is a substituent, a plurality of Rb are bonded to each other to form a ring, or are not bonded.

When a plurality of ones of $X_9$ to $X_{16}$ are C—Rb and Rb is a substituent, a plurality of Rb are bonded to each other to form a ring, or are not bonded.

Ara is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

* represents a bonding position with a carbon atom in a cyclic structure of the first compound represented by the formula (1).

According to another aspect of the invention, an organic electroluminescence device includes an anode, an emitting layer, and a cathode, in which the emitting layer includes a first compound represented by a formula (1) and a second compound, and a singlet energy $S_1(M2)$ of the second compound is larger than a singlet energy $S_1(M1)$ of the first compound.

The above aspect of the invention provides a compound represented by a formula (11) below.

[Formula 5]

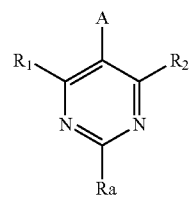

(11)

In the formula (11): Ra represents a hydrogen atom or a substituent; $R_1$ and $R_2$ are each independently a substituent; $R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and A is a group represented by one of the following formulae (1a), (1b) and (1c).

[Formula 6]

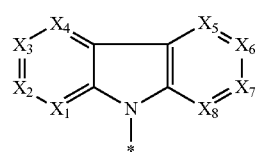

(1a)

[Formula 7]

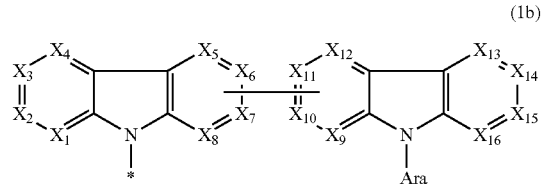

(1b)

-continued

[Formula 8]

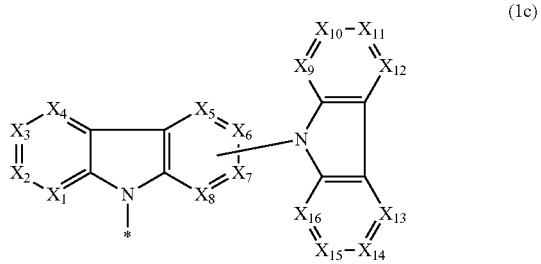

(1c)

In the formulae (1a), (1b) and (1c): $X_1$ to $X_{16}$ each independently represent C—Rb or a nitrogen atom.

In the formula (1 b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$.

In the formula (1c), at least one of $X_5$ to $X_8$ is a carbon atom bonded to a nitrogen atom in a five-membered ring of a nitrogen-containing fused ring including $X_9$ to $X_{16}$.

Rb each independently represents a hydrogen atom or a substituent.

Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of Rb are mutually the same or different.

When a plurality of ones of $X_1$ to $X_8$ are C—Rb and Rb is a substituent, a plurality of Rb are bonded to each other to form a ring, or are not bonded.

When a plurality of ones of $X_9$ to $X_{16}$ are C—Rb and Rb is a substituent, a plurality of Rb are bonded to each other to form a ring, or are not bonded.

Ara is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group.

* represents a bonding position with a carbon atom in a cyclic structure of the compound represented by the formula (11).

Still another aspect of the invention provides an electronic device including the organic electroluminescence device according to the above aspect of the invention.

According to the above aspects of the invention, a compound and an organic electroluminescence device which are capable of improving a luminous efficiency and an electronic device including the organic electroluminescence device can be provided.

DESCRIPTION OF EMBODIMENT(S)

Figure 1:
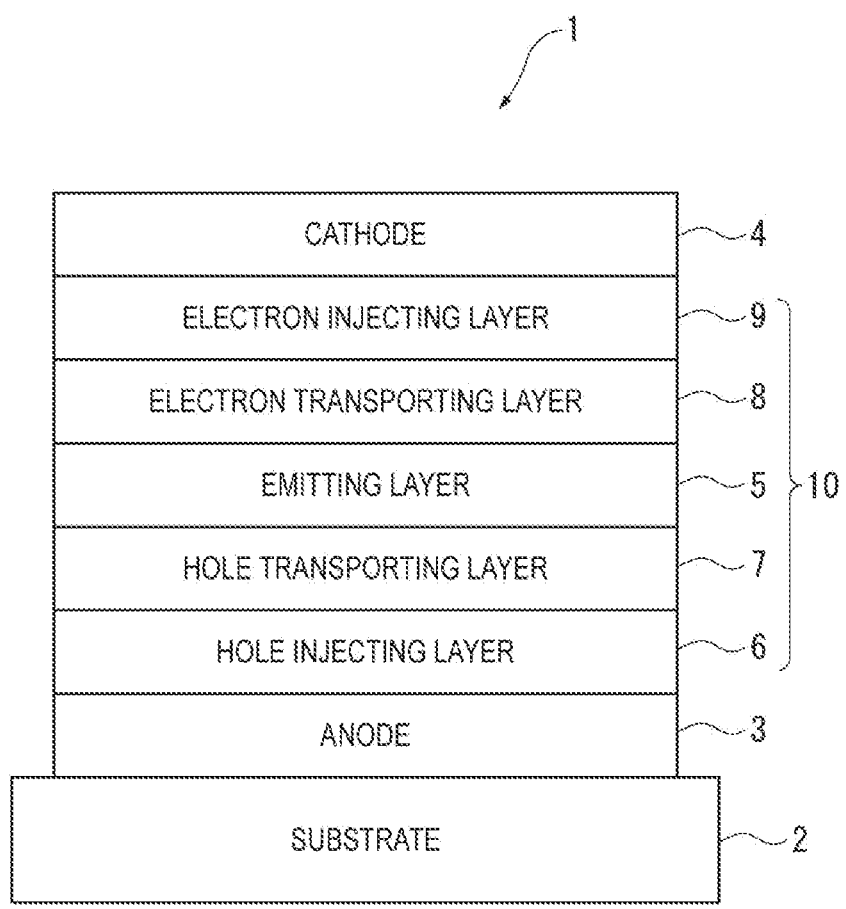
FIG. 1 schematically shows an exemplary arrangement of an organic electroluminescence device according to a first exemplary embodiment of the invention.

The inventors have found that use of a compound represented by a formula (1) in organic EL devices in exemplary embodiments described below to improves an efficiency of the organic EL devices to be.

First Exemplary Embodiment

Organic EL Device
Arrangement(s) of Organic EL Device

Arrangement(s) of an organic EL device according to an exemplary embodiment will be described below.

The organic EL device in the exemplary embodiment includes a pair of electrodes and an organic layer between the pair of electrodes. The organic layer includes at least one layer formed of an organic compound. Alternatively, the organic layer includes a plurality of layers each formed of an organic compound. The organic layer may further include an inorganic compound. In the organic EL device in the exemplary embodiment, at least one layer of the organic layer(s) is the emitting layer. Specifically, for instance, the organic layer may consist of a single emitting layer, or may include layers usable in a typical organic EL device. The layers usable in a typical organic EL device are not limited to particular ones, but, for instance, at least one layer selected from the group consisting of a hole injecting layer, a hole transporting layer, an electron injecting layer, an electron transporting layer and a blocking layer.

Typical device arrangements of the organic EL device include the following arrangements (a) to (f) and the like:
(a) anode/emitting layer/cathode;
(b) anode/hole injecting-transporting layer/emitting layer/cathode;

(c) anode/emitting layer/electron injecting-transporting layer/cathode;

(d) anode/hole injecting-transporting layer/emitting layer/electron injecting-transporting layer/cathode;

(e) anode/hole injecting-transporting layer/emitting layer/blocking layer/electron injecting-transporting layer/cathode; and (f) anode/hole injecting-transporting layer/blocking layer/emitting layer/blocking layer/electron injecting-transporting layer/cathode.

The arrangement (d) is preferably used among the above arrangements. However, the arrangement according to the invention is not limited to the above arrangements. The "emitting layer" refers to an organic layer having an emitting function. The term "hole injecting-transporting layer" means at least one of a hole injecting layer and a hole transporting layer. The term "electron injecting-transporting layer" means at least one of an electron injecting layer and an electron transporting layer. When the organic EL device includes the hole injecting layer and the hole transporting layer, the hole injecting layer is preferably provided between the hole transporting layer and the anode. When the organic EL device includes the electron injecting layer and the electron transporting layer, the electron injecting layer is preferably provided between the electron transporting layer and the cathode. The hole injecting layer, the hole transporting layer, the electron transporting layer and the electron injecting layer may each consist of a single layer or a plurality of layers.

FIG. 1 schematically shows an arrangement of an exemplary organic EL device according to the exemplary embodiment.

An organic EL device 1 includes a light-transmissive substrate 2, an anode 3, a cathode 4 and an organic layer 10 disposed between the anode 3 and the cathode 4. The organic layer 10 includes a hole injecting layer 6, a hole transporting layer 7, an emitting layer 5, an electron transporting layer 8, and an electron injecting layer 9. In the organic layer 10, the hole injecting layer 6, the hole transporting layer 7, the emitting layer 5, the electron transporting layer 8, and the electron injecting layer 9 are laminated on the anode 3 in this sequence.

Emitting Layer

The emitting layer 5 of the organic EL device 1 contains a first compound and a fluorescent compound.

The first compound is also preferably a host material (occasionally referred to as a matrix material). The fluorescent compound is also preferably a dopant material (occasionally referred to as a guest material, emitter or luminescent material).

The emitting layer 5 may contain a metal complex, however, preferably does not contain a heavy metal complex.

The emitting layer 5 preferably does not contain a phosphorescent metal complex.

First Compound

In the organic EL device of this exemplary embodiment, a compound represented by a formula (1) below is used as the first compound.

[Formula 9]

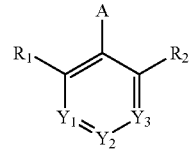

(1)

In the formula (1), $Y_1$, $Y_2$ and $Y_3$ each independently represent C—Ra or a nitrogen atom.

At least one of $Y_1$, $Y_2$ and $Y_3$ is a nitrogen atom.

$R_1$, $R_2$ and Ra each independently represent a hydrogen atom or a substituent.

$R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of Ra are mutually the same or different.

At least one of $R_1$ and $R_2$ is the substituent.

A is a group represented by one of the following formulae (1a), (1b) and (1c).

[Formula 10]

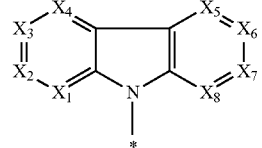

(1a)

[Formula 11]

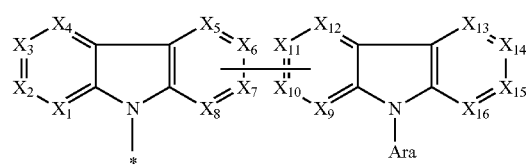

(1b)

[Formula 12]

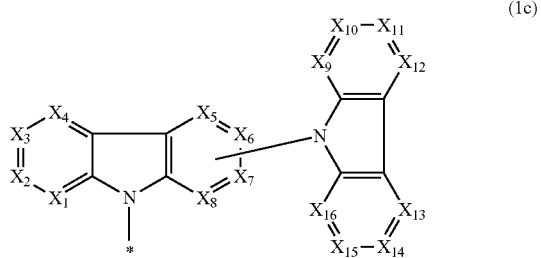

(1c)

[Formula 13]

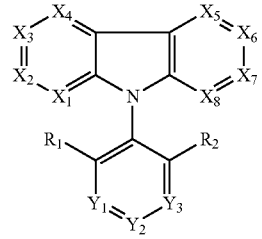

(12)

In the formulae (1a), (1b) and (1c), $X_1$ to $X_{16}$ each independently represent C—Rb or a nitrogen atom.

In the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$.

In the formula (1c), at least one of $X_5$ to $X_8$ is a carbon atom bonded to a nitrogen atom in a five-membered ring of a nitrogen-containing fused ring including $X_9$ to $X_{16}$.

Rb each independently represents a hydrogen atom or a substituent.

Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

A plurality of Rb are mutually the same or different.

When a plurality of ones of $X_1$ to $X_8$ are C—Rb and Rb is a substituent, a plurality of Rb are bonded to each other to form a ring, or are not bonded.

When a plurality of ones of $X_9$ to $X_{16}$ are C—Rb and Rb is a substituent, a plurality of Rb are bonded to each other to form a ring, or are not bonded.

Ara is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

\* represents a bonding position with a carbon atom in the cyclic structure represented by the formula (1).

In the formula (1), at least one of $R_1$ and $R_2$ is a substituent, which means that $R_1$ and $R_2$ are not hydrogen atoms at the same time.

When A is the group represented by the formula (1a), the compound of the exemplary embodiment is represented by a formula (12) below.

In the formula (12): $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_1$ to $X_8$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded.

When A is the group represented by the formula (1b), the first compound of the exemplary embodiment is represented by a formula (13) below.

[Formula 14]

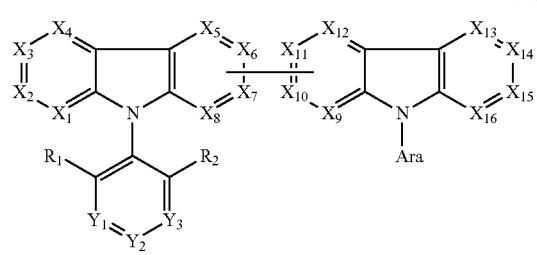

(13)

In the formula (13), $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_1$ to $X_{16}$ each independently represent C—Rb or a nitrogen atom.

In the formula (13), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$.

In the formula (13), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. Ara represents the same as the above-described Ara as the substituent.

When A is the group represented by the formula (1c), the first compound of the exemplary embodiment is represented by a formula (14) below.

[Formula 15]

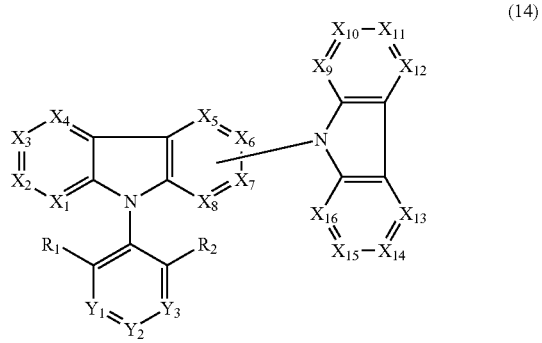

(14)

In the formula (14), $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_1$ to $X_1$ each independently represent C—Rb or a nitrogen atom.

In the formula (14), at least one of $X_5$ to $X_8$ is a carbon atom bonded to a nitrogen atom in a five-membered ring of a nitrogen-containing fused ring including $X_9$ to $X_{16}$.

In the formula (14), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded.

In the first compound according to the exemplary embodiment, A is preferably the group represented by the formula (1b) or (1c), more preferably the group represented by the formula (1b). In other words, the first compound of the exemplary embodiment is preferably the compound represented by the formula (13) or (14), more preferably the compound represented by the formula (13).

In the first compound in the exemplary embodiment, when A is the group represented by the formula (1b) and Rb is a hydrogen atom or a substituent, Rb as the substituent is preferably selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

At this time, Rb as the substituent is more preferably selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

In the first compound in the exemplary embodiment, when A is the group represented by the formula (1b) and Rb is a hydrogen atom or a substituent, Rb as the substituent preferably does not contain a substituted or unsubstituted carbazolyl group, more preferably does not contain a substituted or unsubstituted heteroaryl group having 5 to 30 ring atoms.

In the first compound according to the exemplary embodiment, it is preferable that A is the group represented by the formula (1b), $X_1$, $X_2$, $X_3$, and $X_4$ are C—Rb, and Rb is a hydrogen atom.

When A is the group represented by the formula (1b), $X_1$, $X_2$, $X_3$, and $X_4$ are C—Rb, and Rb is a hydrogen atom, the first compound of the exemplary embodiment is represented by a formula (13a) below.

[Formula 16]

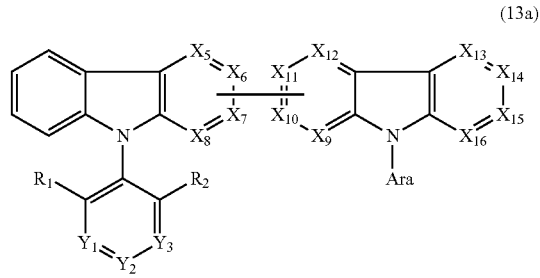

(13a)

In the formula (13a), $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_5$ to $X_{16}$ each independently represent C—Rb or a nitrogen atom.

In the formula (13a), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$.

In the formula (13a), Rb each independently represents a hydrogen atom or a substituent. Rb as the substituent represents the same as the above-described Rb as the substituent. A plurality of Rb are mutually the same or different. When a plurality of ones of $X_5$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. Ara represents the same as the above-described Ara as the substituent.

The first compound of the exemplary embodiment is preferably represented by a formula (10A).

[Formula 17]

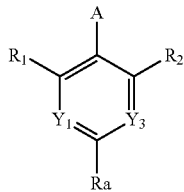

(10A)

In the formula (10A), $Y_1$ and $Y_3$ each independently represent C—Ra or a nitrogen atom. At least one of $Y_1$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. A is the group represented by one of the formulae (1a), (1b) and (1c).

In the first compound of the exemplary embodiment, it is preferable that two of $Y_1$, $Y_2$ and $Y_3$ are nitrogen atoms and the remaining one of $Y_1$, $Y_2$ and $Y_3$ is C—Ra.

In the first compound of the exemplary embodiment, it is preferable that $Y_1$ and $Y_3$ are nitrogen atoms and $Y_2$ is C—Ra.

The first compound of the exemplary embodiment is preferably represented by a formula (10B).

[Formula 18]

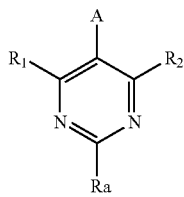

(10B)

In the formula (10B), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. A is the group represented by one of the formulae (1a), (1b) and (1c).

In the formula (12), when $Y_1$ and $Y_3$ are nitrogen atoms and $Y_2$ is C—Ra, the first compound of the exemplary embodiment is represented by a formula (12a).

[Formula 19]

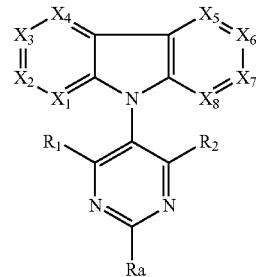

(12a)

In the formula (12a), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_8$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded.

In the formula (13), when $Y_1$ and $Y_3$ are nitrogen atoms and $Y_2$ is C—Ra, the first compound of the exemplary embodiment is represented by a formula (13b).

[Formula 20]

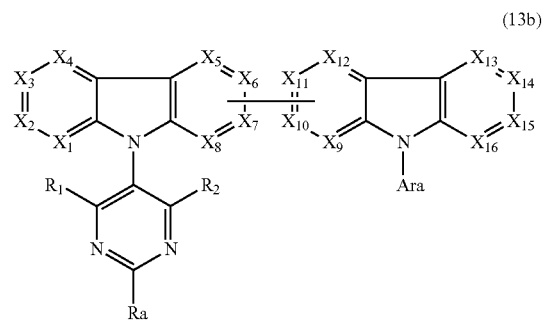

(13b)

In the formula (13b), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_1$ each independently represent C—Rb or a nitrogen atom.

In the formula (13b), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$.

In the formula (13b), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. Ara represents the same as the above-described Ara as the substituent.

The first compound of the exemplary embodiment is preferably represented by a formula (15a).

[Formula 21]

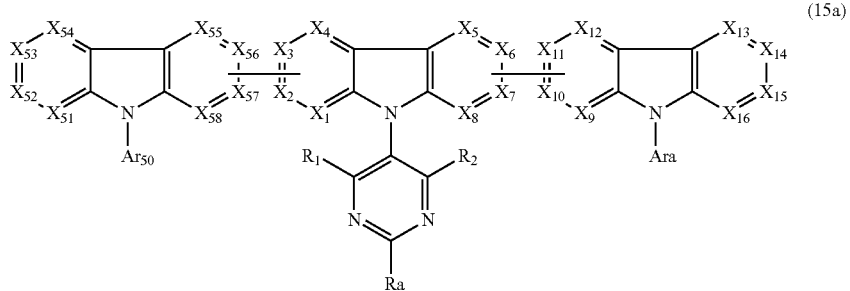

(15a)

In the formula (15a), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_1$ and $X_{51}$ to $X_{58}$ each independently represent C—Rb or a nitrogen atom.

In the formula (15a), at least one of $Y_5$ to $Y_8$ is a carbon atom bonded to one of $Y_9$ to $Y_{12}$, at least one of $Y_9$ to $Y_{12}$ is a carbon atom bonded to one of $Y_5$ to $Y_8$, at least one of $X_1$ to $X_4$ is a carbon atom bonded to one of $X_{55}$ to $X_5$, and at least one of $X_{55}$ to $X_5$ is a carbon atom bonded to one of $X_1$ to $X_4$.

In the formula (15a), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. When a plurality of ones of $X_{51}$ to $X_{58}$ are C—Rb and Rb is a substituent, a plurality of Rb are bonded to each other to form a ring, or are not bonded. Ara and $Ar_{50}$ each independently represent the same as the above-described Ara as the substituent.

In the formula (14), when $Y_1$ and $Y_3$ are nitrogen atoms and $Y_2$ is C—Ra, the first compound of the exemplary embodiment is represented by a formula (14a).

[Formula 22]

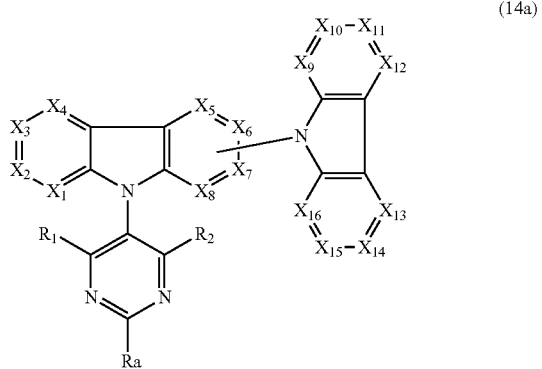

(14a)

In the formula (14a), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_1$ each independently represent C—Rb or a nitrogen atom.

In the formula (14a), at least one of $X_5$ to $X_8$ is a carbon atom bonded to a nitrogen atom in a five-membered ring of a nitrogen-containing fused ring including $X_9$ to $X_{16}$.

In the formula (14a), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded.

The first compound of the exemplary embodiment is preferably represented by a formula (16a).

[Formula 23]

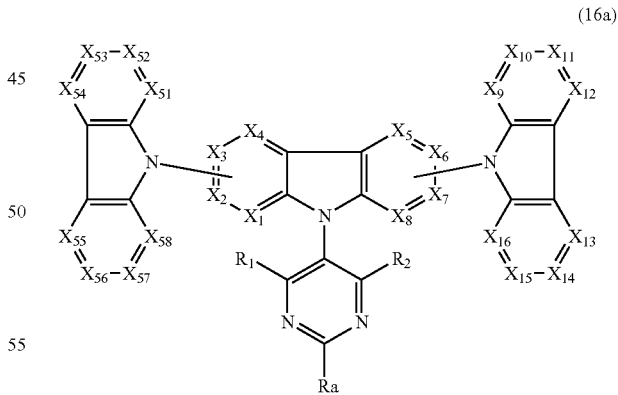

(16a)

In the formula (16a), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_{16}$ and $X_{51}$ to $X_{58}$ each independently represent C—Rb or a nitrogen atom.

In the formula (16a), at least one of $X_1$ to $X_4$ is a carbon atom bonded to a nitrogen atom in a five-membered ring of a nitrogen-containing fused ring including $X_{51}$ to $X_{58}$. At least one of $X_5$ to $X_8$ is a carbon atom bonded to a nitrogen atom in a five-membered ring of a nitrogen-containing fused ring including $X_9$ to $X_{16}$.

In the formula (16a), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. When a plurality of ones of $X_{51}$ to $X_{58}$ are C—Rb and Rb is a substituent, a plurality of Rb are bonded to each other to form a ring, or are not bonded.

In the formulae (13), (13a) and (13b), it is preferable that $X_6$ is a carbon atom to be bonded to $X_{11}$ and $X_{11}$ is a carbon atom to be bonded to $X_6$. In the formula (13), when $X_6$ is a carbon atom bonded to $X_{11}$ and $X_{11}$ is a carbon atom bonded to $X_6$, the first compound of the exemplary embodiment is represented by a formula (13c).

[Formula 24]

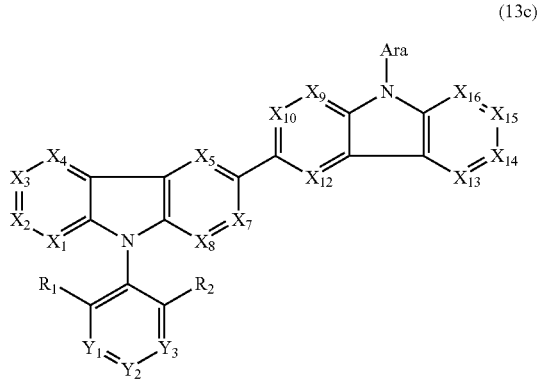

(13c)

In the formula (13c), $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_1$ to $X_5$, $X_7$ to $X_{10}$ and $X_{12}$ to $X_{16}$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_5$, $X_7$ and $X_8$ are C—Rb and Rb is a substituent, a plurality of Rb are bonded to each other to form a ring, or are not bonded. When a plurality of ones of $X_9$, $X_{10}$, and $X_{12}$ to $X_{16}$ are C—Rb and Rb is a substituent, a plurality of Rb are bonded to each other to form a ring, or are not bonded. Ara represents the same as the above-described Ara as the substituent.

In the formula (13c), when $Y_1$ and $Y_3$ are nitrogen atoms and $Y_2$ is C—Ra, the first compound of the exemplary embodiment is represented by a formula (13c).

[Formula 25]

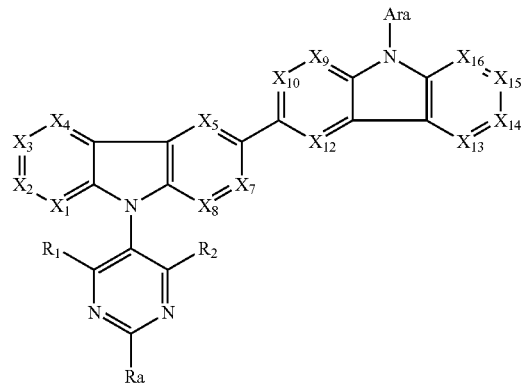

(13e)

In the formula (13e), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_5$, $X_7$ to $X_{10}$ and $X_{12}$ to $X_{16}$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_5$, $X_7$ and $X_8$ are C—Rb and Rb is a substituent, a plurality of Rb are bonded to each other to form a ring, or are not bonded. When a plurality of ones of $X_9$, $X_{10}$, and $X_{12}$ to $X_{16}$ are C—Rb and Rb is a substituent, a plurality of Rb are bonded to each other to form a ring, or are not bonded. Ara represents the same as the above-described Ara as the substituent.

In the formulae (13), (13a) and (13b), it is preferable that $X_5$ is a carbon atom to be bonded to $X_{11}$ and $X_{11}$ is a carbon atom to be bonded to $X_5$. In the formula (13), when $X_5$ is a carbon atom bonded to $X_{11}$ and $X_{11}$ is a carbon atom bonded to $X_5$, the first compound of the exemplary embodiment is represented by a formula (13d).

[Formula 26]

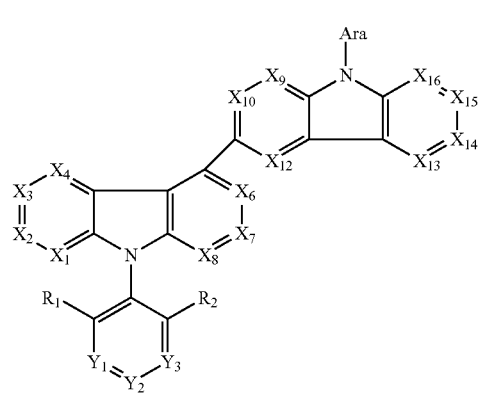

(13d)

In the formula (13d), $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_1$ to $X_4$, $X_6$ to $X_{10}$ and $X_{12}$ to $X_{16}$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_4$, $X_6$ to $X_8$ are C—Rb and Rb is a substituent, a plurality of Rb are bonded to each other to form a ring, or are not bonded. When a plurality of ones of $X_9$, $X_{10}$, and $X_{12}$ to $X_{16}$ are C—Rb and Rb is a substituent, a plurality of Rb are bonded to each other to form a ring, or are not bonded. Ara represents the same as the above-described Ara as the substituent.

In the formula (13d), when $Y_1$ and $Y_3$ are nitrogen atoms and $Y_2$ is C—Ra, the first compound of the exemplary embodiment is represented by a formula (13f).

[Formula 27]

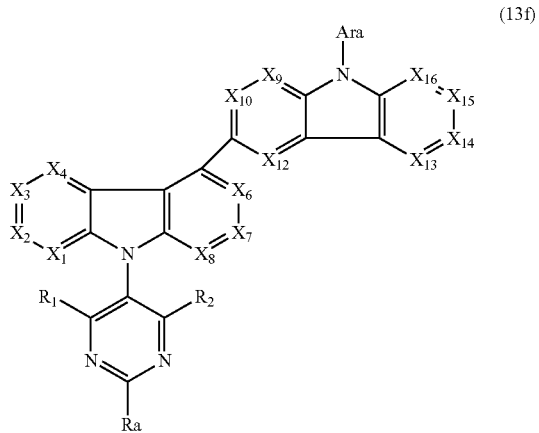

(13f)

In the formula (13f), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_4$, $X_6$ to $X_1$ and $X_{12}$ to $X_{16}$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_4$, $X_6$ to $X_8$ are C—Rb and Rb is a substituent, a plurality of Rb are bonded to each other to form a ring, or are not bonded. When a plurality of ones of $X_9$, $X_{10}$, and $X_{12}$ to $X_{16}$ are C—Rb and Rb is a substituent, a plurality of Rb are bonded to each other to form a ring, or are not bonded. Ara represents the same as the above-described Ara as the substituent.

In the formulae (14) and (14a), $X_6$ is preferably a carbon atom bonded to a nitrogen atom in a five-membered ring of a nitrogen-containing fused ring including $X_9$ to $X_{16}$.

In the formula (14), when $X_6$ is a carbon atom bonded to a nitrogen atom in a five-membered ring of a nitrogen-containing fused ring including $X_9$ to $X_{16}$, the first compound of the exemplary embodiment is represented by a formula (14b).

[Formula 28]

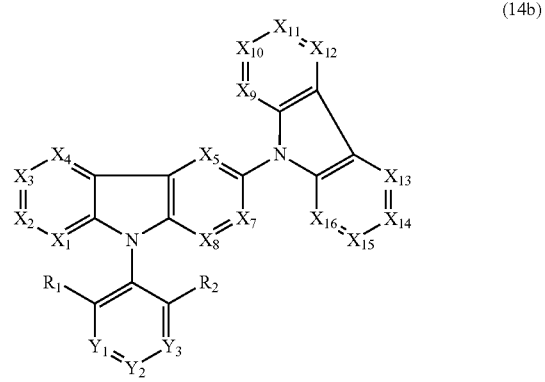

(14b)

In the formula (14b), $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_1$ to $X_5$ and $X_7$ to $X_1$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_5$, $X_7$ and $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded.

In the formula (14b), when $Y_1$ and $Y_3$ are nitrogen atoms and $Y_2$ is C—Ra, the first compound of the exemplary embodiment is represented by a formula (14c).

[Formula 29]

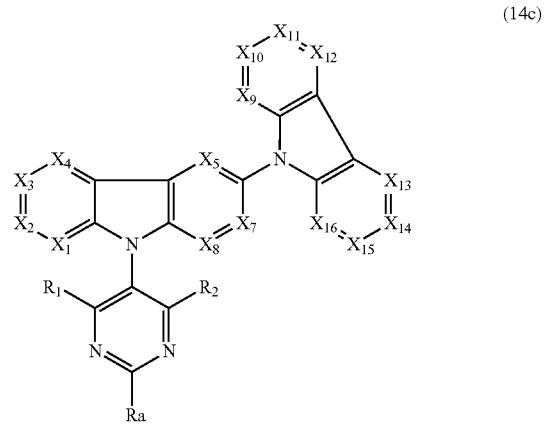

(14c)

In the formula (14c), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_5$ and $X_7$ to $X_1$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$ to $X_5$, $X_7$ and $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded.

The first compound of the exemplary embodiment is preferably represented by a formula (16b).

[Formula 30]

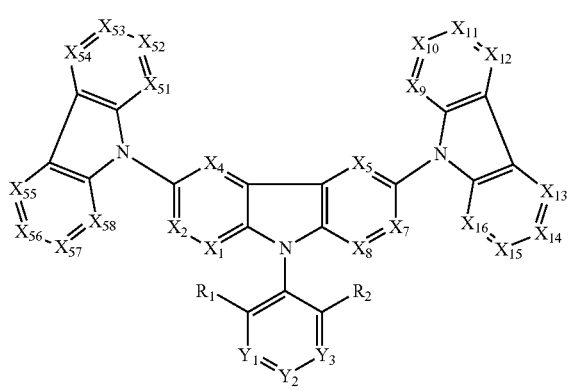

(16b)

In the formula (16b), $Y_1$, $Y_2$ and $Y_3$ each independently represent C—Ra or a nitrogen atom. At least one of $Y_1$, $Y_2$ and $Y_3$ is a nitrogen atom. $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. A plurality of Ra are mutually the same or different. At least one of $R_1$ and $R_2$ is a substituent. $X_1$, $X_2$, $X_4$, $X_5$, $X_7$ to $X_{16}$, and $X_{51}$ to $X_{58}$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$, $X_2$, $X_4$, $X_5$, $X_7$ and $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. When a plurality of ones of $X_{51}$ to $X_5$ are C—Rb and Rb is a substituent, a plurality of Rb are bonded to each other to form a ring, or are not bonded.

In the formula (16b), when $Y_1$ and $Y_3$ are nitrogen atoms and $Y_2$ is C—Ra, the first compound of the exemplary embodiment is represented by a formula (16c).

[Formula 31]

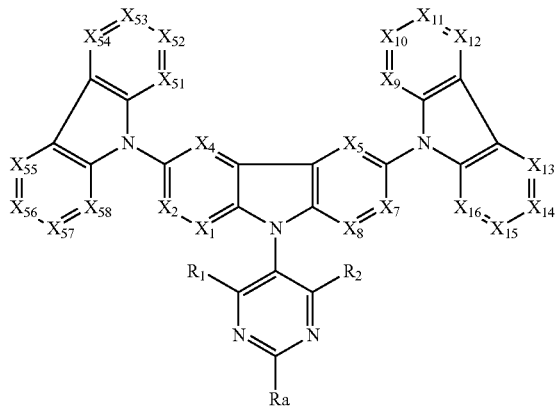

(16c)

In the formula (16c), $R_1$, $R_2$ and Ra each independently represent a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$, $X_2$, $X_4$, $X_5$, $X_7$ to $X_{16}$, and $X_{51}$ to $X_{58}$ each independently represent C—Rb or a nitrogen atom. Rb each independently represents a hydrogen atom or a substituent. Rb as the substituent represents the same as the above-described Rb as the substituent. A plurality of Rb are mutually the same or different. When a plurality of ones of $X_1$, $X_2$, $X_4$, $X_5$, $X_7$ and $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. When a plurality of ones of $X_{51}$ to $X_{58}$ are C—Rb and Rb is a substituent, a plurality of Rb are bonded to each other to form a ring, or are not bonded.

The first compound of the exemplary embodiment is preferably the compound represented by the formula (10B), more preferably, the compound represented by the formula (12a), further preferably, the compound represented by one of the formulae (13b), (14a) and (16a), still further preferably, the compound represented by one of the formulae (13e), (13f), (14c) and (16c), still further preferably, the compound represented by the formula (13e).

In the first compound of the exemplary embodiment, $X_1$ to $X_{16}$ are each independently preferably C—Rb. At this time, a plurality of Rb are each independently a hydrogen atom or a substituent. Rb as the substituent represents the same as the above-described Rb as the substituent. The plurality of Rb are mutually the same or different.

In the formula (1b), at least one of $X_5$ to $X_8$ is a carbon atom bonded to one of $X_9$ to $X_{12}$. At least one of $X_9$ to $X_{12}$ is a carbon atom bonded to one of $X_5$ to $X_8$.

In the formula (1c), at least one of $X_5$ to $X_8$ is a carbon atom bonded to a nitrogen atom in a five-membered ring of a nitrogen-containing fused ring including $X_9$ to $X_{16}$.

In the first compound of the exemplary embodiment, $X_{51}$ to $X_{58}$ are each independently preferably C—Rb. At this time, a plurality of Rb are each independently a hydrogen atom or a substituent. Rb as the substituent represents the same as the above-described Rb as the substituent. The plurality of Rb are mutually the same or different. In the formula (15a), at least one of $X_{55}$ to $X_{58}$ is a carbon atom bonded to one of $X_1$ to $X_4$, and at least one of $X_1$ to $X_4$ is a carbon atom bonded to one of $X_{55}$ to $X_5$.

In the first compound of the exemplary embodiment, it is preferable that $X_1$ to $X_{16}$ are C—Rb, Rb each independently represents a hydrogen atom or a substituent, Rb as the substituent is preferably selected from the group consisting of a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms, and the plurality of Rb are mutually the same or different.

In the formula (1b), at least one of $X_5$ to $X_8$ is a carbon atom bonded to one of $X_9$ to $X_{12}$, at least one of $X_9$ to $X_{12}$ is a carbon atom bonded to one of $X_5$ to $X_8$.

In the formula (1c), at least one of $X_5$ to $X_8$ is a carbon atom bonded to a nitrogen atom in a five-membered ring of a nitrogen-containing fused ring including $X_9$ to $X_{16}$.

In the first compound in the exemplary embodiment, it is preferable that $X_1$ to $X_{16}$ are C—Rb, Rb each independently represents a hydrogen atom or a substituent, Rb as the substituent is selected from the group consisting of a substituted or unsubstituted aryl group having 6 to 30 ring carbon atoms, and a plurality of Rb are mutually the same or different.

In the formula (1b), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$. In the formula (1c), at least one of $X_5$ to $X_8$ is a carbon atom bonded to a nitrogen atom in a five-membered ring of a nitrogen-containing fused ring including $X_9$ to $X_{16}$.

In the first compound of the exemplary embodiment, it is preferable that $X_1$ to $X_{16}$ are C—Rb and Rb is a hydrogen atom. In the formula (1b), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$.

In the formula (1c), at least one of $X_5$ to $X_8$ is a carbon atom bonded to a nitrogen atom in a five-membered ring of a nitrogen-containing fused ring including $X_9$ to $X_{16}$.

In the first compound of the exemplary embodiment, $R_1$ and $R_2$ are preferably substituents.

In the first compound in the exemplary embodiment, it is preferable that $R_1$ and $R_2$ are each independently selected from the group consisting of a substituted or unsubstituted alkyl group having 1 to 30 carbon atoms, a substituted or unsubstituted aryl group having 6 to 30 ring carbon atoms, a substituted or unsubstituted heteroaryl group having 5 to 30 ring atoms, and a cyano group. More preferably, $R_1$ and $R_2$ are each independently a substituted or unsubstituted aryl group having 6 to 30 ring carbon atoms. Further preferably, $R_1$ and $R_2$ are each independently a substituted or unsubstituted phenyl group.

In the first compound in the exemplary embodiment, it is preferable that Ra is a substituent; Ra as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and a plurality of Ra are mutually the same or different.

In the first compound in the exemplary embodiment, Ra is preferably selected from the group consisting of a substituted or unsubstituted alkyl group having 1 to 30 carbon atoms, a substituted or unsubstituted aryl group having 6 to 30 ring carbon atoms, a substituted or unsubstituted heteroaryl group having 5 to 30 ring atoms, and and a cyano group. Ra is more preferably a substituted or unsubstituted aryl group having 6 to 30 ring carbon atoms. Ra is further preferably a substituted or unsubstituted phenyl group.

In the first compound of the exemplary embodiment, $Y_1$ and $Y_3$ are preferably nitrogen atoms.

In the first compound of the exemplary embodiment, $Y_2$ is preferably C—Ra.

In the first compound of the exemplary embodiment, $R_1$, $R_2$ and Ra are preferably substituents at the same time.

In the first compound of the exemplary embodiment, it is preferable that $R_1$, $R_2$ and Ra are substituents at the same time while $Y_1$ and $Y_3$ are nitrogen atoms.

In the first compound in the exemplary embodiment, it is preferable that $R_1$, $R_2$ and Ra are each independently selected from the group consisting of a substituted or unsubstituted alkyl group having 1 to 30 carbon atoms, a substituted or unsubstituted aryl group having 6 to 30 ring carbon atoms, a substituted or unsubstituted heteroaryl group having 5 to 30 ring atoms, and and a cyano group. More preferably, $R_1$, $R_2$ and Ra are each independently a substituted or unsubstituted aryl group having 6 to 30 ring carbon atoms. Further preferably, $R_1$, $R_2$ and Ra are each independently a substituted or unsubstituted phenyl group.

In the first compound in the exemplary embodiment, it is preferable that Ara is selected from the group consisting of a substituted or unsubstituted aryl group having 6 to 30 ring carbon atoms, a substituted or unsubstituted heteroaryl group having 5 to 30 ring atoms. Ara is more preferably a substituted or unsubstituted aryl group having 6 to 30 ring carbon atoms. Ara is further preferably a substituted or unsubstituted phenyl group.

In the first compound of the exemplary embodiment, when the plurality of Rb are substituents, it is preferable that the plurality of Rb do not form a ring.

In the first compound of the exemplary embodiment, a skeleton represented by A in the formula has a carbazole ring skeleton as a basic skeleton.

When the carbazole ring in the skeleton represented by A is expanded, planarity of the skeleton represented by A is improved. When a thin film is formed from a compound having a skeleton improved in planarity, intermolecular interaction is reinforced in the thin film to sometimes decrease an energy gap of the compound. Herein, a case where the carbazole ring is expanded corresponds to a case where the plurality of Rb are mutually bonded to form a ring.

A compound exhibiting blue emission, which is used for the organic EL device, needs to be a compound having a large singlet energy gap. In order to provide the compound having a large singlet energy gap, the skeleton represented by A is preferably formed of a monocyclic carbazole ring (i.e., the ring is unexpanded). Herein, the monocyclic carbazole ring (i.e., the ring is unexpanded) corresponds to a case where the plurality of Rb are not mutually bonded (i.e., a ring is not formed).

Thermally Activated Delayed Fluorescence Characteristics

Delayed fluorescence (thermally activated delayed fluorescence) is described, for instance, on pages 261 to 268 of "Yuki Hando-tai no Debaisu Bussei (Device Physics of Organic Semiconductors)", edited by ADACHI, Chihaya and published by Kodansha Ltd. This literature describes that, when an energy gap $\Delta E_{13}$ between a singlet state and a triplet state can be decreased, an inverse energy transfer from the triplet state to the singlet state, which usually occurs at a low transition probability, occurs at a high efficiency to express thermally activated delayed fluorescence (TADF). Further, an occurrence mechanism of the delayed fluorescence is described in FIG. 10.38 of this literature. The compound of the exemplary embodiment is preferably a compound exhibiting thermally activated delayed fluorescence occurring in this mechanism.

Emission of the delayed fluorescence can be checked by measuring the transient PL (Photo Luminescence).

Behavior of the delayed fluorescence can be analyzed based on the decay curve obtained by the transient PL measurement. The transient PL measurement is a method of measuring decay behavior (transient characteristics) of the PL emission after radiating a pulse laser on a sample and stopping radiating. The PL emission in the TADF material is classified into a luminescence component from singlet excitons generated in first PL excitation and a luminescence component from singlet excitons generated through triplet excitons. A lifetime of the singlet excitons generated in the first PL excitation is very short in a nanosecond order. Accordingly, the emission from the singlet excitons rapidly decays after radiation of the pulse laser.

Figure 2:
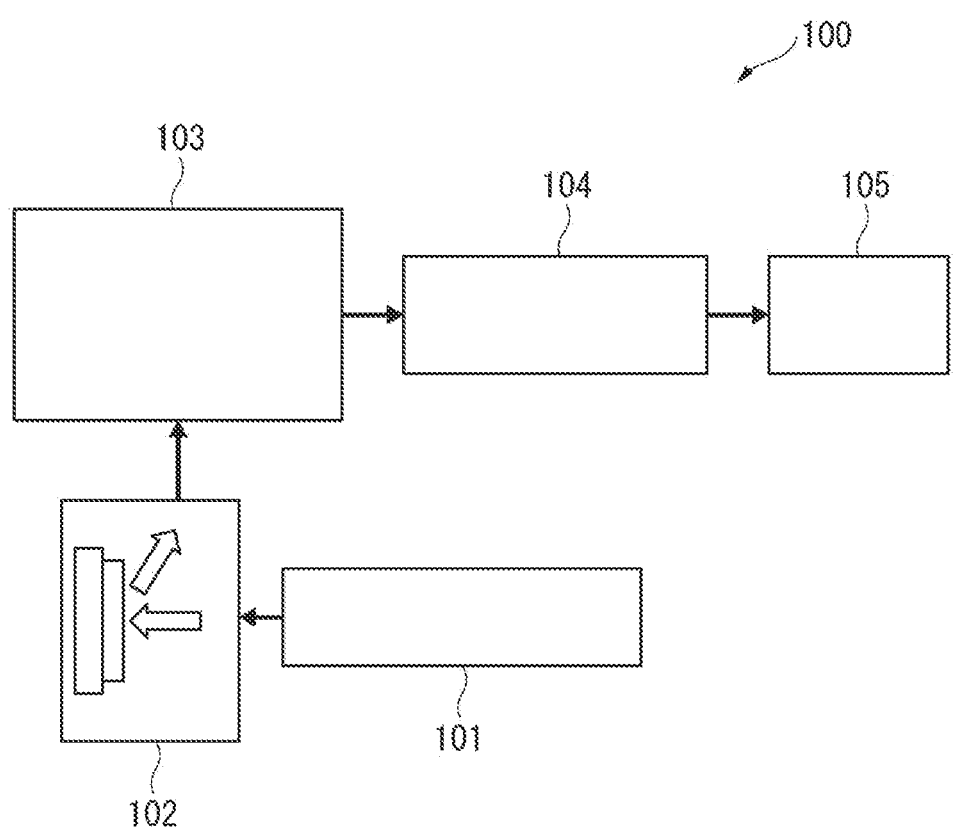
FIG. 2 is a schematic illustration of a measuring device of transient PL.

On the other hand, since delayed fluorescence provides an emission from singlet excitons generated through long-life triplet excitons, the delayed fluorescence gradually decays. Thus, there is a large difference in time between the emission from the singlet excitons generated in the first PL excitation and the emission from the singlet excitons through the triplet excitons. Accordingly, a luminous intensity derived from the delayed fluorescence is obtainable FIG. 2 schematically shows an exemplary device for measuring the transient PL.

A transient PL measuring device 100 in the exemplary embodiment includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by doping a matrix material with a doping material at a concentration of 12 mass % and forming a thin film on a quartz substrate.

The thin film sample housed in the sample chamber 102 is radiated with a pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above from a reference compound HX-1 as the matrix material and a reference compound DX-1 as the doping material and was measured in terms of the transient PL.

[Formula 32]

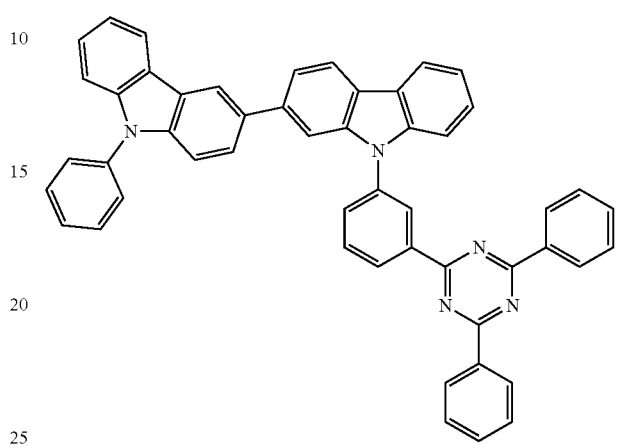

Reference Compound HX-1

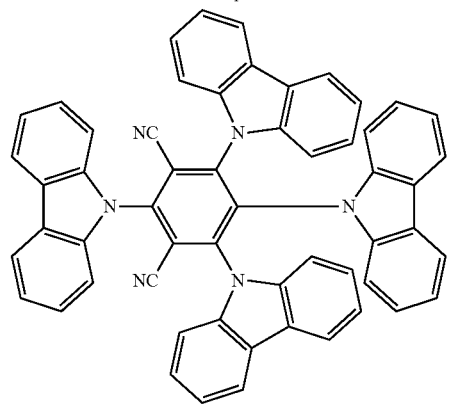

Reference Compound DX-1

The decay curve was analyzed with respect to the above thin film sample A and a thin film sample B. The thin film sample B was manufactured in the same manner as described above from a reference compound HX-2 as the matrix material and the reference compound DX-1 as the doping material.

Figure 3:
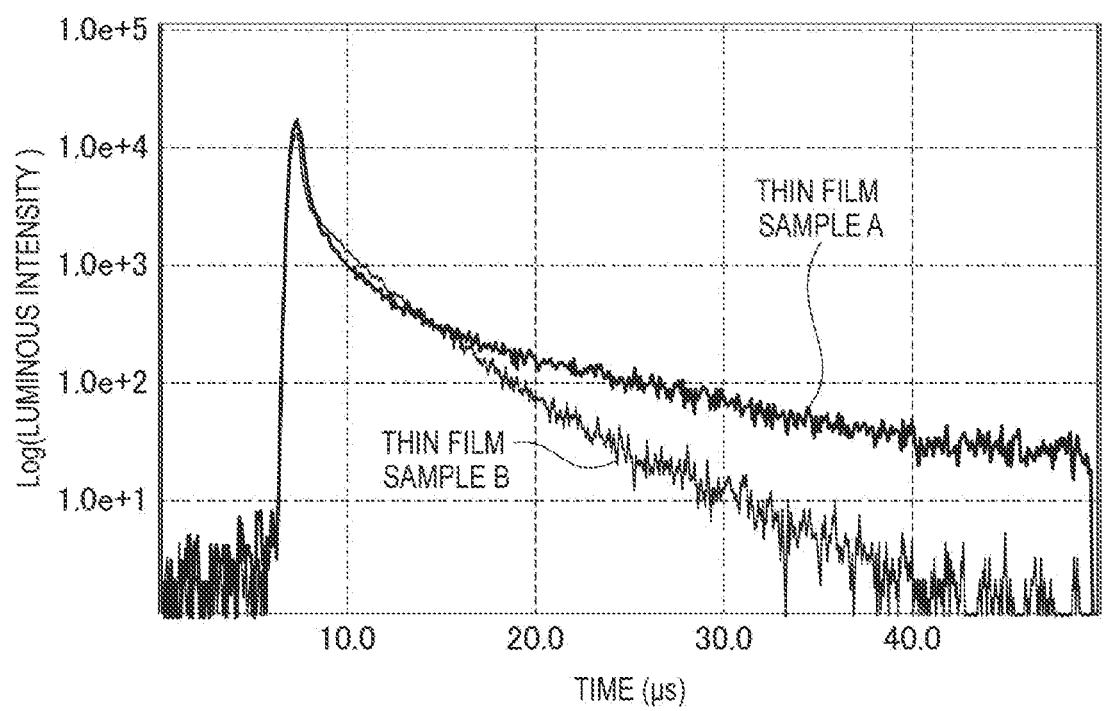
FIG. 3 shows an example of a decay curve of the transient PL.

FIG. 3 shows decay curves obtained from transient PL obtained by measuring the thin film samples A and B.

[Formula 33]

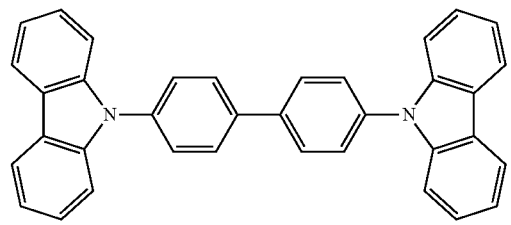

Reference Compound HX-2

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

In the exemplary embodiment, an emission amount of the delayed fluorescence can be obtained using the device shown in FIG. 2. Prompt emission and Delay emission are observed in the compound of the exemplary embodiment. Prompt emission is observed promptly when the excited state is achieved by exciting the compound of the exemplary embodiment with a pulse beam (i.e., a beam emitted from a pulse laser) having a wavelength absorbable by the first compound. Delay emission is observed not promptly when the excited state is achieved but after the excited state is achieved. In the exemplary embodiment, provided that the amount of Prompt emission is denoted by XP and the amount of Delay emission is denoted by XD, a value of XD/XP is preferably 0.05 or more.

The amount of Prompt emission and the amount of Delay emission can be obtained according to the method as described in "Nature 492, 234-238, 2012." The amount of Prompt emission and the amount of Delay emission may be calculated using a device different from one described in the above literature.

Moreover, a sample usable for measuring delayed fluorescence is obtained, for instance, by co-depositing the compound of the exemplary embodiment and a compound TH-2 below on a quartz substrate at a ratio of the compound of the exemplary embodiment of 12 mass % to form a 100-nm-thick thin film.

[Formula 34]

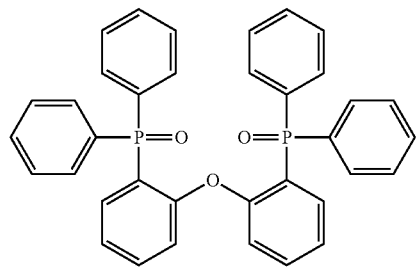

TH-2

Manufacturing Method of Compound

The compound according to the exemplary embodiment can be manufactured by, for instance, a method described in Examples described below. The compound according to the exemplary embodiment can be manufactured by application of known substitution reactions and/or materials depending on a target compound according to reactions described later in Examples.

Examples of the compound according to the exemplary embodiment are given below. It should be noted that the compound of the exemplary embodiment is not limited to the examples.

[Formula 35]

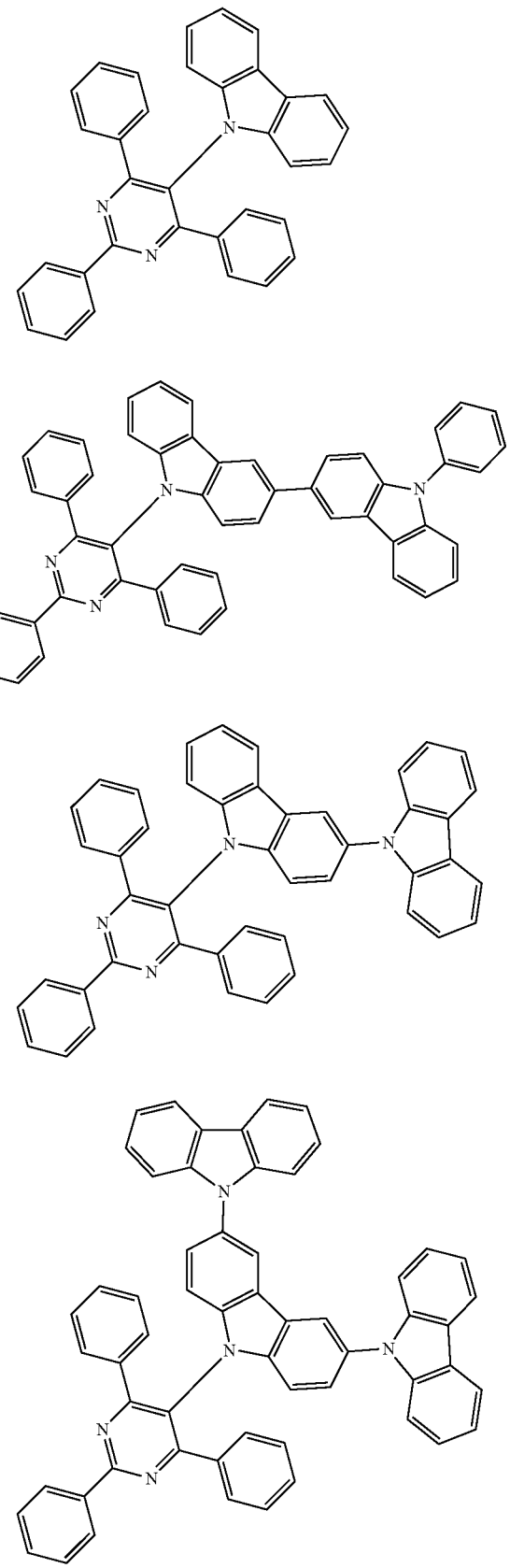

[Formula 36]
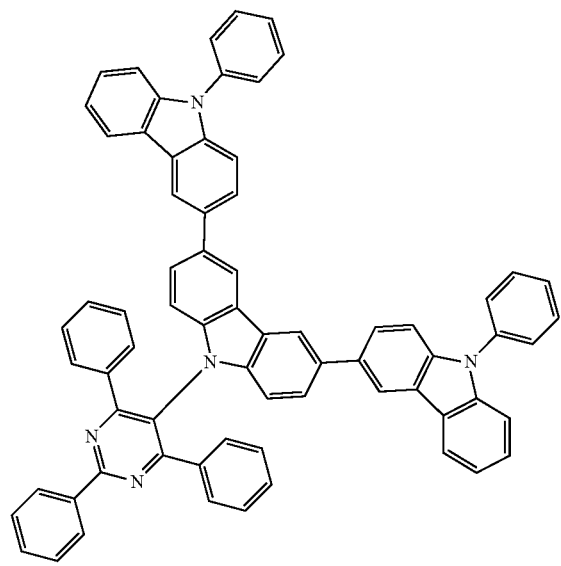
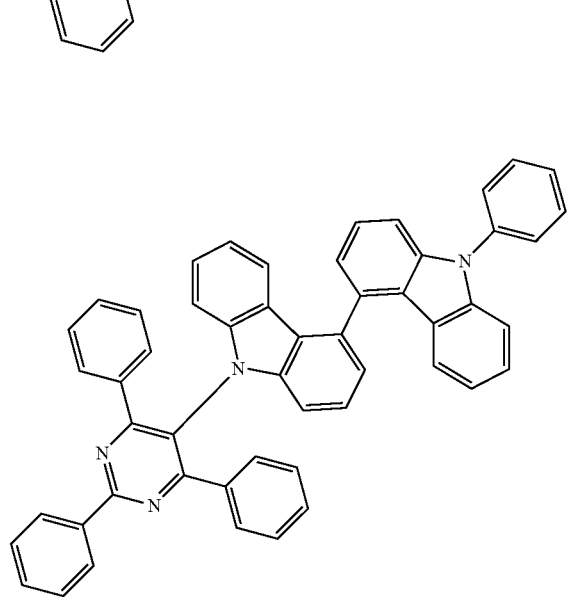
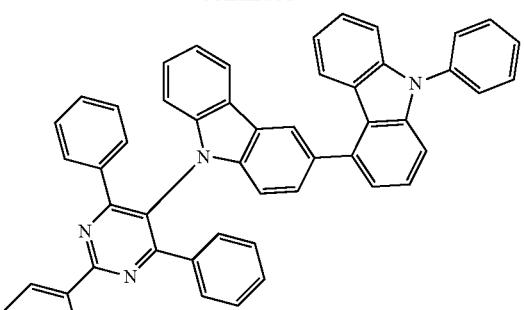
[Formula 37]
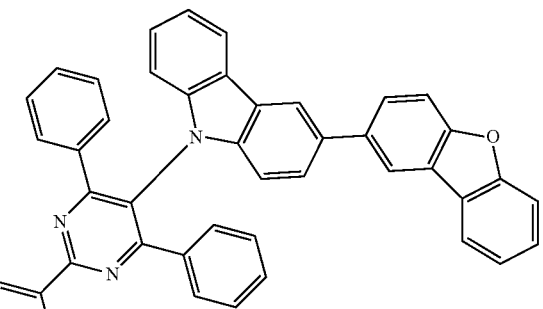
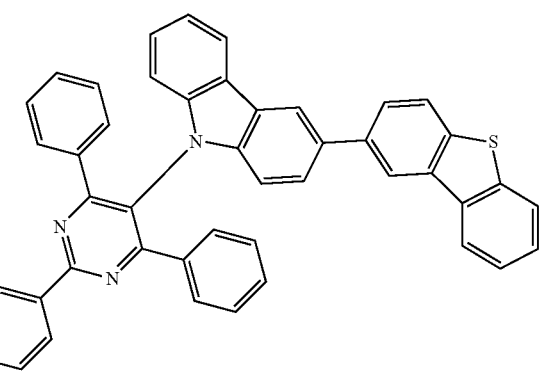
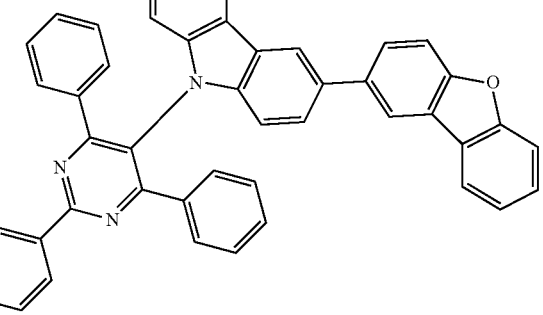

[Formula 38]
[Formula 39]
[Formula 40]
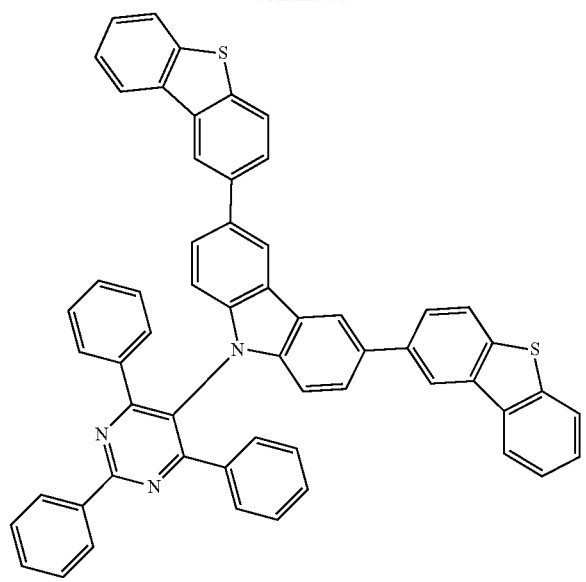
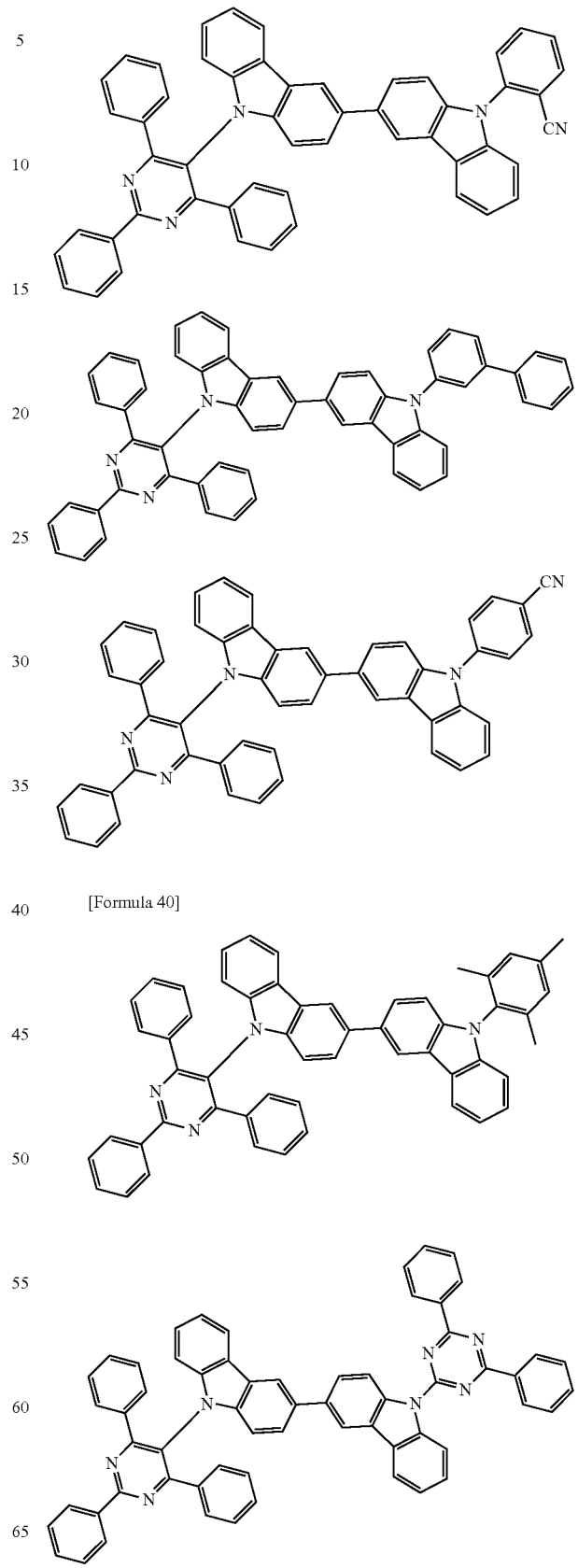

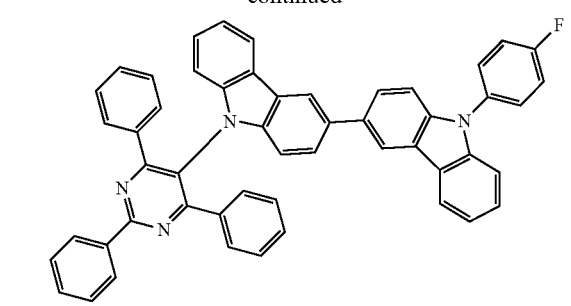
[Formula 41]
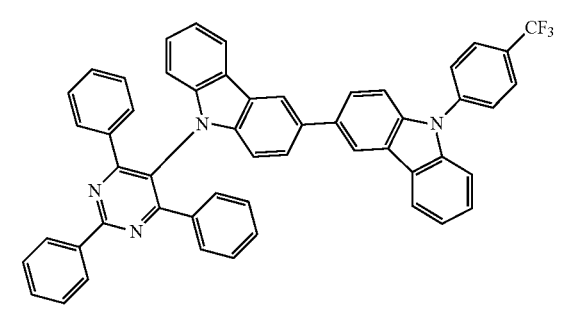
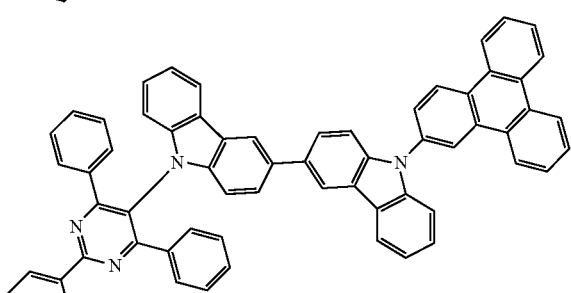
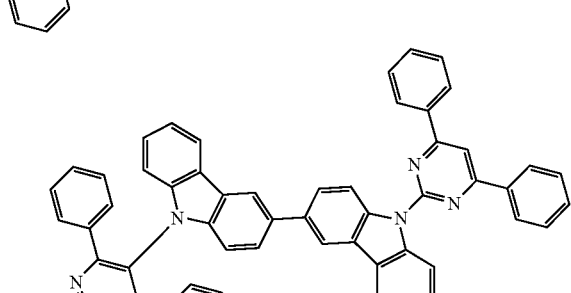
[Formula 42]
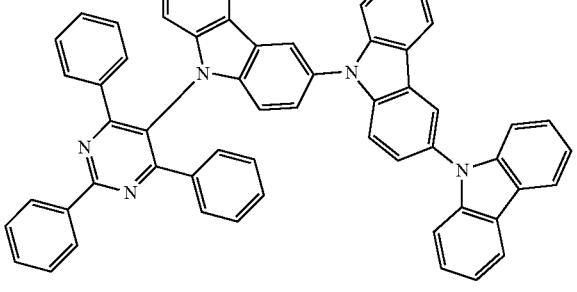
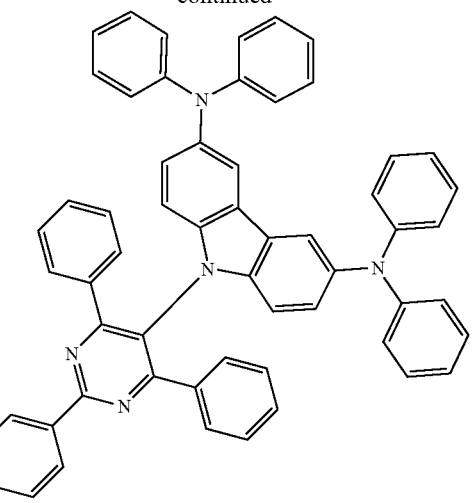
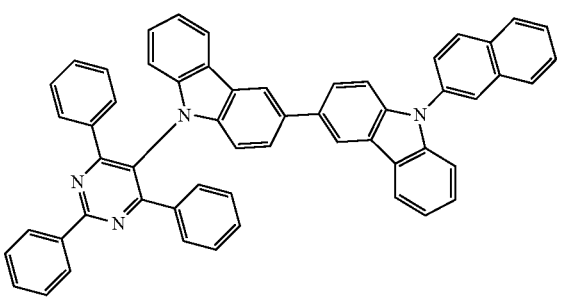
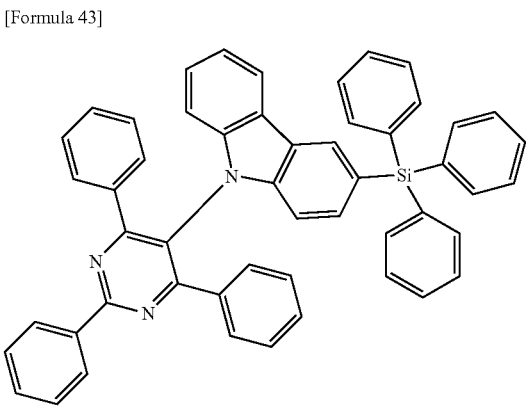
[Formula 43]
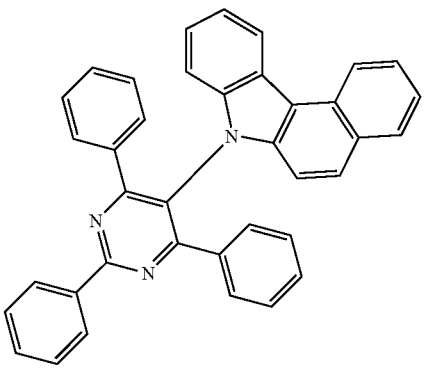

-continued
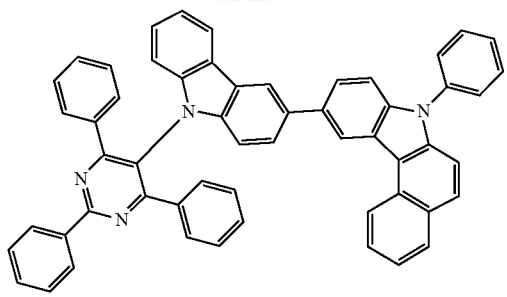
[Formula 44]
-continued
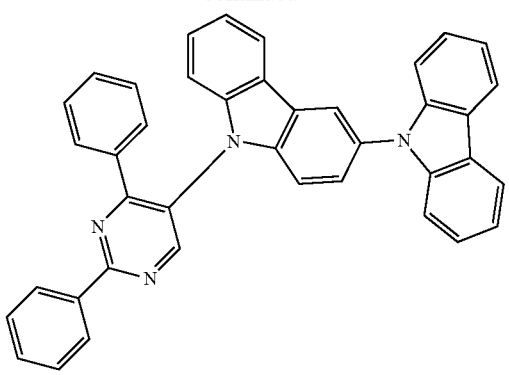
[Formula 45]

[Formula 46]
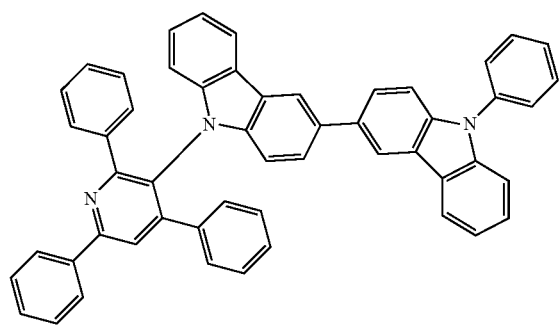
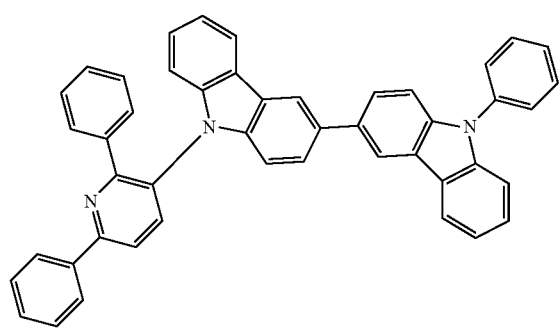
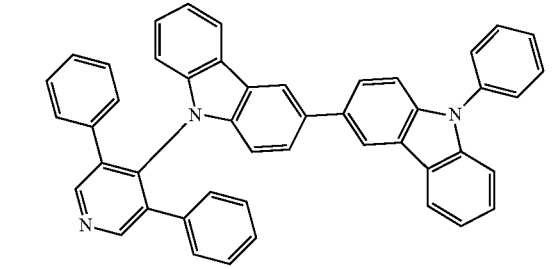
[Formula 47]
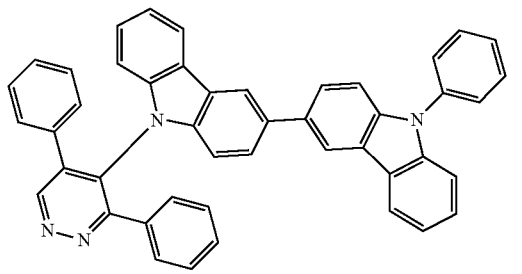
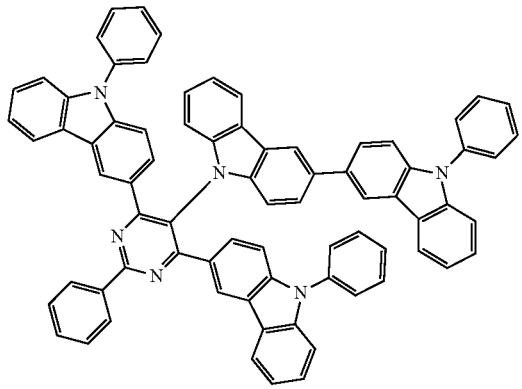
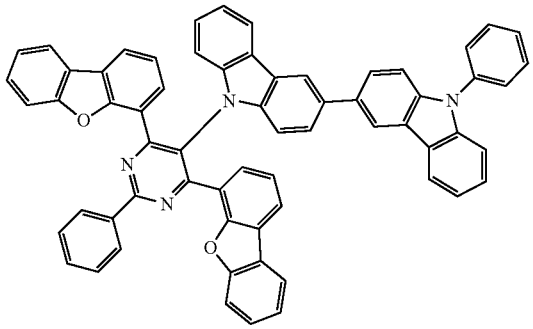
[Formula 48]
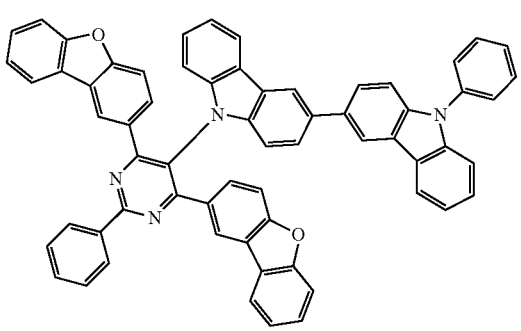
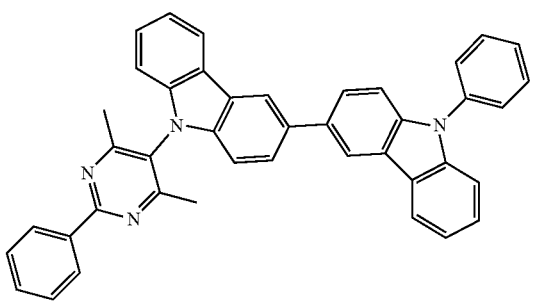
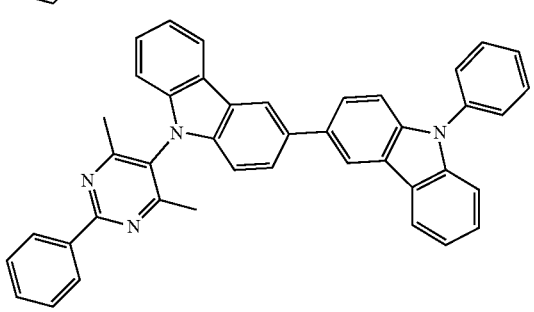
[Formula 49]
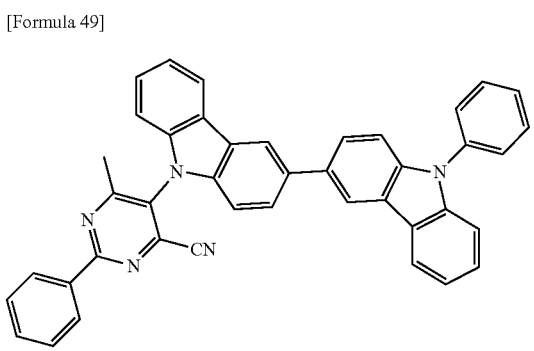

-continued
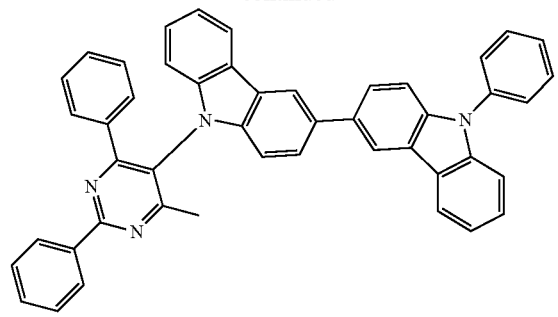
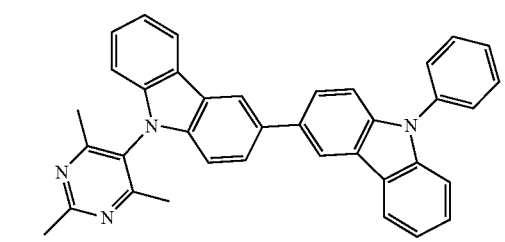
[Formula 50]
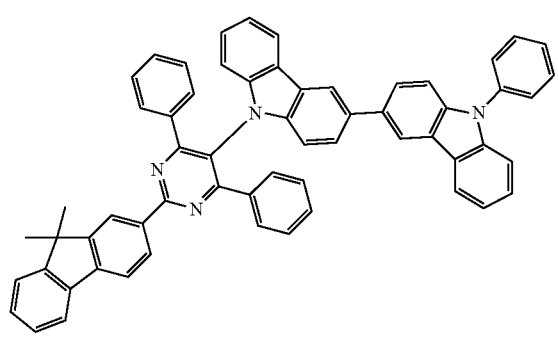
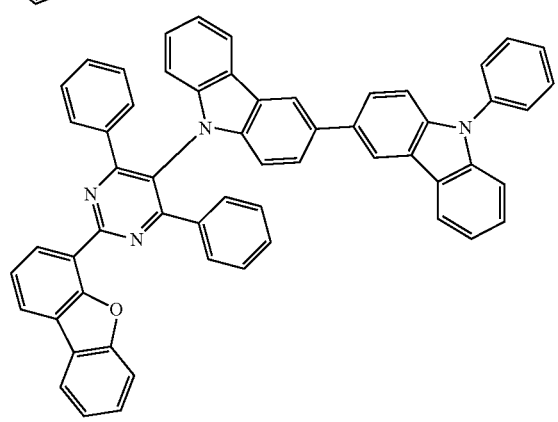
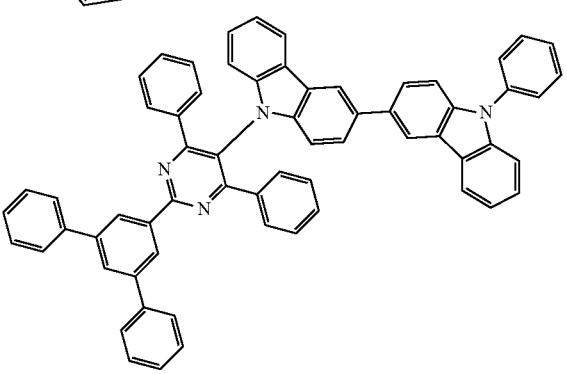
-continued
[Formula 51]
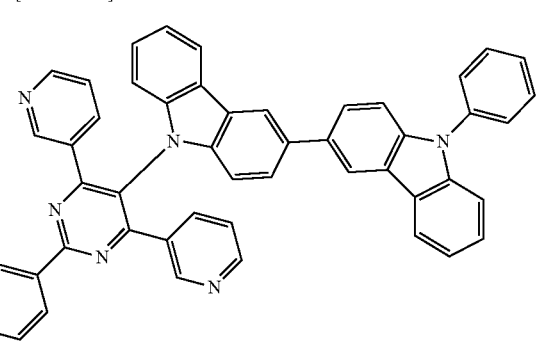
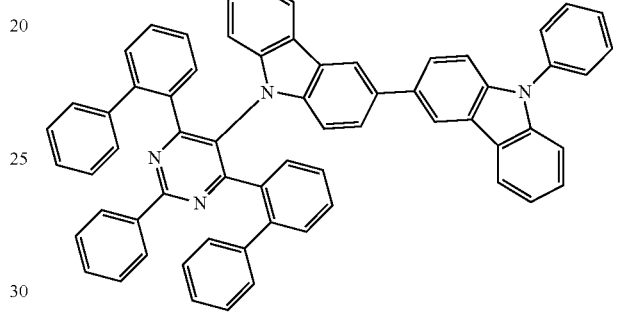
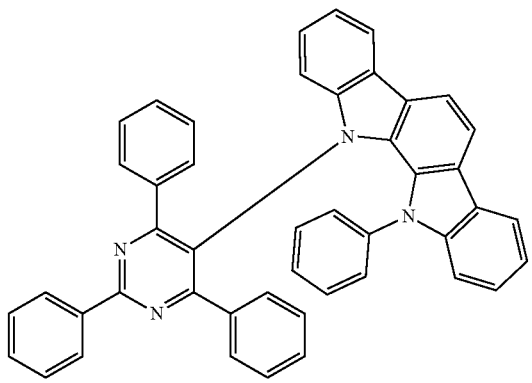
[Formula 52]
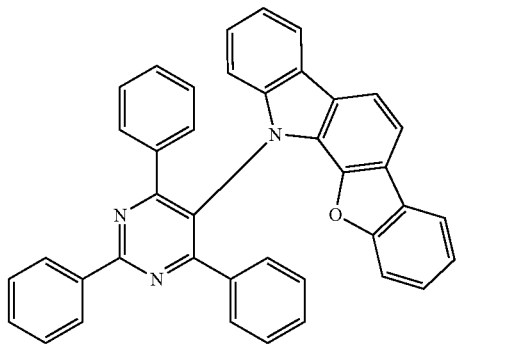

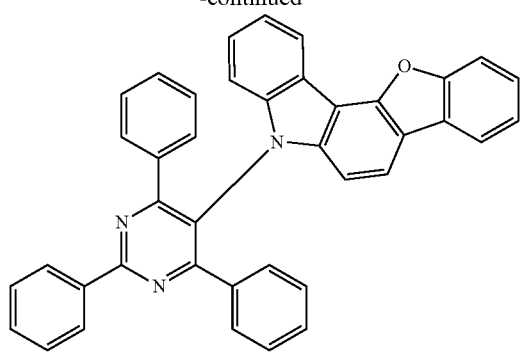
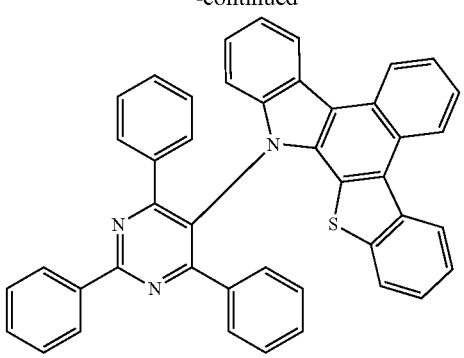
[Formula 54]
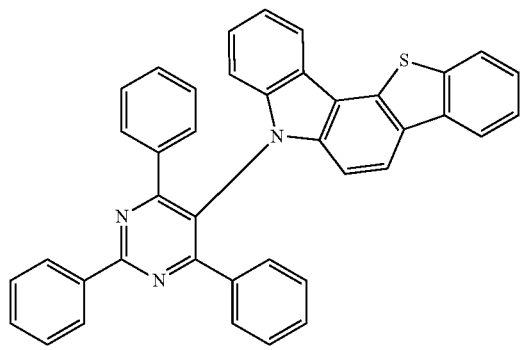
[Formula 53]
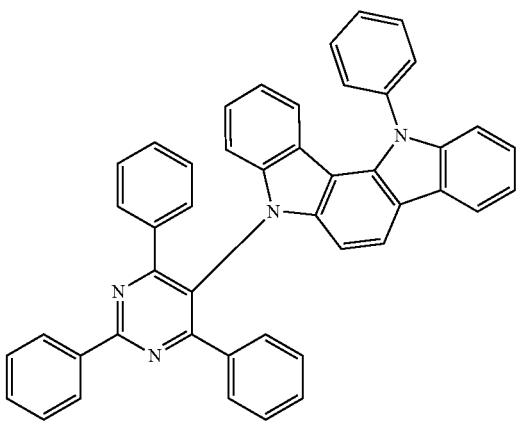
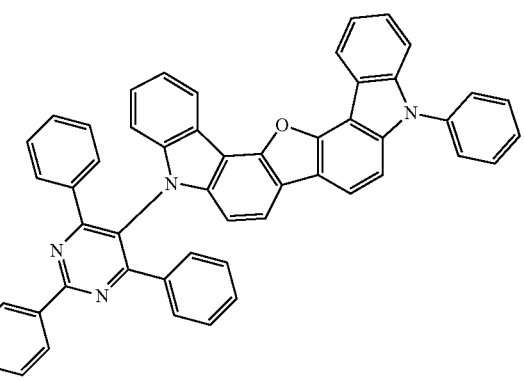
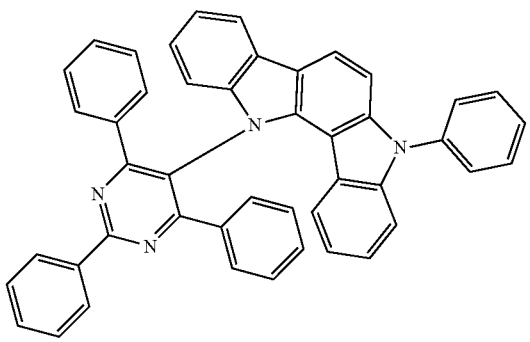
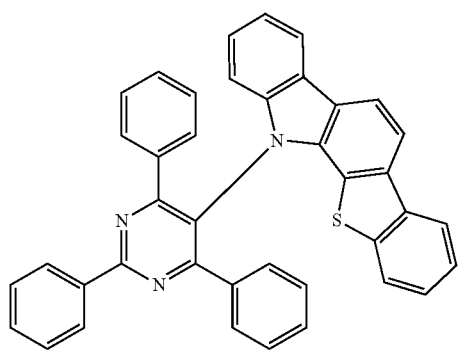
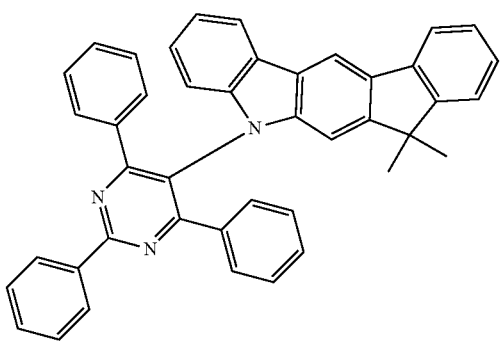
The first compound of the exemplary embodiment is preferably a thermally activated delayed fluorescent compound. Accordingly, in the organic EL device in the exemplary embodiment, a thermally activated delayed fluorescent compound is selected for use from the first compound of the exemplary embodiment In order to improve thermally activated delayed fluorescence, a gap ($\Delta ST$) between an energy in the lowest singlet state and an energy in the lowest triplet state is preferably small.

Moreover, for a small $\Delta ST$ in an organic compound, it is preferable to localize Highest Occupied Molecular Orbital (HOMO) and Lowest Unoccupied Molecular Orbital level (LUMO) in molecules, not in coexistence of HOMO and LUMO.

In the first compound of the exemplary embodiment, it is expected that HOMO is localized mainly in the skeleton represented by A in the formula while LUMO is localized mainly in a nitrogen-containing heteroaromatic ring containing $Y_1$, $Y_2$ and $Y_3$ in the formula.

When one of $R_1$ and $R_2$ is a substituent, it is inferred that, since the skeleton represented by A and the nitrogen-containing heteroaromatic ring are twisted, coexistence of HOMO and LUMO is suppressed.

Further, when both of $R_1$ and $R_2$ are substituents, it is inferred that the coexistence of HOMO and LUMO is further suppressed to significantly contribute to a reduction in $\Delta ST$.

Moreover, in the first compound of the exemplary embodiment, since the skeleton represented by A in the formula is directly bonded to the nitrogen-containing heteroaromatic ring, $R_1$ and $R_2$ are present near a bonding position of the skeleton and the nitrogen-containing heteroaromatic ring. Accordingly, it is inferred that twist of at least one of substituents of $R_1$ and $R_2$ significantly contributes to the whole molecule to effectively suppress the coexistence of HOMO and LUMO.

Fluorescent Compound

A fluorescent compound is used in the organic EL device of the exemplary embodiment. The fluorescent compound of the exemplary embodiment is not particularly limited.

The fluorescent compound preferably has a main peak wavelength in a range from 430 nm to 480 nm, more preferably in a range from 445 nm to 480 nm. Herein, the main peak wavelength means a peak wavelength of an emission spectrum exhibiting a maximum luminous intensity among emission spectra measured in a toluene solution in which a measurement target compound is dissolved at a concentration ranging from $10^{-6}$ mol/l to $10^{-5}$ mol/l.

The fluorescent compound preferably fluoresces blue.

The fluorescent compound is preferably a compound having a high emission quantum efficiency.

A fluorescent material is usable as the fluorescent compound of the exemplary embodiment. Examples of a blue fluorescent compound include a pyrene derivative, styrylamine derivative, chrysene derivative, fluoranthene derivative, fluorene derivative, diamine derivative, and triarylamine derivative. Examples of a green fluorescent compound include a coumarin derivative, a pyrromethene boron complex, and an aromatic amine derivative. Examples of a red fluorescent compound include a tetracene derivative, a perifianthene derivative, a pyrromethene boron complex, and a diamine derivative.

The fluorescent compound of the exemplary embodiment is preferably represented by a formula (20).

[Formula 55]

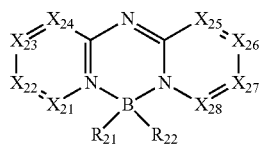

(20)

In the formula (20), $R_{21}$ and $R_{22}$ each independently represent a hydrogen atom or a substituent.

$R_{21}$ and $R_{22}$ as the substituents are each independently a group selected from the group consisting of a halogen atom, a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

$R_{21}$ and $R_{22}$ as the substituents are directly bonded to each other to form a ring, or are not bonded to each other.

$X_{21}$ to $X_{28}$ each independently represent a carbon atom bonded to $R_{23}$ (C—$R_{23}$) or a nitrogen atom.

$R_{23}$ represents a hydrogen atom or a substituent. $R_{23}$ as the substituent is a group selected from the group consisting of a halogen atom, a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group. A plurality of $R_{23}$ as the substituents are mutually the same or different. The plurality of $R_{23}$ as the substituents are directly bonded to each other to form a ring, bonded to each other through a hetero atom to form a ring, or not bonded to each other. The ring formed by bonding $R_{21}$ and $R_{22}$ as the substituents and the ring formed by bonding the plurality of $R_{23}$ as the substituents are preferably a five-membered ring, a six-membered ring, or a seven-membered ring, which may be an aliphatic ring, an aromatic hydrocarbon ring, or a heterocyclic ring and may be further substituted. A plurality of rings are mutually the same or different.

In the exemplary embodiment, $X_{21}$ to $X_{28}$ are each independently preferably a carbon atom bonded to $R_{23}$. In this arrangement, the fluorescent compound is represented by a formula (21). In the formula (21), $R_{231}$ to $R_{238}$ each independently represent the same as the above-described $R_{23}$ while $R_{21}$ and $R_{22}$ each independently represent the same as the above-described $R_{21}$ and $R_{22}$.

[Formula 56]

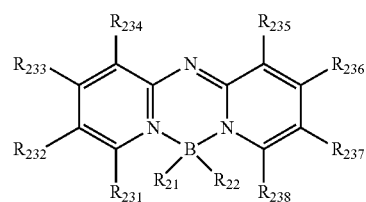

(21)

In the exemplary embodiment, it is preferable that a pair of ones of $R_{231}$ to $R_{234}$ are substituents and the substituents are mutually bonded to form a ring, or a pair of ones of $R_{235}$ to $R_{238}$ are substituents and the substituents are mutually bonded to form a ring.

In the exemplary embodiment, it is also preferable that a pair of ones of $R_{231}$ to $R_{234}$ being substituents are mutually bonded to form a ring, and further, a pair of ones of $R_{235}$ to $R_{238}$ being substituents are mutually bonded to form a ring. The ring formed by bonding the substituents is preferably a six-membered aromatic hydrocarbon ring. The six-membered aromatic hydrocarbon ring may be further substituted.

The fluorescent compound of the exemplary embodiment is also preferably represented by a formula (22).

[Formula 57]

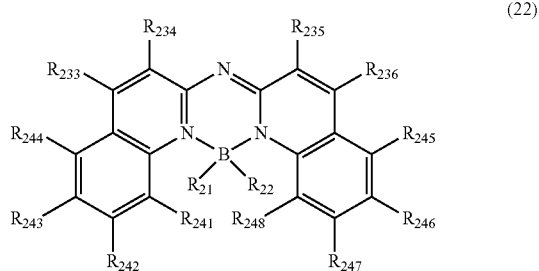

(22)

In the formula (22), $R_{233}$ to $R_{238}$ and $R_{241}$ to $R_{248}$ each independently represent the same as the above-described $R_{23}$ while $R_{21}$ and $R_{22}$ each independently represent the same as the above-described $R_{21}$ and $R_{22}$.

In the formula (22), it is preferable that $R_{241}$, $R_{242}$, $R_{244}$, $R_{245}$, $R_{247}$ and $R_{248}$ are hydrogen atoms, and $R_{243}$ and $R_{246}$ are substituents. $R_{243}$ and $R_{246}$ as the substituents are each independently a group selected from the group consisting of a halogen atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group. $R_{243}$ and $R_{246}$ as the substituents are each independently preferably a group selected from the group consisting of a halogen atom, a substituted or unsubstituted aryl group having 6 to 30 ring carbon atoms, and a substituted or unsubstituted alkyl group having 1 to 30 carbon atoms, more preferably a substituted or unsubstituted aryl group having 6 to 30 ring carbon atoms.

In the exemplary embodiment, $R_{21}$ and $R_{22}$ are each independently preferably a substituent selected from the group consisting of a halogen atom, a substituted or unsubstituted aryl group having 6 to 30 ring carbon atoms, and a substituted or unsubstituted alkyl group having 1 to 30 carbon atoms, more preferably a halogen atom, further preferably a fluorine atom.

Specific examples of the fluorescent compound of the exemplary embodiment are shown below. The fluorescent compound of the exemplary embodiment are not limited to the examples below.

[Formula 58]

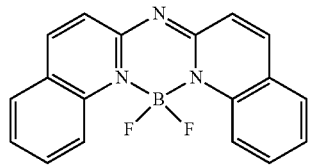

[Formula 59]

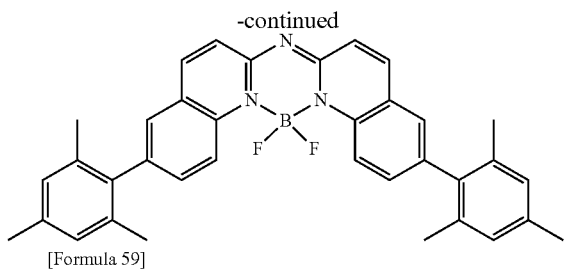

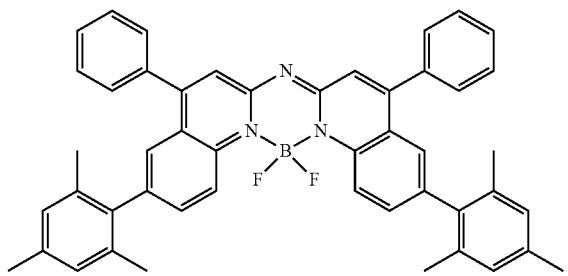

Relationship Between First Compound and Fluorescent Compound in Emitting Layer

In the organic EL device 1 of the exemplary embodiment, a singlet energy $S_1(M1)$ of the first compound and a singlet energy $S_1(FL)$ of the fluorescent compound satisfy a relationship of the following numerical formula (Numerical Formula 1) below, $$S_1(M1) > S_1(FL) \qquad \text{(Numerical Formula 1)}.$$

An energy gap $T_{77K}(M1)$ at 77 [K] of the first compound is preferably larger than an energy gap $T_{77K}(FL)$ at 77 [K] of the fluorescent compound. In other words, a relationship of the following numerical formula (Numerical Formula 4) is preferably satisfied.

$$T_{77K}(M1) > T_{77K}(FL) \qquad \text{(Numerical Formula 4)}.$$

When the organic EL device 1 of the exemplary embodiment emits light, it is preferable that the fluorescent compound in the emitting layer 5 mainly emits light.

Relationship Between Triplet Energy and Energy Gap at 77K

Here, a relationship between a triplet energy and an energy gap at 77K will be described. In the exemplary embodiment, the energy gap at 77 [K] is different from a typical triplet energy in some aspects.

Triplet energy is measured as follows. Firstly, a solution in which a compound (measurement target) is dissolved in an appropriate solvent is encapsulated in a quartz glass tube to prepare a sample. A phosphorescent spectrum (ordinate axis:phosphorescent luminous intensity, abscissa axis: wavelength) of the sample is measured at a low temperature (77K). A tangent is drawn to the rise of the phosphorescent spectrum close to the short-wavelength region. The triplet energy is calculated by a predetermined conversion equation based on a wavelength value at an intersection of the tangent and the abscissa axis.

Here, the thermally activated delayed fluorescent compound among the compounds of the exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 µmol/L, and the obtained solution is encapsulated in a quartz cell to provide a measurement sample. A phosphorescent spectrum (ordinate axis:phosphorescent luminous intensity, abscissa axis: wavelength) of the sample is measured at a low temperature (77K). A tangent is drawn to the rise of the phosphorescent spectrum close to the short-wavelength region. An energy amount is calculated by a conversion equation below based on a wavelength value $\lambda_{edge}$ [nm] at an intersection of the tangent and the abscissa axis and is defined as an energy gap $T_{77K}$ at 77 [K].

$T_{77K}$ [eV]=1239.85/$\lambda_{edge}$     Conversion Equation (F1):

The tangent to the rise of the phosphorescence spectrum close to the short-wavelength region is drawn as follows. While moving on a curve of the phosphorescence spectrum from the short-wavelength region to the maximum spectral value closest to the short-wavelength region among the maximum spectral values, a tangent is checked at each point on the curve toward the long-wavelength of the phosphorescence spectrum. An inclination of the tangent is increased along the rise of the curve (i.e., a value of the ordinate axis is increased). A tangent drawn at a point of the maximum inclination (i.e., a tangent at an inflection point) is defined as the tangent to the rise of the phosphorescence spectrum close to the short-wavelength region.

The maximum with peak intensity being 15% or less of the maximum peak intensity of the spectrum is not included in the above-mentioned maximum closest to the short-wavelength region. The tangent drawn at a point of the maximum spectral value being closest to the short-wavelength region and having the maximum inclination is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy $S_1$

A method of measuring a singlet energy $S_1$ with use of a solution (occasionally referred to as a solution method) is exemplified by a method below.

A toluene solution in which a measurement target compound is dissolved at a concentration of 10 µmol/L is prepared and is encapsulated in a quartz cell to provide a measurement sample. Absorption spectrum (ordinate axis: luminous intensity, abscissa axis: wavelength) of the sample is measured at the normal temperature (300K). A tangent is drawn to the fall of the absorption spectrum close to the long-wavelength region, and a wavelength value λedge (nm) at an intersection of the tangent and the abscissa axis is obtained. The wavelength value λedge (nm) is substituted in a conversion equation (F2) below to calculate a singlent energy.

$S_1$ [eV]=1239.85/λedge     Conversion Equation (F2):

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the maximum spectral value closest to the long-wavelength region in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength region (except when absorbance is 0.1 or less) is defined as the tangent to the fall of the absorption spectrum close to the long-wavelength region.

The maximum absorbance of 0.2 or less is not included in the above-mentioned maximum absorbance close to the long-wavelength region.

Content Ratio of Compounds in Emitting Layer

Content ratios of the respective first compound and fluorescent compound in the emitting layer 5 preferably range as follows.

The content ratio of the first compound preferably ranges from 90 mass % to 99.9 mass %, more preferably from 95 mass % to 99.9 mass %, further preferably from 99 mass % to 99.9 mass %.

The content ratio of the fluorescent compound preferably ranges from 0.01 mass % to 10 mass %, more preferably from 0.01 mass % to 5 mass %, further preferably from 0.01 mass % to 1 mass %.

It should be noted that the emitting layer 5 of the exemplary embodiment may contain a material other than the first compound and the fluorescent compound.

Thickness of Emitting Layer

A thickness of the emitting layer 5 preferably ranges from 5 nm to 50 nm, more preferably from 7 nm to 50 nm, further preferably from 10 nm to 50 nm. The emitting layer 5 having the thickness of 5 nm or more is easily formable and easily adjustable in chromaticity. The emitting layer 5 having the thickness of 50 nm or less can restrain a rise in the drive voltage.

TADF Mechanism

Figure 4:
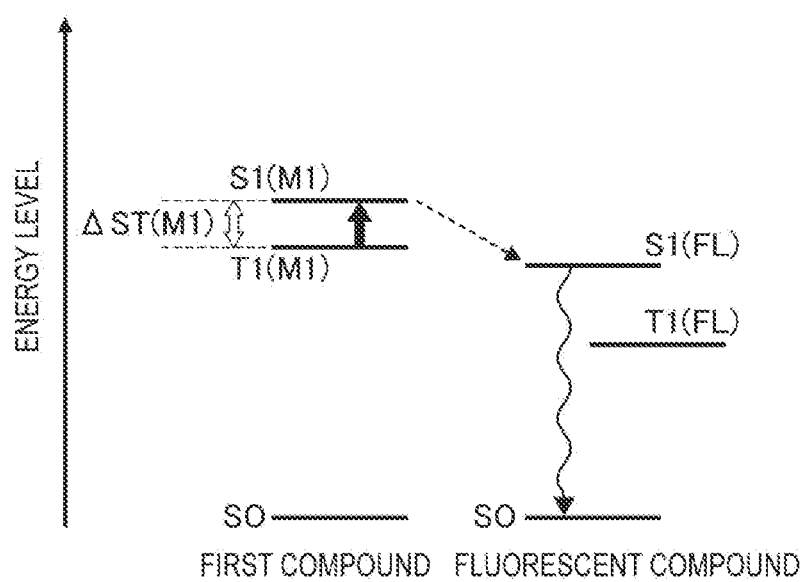
FIG. 4 shows a relationship between energy levels of a first compound and a fluorescent compound and an energy transfer between the first compound and the fluorescent compound in an emitting layer of an exemplary organic electroluminescence device of the first exemplary embodiment of the invention.

FIG. 4 shows an example of a relationship between energy levels of the first compound and the fluorescent compound in the emitting layer. In FIG. 4, S0 represents a ground state. S1(M1) represents the lowest singlet state of the first compound. T1(M1) represents the lowest triplet state of the first compound. S1(FL) represents the lowest singlet state of the fluorescent compound. T1(FL) represents the lowest triplet state of the fluorescent compound.

A dashed arrow directed from S1(M1) to S1(FL) in FIG. 4 represents Förster energy transfer from the lowest singlet state of the first compound to the lowest singlet state of the fluorescent compound.

As shown in FIG. 4, when a compound having a small ΔST(M1) is used as the first compound, inverse intersystem crossing from the lowest triplet state T1(M1) to the lowest singlet state S1(M1) can be caused by a heat energy. Subsequently, Förster energy transfer from the lowest singlet state S1(M1) of the first compound the fluorescent compound occurs to generate the lowest singlet state S1(FL). Consequently, fluorescence from the lowest singlet state S1(FL) of the fluorescent compound can be observed. It is inferred that the internal quantum efficiency can be theoretically raised up to 100% also by using delayed fluorescence by the TADF mechanism. $\Delta ST(M1)$ represents $\Delta ST$ of the first compound and can be calculated by $\Delta ST(M1)=S1(M1)-T_{77K}(M1)$.

Substrate

The substrate 2 is used as a support for the organic EL device 1. For instance, glass, quartz, plastics and the like are usable as the substrate 2. A flexible substrate is also usable. The flexible substrate is a bendable substrate, which is exemplified by a plastic substrate. Examples of a material for forming the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal having a large work function (specifically, 4.0 eV or more), alloy, an electrically conductive compound and a mixture thereof are preferably usable as the anode 3 formed on the substrate 2. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), nitrides of these metal materials (e.g., titanium nitride) and the like are usable.

The above materials are typically formed into a film by sputtering. For instance, a target of the indium zinc oxide which is prepared by adding zinc oxide in a range from 1 mass % to 10 mass % relative to indium oxide is used for forming a film by sputtering. Moreover, for instance, as for the indium oxide containing tungsten oxide and zinc oxide, a target thereof prepared by adding tungsten oxide in a range from 0.5 mass % to 5 mass % and zinc oxide in a range from 0.1 mass % to 1 mass % relative to indium oxide is usable for forming a film by sputtering. In addition, vapor deposition, coating, ink jet printing, spin coating and the like may be used for forming a film.

Among the organic layers formed on the anode 3, the hole injecting layer 6 formed adjacent to the anode 3 is formed of a composite material in which holes are easily injectable irrespective of the work function of the anode 3. Accordingly, other materials usable as an electrode material (e.g., a metal, alloy, electrically conductive compound, mixture thereof, and elements belonging to Group 1 or 2 in the periodic table of the elements) are also usable for the anode 3.

A material having a small work function such as elements belonging to Groups 1 and 2 in the periodic table of the elements, a rare earth metal and an alloy including the elements and/or the rare earth metal are also usable for the anode 3. Examples of the elements belonging to Group 1 in the periodic table of the elements include an alkali metal. Examples of the elements belonging to Group 2 in the periodic table of the elements include an alkaline earth metal. Examples of the alkali metal include lithium (Li) and cesium (Cs). Examples of the alkaline earth metal include magnesium (Mg), calcium (Ca) and strontium (Sr). Examples of the rare earth metal include europium (Eu) and ytterbium (Yb). Examples of the alloy include MgAg and AlLi.

When the anode 3 is formed of the alkali metal, alkaline earth metal and alloys thereof, vapor deposition and sputtering are usable. Moreover, when the anode 3 is formed of silver paste and the like, coating, ink jet printing and the like are usable.

Hole Injecting Layer

The hole injecting layer 6 is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

Moreover, a macromolecular compound is also usable as the highly hole-injectable substance. Examples of the macromolecular compound include an oligomer, dendrimer and polymer. Specific examples of the macromolecular compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido](abbreviation: PTPDMA), and poly[N,N'-bis(4-butylphenyl)-N,N'-bis(phenyl)benzidine] (abbreviation: Poly-TPD). Moreover, the examples of the macromolecular compound include a macromolecular compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

The hole transporting layer 7 is a layer containing a highly hole-transporting substance. For instance, an aromatic amine compound, carbazole derivative, anthracene derivative and the like are usable for the hole transporting layer 7. Specifically, for instance, an aromatic amine compound is usable for the hole transporting layer. Examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V-s) or more.

A carbazole derivative (e.g., CBP, 9-[4-(N-carbazolyl)]phenyl-10-phenylanthracene (CzPA), and 9-phenyl-3-[4-(10-phenyl-9-anthryl)phenyl]-9H-carbazole (PCzPA)) and an anthracene derivative (e.g., t-BuDNA, DNA, and DPAnth) may be used for the hole transporting layer 7. Moreover, a macromolecular compound such as poly(N- vinylcarbazole) (abbreviation: PVK) and poly(4-vinyltriphenylamine) (abbreviation: PVTPA) is also usable for the hole transporting layer 7.

However, any substance having a hole transporting performance higher than an electron transporting performance may be used in addition to the above substances. A layer including the highly hole-transporting substance may be provided in the form of a single layer or a laminate of two or more layers.

When the hole transporting layer includes two or more layers, one of the layers with a larger energy gap is preferably provided closer to the emitting layer 5.

Electron Transporting Layer

The electron transporting layer 8 is a layer containing a highly electron-transporting substance. For the electron transporting layer 8, (1) a metal complex such as an aluminum complex, beryllium complex and zinc complex, (2) heteroaromatic compound such as an imidazole derivative, benzimidazole derivative, azine derivative, carbazole derivative, and phenanthroline derivative, and (3) a macromolecular compound are usable. Specifically, as a low-molecule organic compound, a metal complex such as Alq, tris(4-methyl-8-quinolinolato)aluminum (abbreviation: Almq$_3$), bis(10-hydroxybenzo[h]quinolinato)beryllium (abbreviation: BeBq$_2$), BAlq, Znq, ZnPBO and ZnBTZ are usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. In the exemplary embodiments, a benzimidazole compound is suitably usable. The above-described substances mostly have an electron mobility of $10^{-6}$ cm$^2$/(V·s) or more. However, any substance having an electron transporting performance higher than a hole transporting performance may be used for the electron transporting layer 8 in addition to the above substances. The electron transporting layer 8 may be provided in the form of a single layer or a laminate of two or more layers made of the above substance(s).

Moreover, a macromolecular compound is also usable for the electron transporting layer 8. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer 9 is a layer containing a highly electron-injectable substance. Examples of a material for the electron injecting layer 9 include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a substance containing an alkali metal, alkaline earth metal and a compound thereof in the electron-transporting substance, specifically, a substance containing magnesium (Mg) in Alq may be used. In this case, electrons can be more efficiently injected from the cathode 4.

Alternatively, a composite material provided by mixing an organic compound with an electron donor may be used for the electron injecting layer 9. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer 8 (e.g., the metal complex and heteroaromatic compound) is usable. The electron donor may be any substance exhibiting an electron donating performance to the organic compound. Specifically, an alkali metal, an alkaline earth metal or a rare earth metal is preferable, examples of which include lithium, cesium, magnesium, calcium, erbium and ytterbium. Moreover, an alkali metal oxide and alkaline earth metal oxide are preferably used as the electron donor, examples of which include lithium oxide, calcium oxide, and barium oxide. Further, Lewis base such as magnesium oxide is also usable. Furthermore, tetrathiafulvalene (abbreviation: TTF) is also usable.

Cathode

Metal, alloy, an electrically conductive compound, a mixture thereof and the like, which have a small work function, specifically, of 3.8 eV or less, is preferably usable as a material for the cathode 4. Specific examples of the material for the cathode include the elements belonging to Groups 1 and 2 in the periodic table of the elements, a rare-earth metal and an alloy including the elements and/or the rare-earth metal. Examples of the elements belonging to Group 1 in the periodic table of the elements include an alkali metal. Examples of the elements belonging to Group 2 in the periodic table of the elements include an alkaline earth metal. Examples of the alkali metal include lithium (Li) and cesium (Cs). Examples of the alkaline earth metal include magnesium (Mg), calcium (Ca) and strontium (Sr). Examples of the rare earth metal include europium (Eu) and ytterbium (Yb). Examples of the alloy include MgAg and AlLi.

When the cathode 4 is formed of the alkali metal, alkaline earth metal and alloy thereof, vapor deposition or sputtering is usable. Moreover, when the anode 3 is formed of silver paste and the like, coating, ink jet printing and the like are usable.

By providing the electron injecting layer 9, various conductive materials such as Al, Ag, ITO, graphene and indium oxide-tin oxide containing silicon or silicon oxide are usable for forming the cathode 4 irrespective of the magnitude of the work function. The conductive materials can be deposited as a film by sputtering, ink jet printing, spin coating and the like.

Layer Formation Method(s)

A method for forming each layer of the organic EL device 1 in the exemplary embodiment is not limited except for the above particular description. Known methods of dry film-forming and wet film-forming are usable. Examples of the dry film-forming include vacuum deposition, sputtering, plasma deposition method and ion plating. Examples of the wet film-forming include spin coating, dipping, flow coating and ink-jet.

Thickness

A thickness of each of the organic layers in the organic EL device 1 according to the exemplary embodiment is not limited except for the above particular description. In general, the thickness preferably ranges from several nanometers to 1 μm in order to avoid defects such as a pin hole and to prevent efficiency from being deteriorated since a high voltage needs to be applied.

Herein, the numerical range represented with a mark "-" or "to" means a numerical value whose lower limit value is described before the mark "-" or "to" and whose upper limit value is described after the mark "-" or "to".

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not included in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). An atom not forming a ring, and an atom contained in a substituent substituting the ring are not counted in the number of the "ring atoms." Unless specifically described, the same applies to the "ring atoms" described later. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming the substituents are not counted in the number of the ring atoms. When a fluorene ring is substituted by, for instance, a fluorene ring (inclusive of a spirofluorene ring), the number of atoms of the fluorene ring as a substituent is not included in the number of the ring atoms for the fluorene ring.

Next, each of substituents described in the above formulae will be described.

Examples of an aryl group (occasionally referred to as an aromatic hydrocarbon group) having 6 to 30 ring carbon atoms herein include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Herein, unless otherwise specified, the aryl group preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are particularly preferable. A carbon atom in a position 9 of each of 1-fluorenyl group, 2-fluorenyl group, 3-fluorenyl group and 4-fluorenyl group is preferably substituted by at least one group selected from the group consisting of a substituted or unsubstituted alkyl group having 1 to 30 carbon atoms and a substituted or unsubstituted aryl group having 6 to 18 ring carbon atoms described later herein.

The heteroaryl group (occasionally, referred to as a heterocyclic group, heteroaromatic ring group or aromatic heterocyclic group) having 5 to 30 ring atoms herein preferably contains as a hetero atom at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heterocyclic group having 5 to 30 ring atoms in the exemplary embodiment are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Herein, the heterocyclic group preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further preferable. A nitrogen atom in position 9 of 1-carbazolyl group, 2-carbazolyl group, 3-carbazolyl group and 4-carbazolyl group is preferably substituted by at least one group selected from the group consisting of a substituted or unsubstituted aryl group having 6 to 30 ring carbon atoms and a substituted or unsubstituted heterocyclic group having 5 to 30 ring atoms described herein.

Herein, the heterocyclic group may be a group derived from any one of partial structures represented by formulae (XY-1) to (XY-18).

[Formula 60]

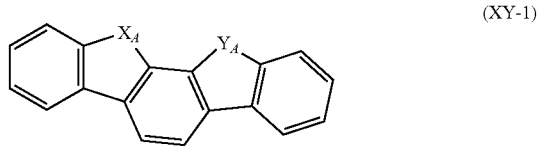

(XY-1)

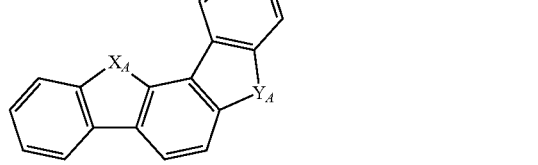

(XY-2)

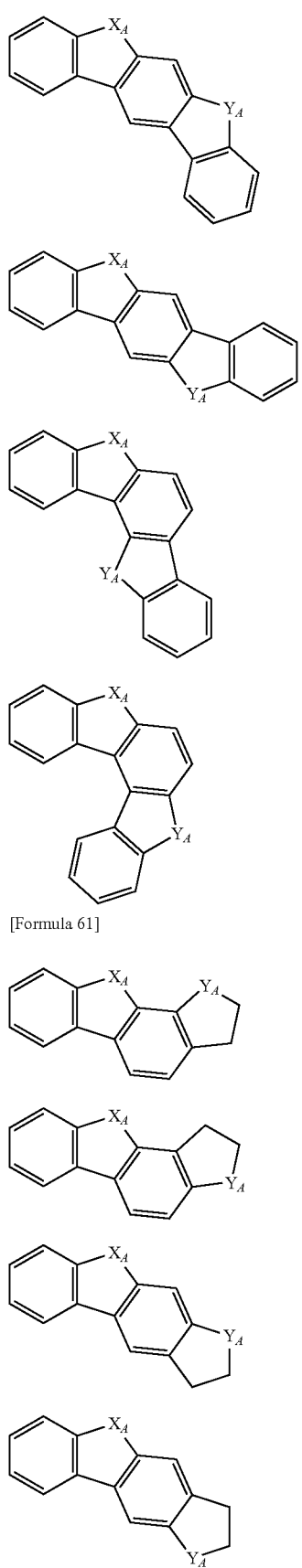
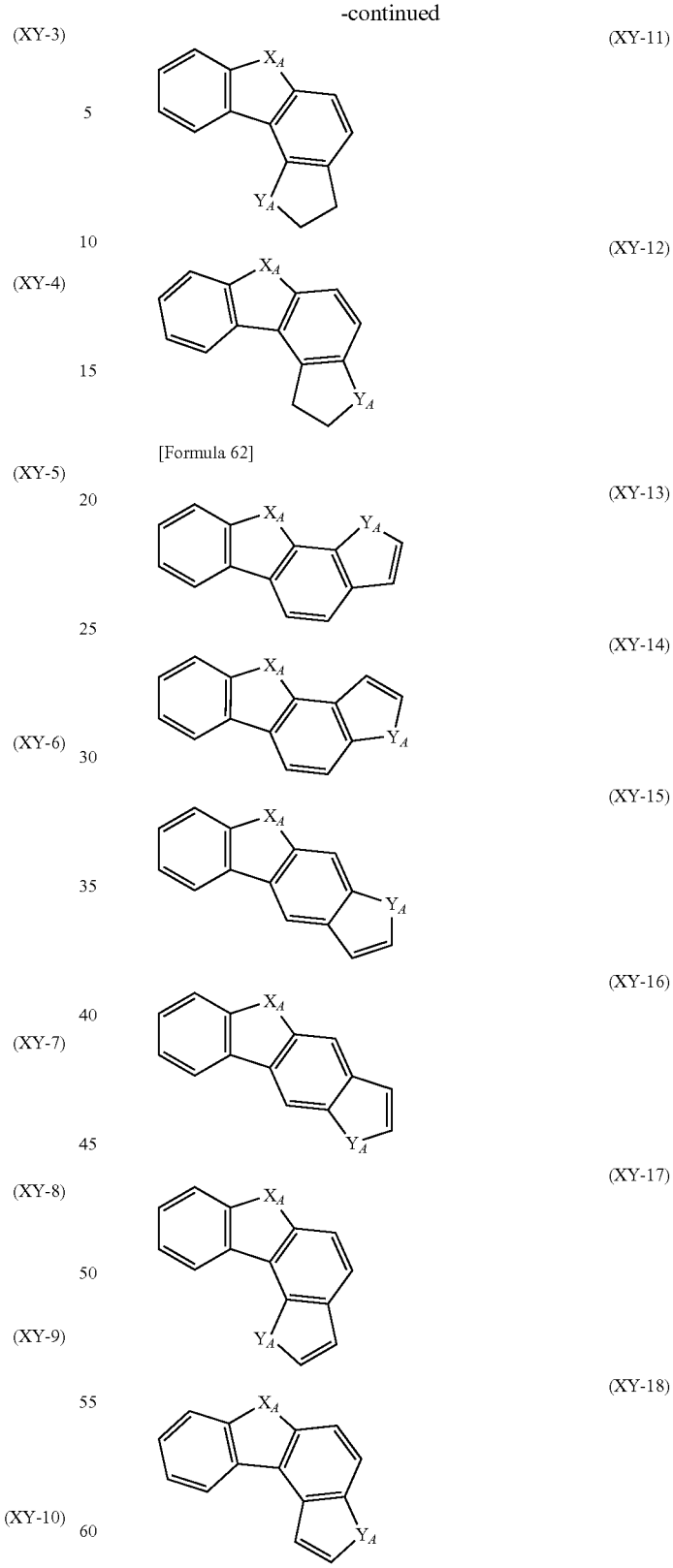
In the formulae (XY-1) to (XY-18), $X_A$ and $Y_A$ each independently represent a hetero atom, and preferably represent an oxygen atom, sulfur atom, selenium atom, silicon atom or germanium atom. The partial structures represented by the formulae (XY-1) to (XY-18) may each be bonded in any position to be a heterocyclic group, which may be substituted.

Herein, examples of the substituted or unsubstituted carbazolyl group may include a group as represented by formulae below in which a carbazole ring is further fused with a ring(s). Such a group also may be substituted. A bonding position is alterable as desired.

[Formula 63]

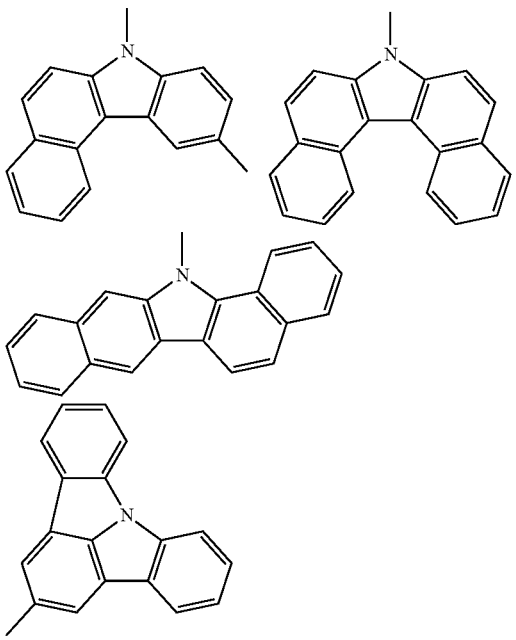

The alkyl group having 1 to 30 carbon atoms herein may be linear, branched or cyclic. Also, the alkyl group may be an alkyl halide group.

Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

Herein, the linear or branched alkyl group preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are preferable.

Herein, examples of the cyclic alkyl group include a cycloalkyl group having 3 to 30 ring carbon atoms.

Examples of the cycloalkyl group having 3 to 30 ring carbon atoms herein are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group or a cyclohexyl group is further preferable.

Herein, the alkyl halide group provided by substituting the alkyl group with a halogen atom is exemplified by an alkyl halide group provided by substituting the alkyl group having 1 to 30 carbon atoms with at least one halogen atom, preferably at least one fluorine atom.

Herein, examples of the alkyl halide group having 1 to 30 carbon atoms include a fluoromethyl group, difluoromethyl group, trifluoromethyl group, fluoroethyl group, trifluoromethylmethyl group, trifluoroethyl group, and pentafluoroethyl group.

Herein, examples of a substituted silyl group include an alkylsilyl group having 3 to 30 carbon atoms and an arylsilyl group having 6 to 30 ring carbon atoms.

Herein, the alkylsilyl group having 3 to 30 carbon atoms is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be mutually the same or different.

Herein, examples of the arylsilyl group having 6 to 30 ring carbon atoms include a dialkylarylsilyl group, alkyldiarylsilyl group and triarylsilyl group.

The dialkylarylsilyl group is exemplified by a dialkylarylsilyl group including two of the examples of the alkyl group having 1 to 30 carbon atoms and one of the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the examples of the alkyl group having 1 to 30 carbon atoms and two of the examples of the aryl group having 6 to 30 ring carbon atoms. The alkyldiarylsilyl group preferably has 13 to 30 carbon atoms.

The triarylsilyl group is exemplified by a triarylsilyl group including three of the examples of the aryl group having 6 to 30 ring carbon atoms. The triarylsilyl group preferably has 18 to 30 carbon atoms.

Herein, an aryl group in an aralkyl group (occasionally referred to as an arylalkyl group) is an aromatic hydrocarbon group or a heterocyclic group.

The aralkyl group having 7 to 30 carbon atoms herein is preferably a group having an aryl group having 6 to 30 ring carbon atoms and is represented by —$Z_3$—$Z_4$. $Z_3$ is exemplified by an alkylene group derived from the above alkyl group having 1 to 30 carbon atoms. $Z_4$ is exemplified by the above aryl group having 6 to 30 ring carbon atoms. In this aralkyl group, an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Herein, the substituted phosphoryl group is represented by a formula (P) below.

[Formula 64]

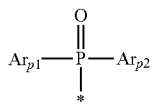

(P)

In the formula (P), $Ar_{P1}$ and $Ar_{P2}$ are each independently a substituent, preferably a substituent selected from the group consisting of an alkyl group having 1 to 30 carbon atoms and an aryl group having 6 to 30 ring carbon atoms, more preferably a substituent selected from the group consisting of an alkyl group having 1 to 10 carbon atoms and an aryl group having 6 to 20 ring carbon atoms, further preferably a substituent selected from the group consisting of an alkyl group having 1 to 6 carbon atoms and an aryl group having 6 to 14 ring carbon atoms.

The alkoxy group having 1 to 30 carbon atoms herein is represented by $-OZ_1$. $Z_1$ is exemplified by the above alkyl group having 1 to 30 carbon atoms. Examples of the alkoxy group include a methoxy group, ethoxy group, propoxy group, butoxy group, pentyloxy group and hexyloxy group. The alkoxy group preferably has 1 to 20 carbon atoms.

A halogenated alkoxy group provided by substituting the alkoxy group with a halogen atom is exemplified by a halogenated alkoxy group provided by substituting the alkoxy group having 1 to 30 carbon atoms with one or more fluorine groups.

Herein, examples of an aryl group in an aryloxy group (occasionally referred to as an arylalkoxy group) include a heteroaryl group.

The arylalkoxy group having 6 to 30 ring carbon atoms herein is represented by $-OZ_2$. $Z_2$ is exemplified by the above aryl group having 6 to 30 ring carbon atoms. The arylalkoxy group preferably has 6 to 20 ring carbon atoms. The arylalkoxy group is exemplified by a phenoxy group.

Herein, the substituted amino group is represented by $-NHR_V$ or $-N(R_V)_2$. $R_V$ is exemplified by the above alkyl group having 1 to 30 carbon atoms or aryl group having 6 to 30 ring carbon atoms.

Herein, the alkenyl group having 2 to 30 carbon atoms is linear or branched. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

Herein, the substituted phosphanyl group is exemplified by a phenyl phosphanyl group.

Herein, the arylcarbonyl group having 6 to 30 ring carbon atoms is represented by $-COY'$. $Y'$ is exemplified by the above aryl group.

Herein, examples of the arylcarbonyl group having 6 to 30 ring carbon atoms include a phenyl carbonyl group, diphenyl carbonyl group, naphthyl carbonyl group, and triphenyl carbonyl group.

Herein, the alkylthio group having 1 to 30 carbon atoms and the arylthio group having 6 to 30 ring carbon atoms are represented by $-SR_V$. $R_V$ is exemplified by the above alkyl group having 1 to 30 carbon atoms or aryl group having 6 to 30 ring carbon atoms. The alkylthio group preferably has 1 to 20 carbon atoms. The arylthio group preferably has 6 to 20 ring carbon atoms.

Herein, examples of the halogen atom include a fluorine atom, a chlorine atom, a bromine atom and an iodine atom, among which a fluorine atom is preferable.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

Herein, the substituent meant by "substituted or unsubstituted" is at least one group selected from the group consisting of an alkynyl group having 2 to 30 carbon atoms, cyano group, hydroxyl group, nitro group, and carboxy group in addition to an aryl group having 6 to 30 ring carbon atoms, heteroaryl group having 5 to 30 ring atoms, alkyl group (linear or branched alkyl group) having 1 to 30 carbon atoms, cycloalkyl group having 3 to 30 ring carbon atoms, alkyl halide group having 1 to 30 carbon atoms, alkylsilyl group having 3 to 30 carbon atoms, arylsilyl group having 6 to 30 ring carbon atoms, alkoxy group having 1 to 30 carbon atoms, aryloxy group having 6 to 30 ring carbon atoms, substituted amino group, alkylthio group having 1 to 30 carbon atoms, arylthio group having 6 to 30 ring carbon atoms, aralkyl group having 7 to 30 carbon atoms, alkenyl group (linear or branched alkenyl group) having 2 to 30 carbon atoms, and halogen atom.

Herein, the substituent meant by "substituted or unsubstituted" is preferably at least one group selected from the group consisting of an aryl group having 6 to 30 ring carbon atoms, heteroaryl group having 5 to 30 ring atoms, alkyl group (linear or branched alkyl group) having 1 to 30 carbon atoms, halogen atom, and cyano group, further preferably the specific preferable examples described in each of the substituents.

Herein, the substituent meant by "substituted or unsubstituted" may be further substituted by at least one group selected from the group consisting of an aryl group having 6 to 30 ring carbon atoms, heteroaryl group having 5 to 30 ring atoms, alkyl group (linear or branched alkyl group) having 1 to 30 carbon atoms, cycloalkyl group having 3 to 30 ring carbon atoms, alkyl halide group having 1 to 30 carbon atoms, alkylsilyl group having 3 to 30 carbon atoms, arylsilyl group having 6 to 30 ring carbon atoms, alkoxy group having 1 to 30 carbon atoms, aryloxy group having 6 to 30 carbon atoms, substituted amino group, alkylthio group having 1 to 30 carbon atoms, arylthio group having 6 to 30 ring carbon atoms, aralkyl group having 7 to 30 carbon atoms, alkenyl group having 2 to 30 carbon atoms, an alkynyl group having 2 to 30 carbon atoms, halogen atom, cyano group, hydroxyl group, nitro group, and carboxy group. In addition, a plurality of ones of the substituent may be mutually bonded to form a ring.

Herein, the substituent further substituting for the substituent meant by "substituted or unsubstituted" is preferably at least one group selected from the group consisting of an aryl group having 6 to 30 ring carbon atoms, heteroaryl group having 5 to 30 ring atoms, alkyl group (linear or branched alkyl group) having 1 to 30 carbon atoms, halogen atom, and cyano group, and is further preferably at least one group selected from the specific preferable examples described in each of the substituents.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group.

Herein, "XX to YY atoms" in the description of "substituted or unsubstituted ZZ group having XX to YY atoms" represent atoms of an unsubstituted ZZ group and does not include atoms of a substituent(s) of the substituted ZZ group.

The same description as the above applies to "substituted or unsubstituted" in compounds or partial structures thereof described herein.

Herein, when the substituents are bonded to each other to form a ring, the ring is structured to be a saturated ring, an unsaturated ring, an aromatic hydrocarbon ring or a hetero ring.

Herein, examples of the aromatic hydrocarbon group and the heterocyclic group in the linking group include a divalent or multivalent group obtained by eliminating one or more atoms from the above monovalent groups.

The organic EL device according to the exemplary embodiment can improve a luminous efficiency.

Electronic Device

An electronic device of the exemplary embodiment includes the organic EL device of the exemplary embodiment. Examples of the electronic device include a display device and light-emitting device. Examples of the display device include a display component (e.g., en organic EL panel module), TV, mobile phone, tablet and personal computer. Examples of the light-emitting device include an illuminator and a vehicle light.

Second Exemplary Embodiment

An arrangement of an organic EL device according to a second exemplary embodiment will be described. In the description of the second exemplary embodiment, the same components as those in the first exemplary embodiment are denoted by the same reference signs and names to simplify or omit an explanation of the components. In the second exemplary embodiment, any materials and compounds that are not specified may be the same as those in the first exemplary embodiment.

The organic EL device according to the second exemplary embodiment is different from the organic EL device according to the first exemplary embodiment in that the emitting layer further includes a second compound. The emitting layer of the organic EL device of the second exemplary embodiment contains the first compound, the second compound and the fluorescent compound.

The rest of the arrangement of the organic EL device according to the second exemplary embodiment is the same as in the first exemplary embodiment.

The emitting layer of the organic EL device of the second exemplary embodiment may contain a metal complex, however, a heavy metal complex is preferably not contained in the emitting layer.

The emitting layer of the organic EL device of the second exemplary embodiment preferably does not contain a phosphorescent metal complex.

First Compound

The same compound as described in the first exemplary embodiment is usable as the first compound in the second exemplary embodiment.

The first compound of the second exemplary embodiment is preferably the compound represented by the formula (10B), more preferably the compound represented by the formula (12a), further preferably the compound represented by the formula (13b), (14a) or (16a), furthermore preferably the compound represented by the formula (13e), (13f), (14c) or (16c), still further preferably the compound represented by the formula (13e).

Second Compound

A singlet energy $S_1(M2)$ of the second compound and the singlet energy $S_1(M1)$ of the first compound satisfy a relationship of Numerical Formula 2 below.

$$S_1(M2) > S_1(M1)) \quad \text{(Numerical Formula 2)}.$$

The second compound may be a thermally activated delayed fluorescent compound or a compound exhibiting no thermally activated delayed fluorescence.

The second compound is also preferably a host material (occasionally referred to as a matrix material). When the first compound and the second compound are the host materials, for instance, one of the compounds may be referred to as a first host material and the other may be referred to as a second host material.

Although the second compound is not particularly limited, the second compound is preferably a compound other than an amine compound. Although the second compound may be a derivative selected from the group consisting of a carbazole derivative, dibenzofuran derivative, and dibenzothiophene derivative, the second compound is not limited thereto.

It is also preferable that the second compound has at least one of a partial structure represented by a formula (31), a partial structure represented by a formula (32), a partial structure represented by a formula (33) and a partial structure represented by a formula (34) in one molecule.

[Formula 65]

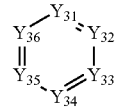

(31)

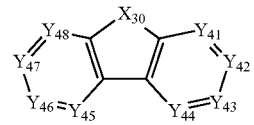

(32)

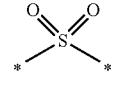

(33)

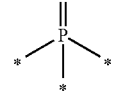

(34)

In the formula (31), $Y_{31}$ to $Y_{36}$ each independently represent a nitrogen atom or a carbon atom bonded to another atom in the molecule of the second compound.

At least one of $Y_{31}$ to $Y_3$ is a carbon atom bonded to another atom in the molecule of the second compound.

In the formula (32), $Y_{41}$ to $Y_{45}$ each independently represent a nitrogen atom or a carbon atom bonded to another atom in the molecule of the second compound.

At least one of $Y_{41}$ to $Y_{48}$ is a carbon atom bonded to another atom in the molecule of the second compound.

$X_{30}$ represents a nitrogen atom bonded to another atom in the molecule of the second compound, an oxygen atom, or a sulfur atom.

The mark * in the formulae (33) to (34) each independently shows a bonding position with another atom or another structure in the molecule of the second compound.

In the formula (32), it is also preferable that at least two of $Y_{41}$ to $Y_{45}$ are carbon atoms bonded to other atoms in the molecule of the second compound to form a cyclic structure including the carbon atoms.

For instance, the partial structure represented by the formula (32) is preferably any one selected from the group consisting of partial structures represented by formulae (321), (322), (323), (324), (325) and (326).

[Formula 66]

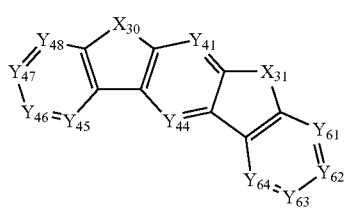
(321)

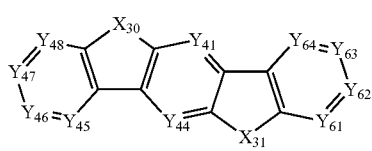
(322)

[Formula 67]

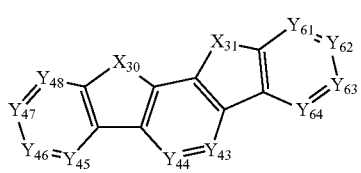
(323)

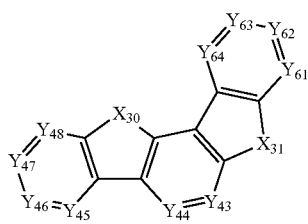
(324)

[Formula 68]

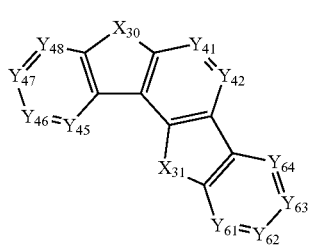
(325)

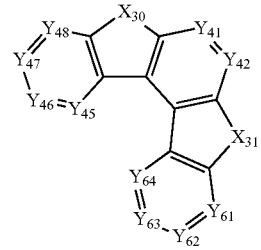
(326)

In the formulae (321) to (326), $X_{30}$ each independently represents a nitrogen atom bonded to another atom in the molecule of the second compound, an oxygen atom, or a sulfur atom.

$Y_{41}$ to $Y_{48}$ each independently represent a nitrogen atom or a carbon atom bonded to another atom in the molecule of the second compound.

$X_{31}$ each independently represents a nitrogen atom bonded to another atom in the molecule of the second compound, an oxygen atom, a sulfur atom, or a carbon atom bonded to another atom in the molecule of the second compound.

$Y_{61}$ to $Y_{64}$ each independently represent a nitrogen atom or a carbon atom bonded to another atom in the molecule of the second compound.

In the second exemplary embodiments, the second compound preferably has the partial structure represented by the formula (323) among those represented by the formulae (323) to (326).

The partial structure represented by the formula (31) is preferably included in the second compound as at least one group selected from the group consisting of a group represented by a formula (33) and a group represented by a formula (34).

It is also preferable that the second compound has at least one of the partial structures represented by the formulae (33) and (34). Since bonding positions are situated in meta positions as shown in the partial structures represented by the formulae (33) and (34), an energy gap $T_{77K}(M2)$ at 77 [K] of the second compound can be kept high.

[Formula 69]

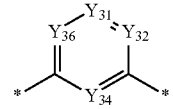
(33)

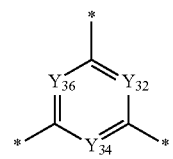
(34)

In the formula (33), $Y_{31}$, $Y_{32}$, $Y_{34}$ and $Y_{36}$ are each independently a nitrogen atom or $CR_{31}$.

In the formula (34), $Y_{32}$, $Y_{34}$ and $Y_{36}$ are each independently a nitrogen atom or $CR_{31}$.

In the formulae (33) and (34), $R_{31}$ each independently represents a hydrogen atom or a substituent.

$R_{31}$ as the substituent is each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

The substituted or unsubstituted aryl group having 6 to 30 ring carbon atoms in $R_{31}$ is preferably a non-fused ring.

The mark * in the formulae (33) and (34) each independently shows a bonding position with another atom or another structure in the molecule of the second compound.

In the formula (33), $Y_{31}$, $Y_{32}$, $Y_{34}$ and $Y_{36}$ are each independently preferably $CR_{31}$, in which a plurality of $R_{31}$ are the same or different.

In the formula (34), $Y_{32}$, $Y_{34}$ and $Y_{36}$ are each independently preferably $CR_{31}$, in which a plurality of $R_{31}$ are the same or different.

The substituted germanium group is preferably represented by $-Ge(R_{301})_3$. $R_{301}$ is each independently a substituent. The substituent $R_{301}$ is preferably a substituted or unsubstituted alkyl group having 1 to 30 carbon atoms or a substituted or unsubstituted aryl group having 6 to 30 ring carbon atoms. A plurality of $R_{301}$ are mutually the same or different.

The partial structure represented by the formula (32) is preferably included in the second compound as at least one group selected from the group consisting of groups represented by formulae (35) to (39) and a group represented by a formula (30a).

[Formula 70]

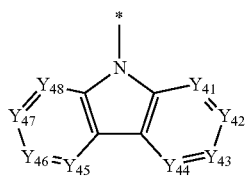

(35)

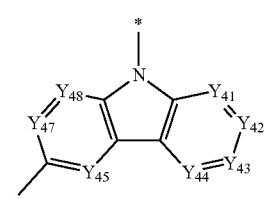

(36)

[Formula 71]

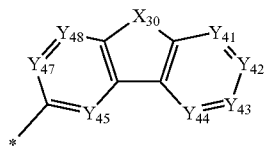

(37)

-continued

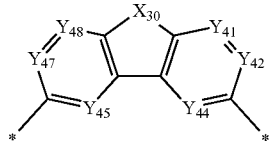

(38)

[Formula 72]

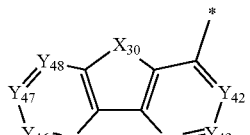

(39)

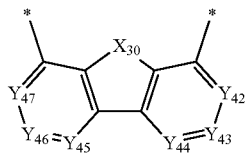

(30a)

In the formula (35), $Y_{41}$ to $Y_{48}$ are each independently a nitrogen atom or $CR_{32}$.

In the formulae (36) and (37), $Y_{41}$ to $Y_{45}$, $Y_{47}$ and $Y_{48}$ are each independently a nitrogen atom or $CR_{32}$.

In the formula (38), $Y_{41}$, $Y_{42}$, $Y_{44}$, $Y_{45}$, $Y_{47}$ and $Y_{48}$ are each independently a nitrogen atom or $CR_{32}$.

In the formula (39), $Y_{42}$ to $Y_{48}$ are each independently a nitrogen atom or $CR_{32}$.

In the formula (30a), $Y_{42}$ to $Y_{47}$ are each independently a nitrogen atom or $CR_{32}$.

In the formulae (35) to (39) and (30a), $R_{32}$ each independently represents a hydrogen atom or a substituent.

$R_{32}$ as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

A plurality of $R_{32}$ are mutually the same or different.

In the formulae (37) to (39) and (30a), $X_{30}$ represents $NR_{33}$, an oxygen atom or a sulfur atom.

$R_{33}$ is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a fluorine atom, a cyano group, a nitro group, and a substituted or unsubstituted carboxy group.

A plurality of $R_{33}$ are mutually the same or different.

The substituted or unsubstituted aryl group having 6 to 30 ring carbon atoms in $R_{33}$ is preferably a non-fused ring.

The mark * in the formulae (35) to (39) and (30a) each independently shows a bonding position with another atom or another structure in the molecule of the second compound.

In the formula (35), $Y_{41}$ to $Y_{45}$ are each independently preferably $CR_{32}$.

In the formulae (36) and (37), $Y_{41}$ to $Y_{45}$, $Y_{47}$ and $Y_{45}$ are each independently preferably $CR_{32}$.

In the formula (38), $Y_{41}$, $Y_{42}$, $Y_{44}$, $Y_{45}$, $Y_{47}$ and $Y_4$ are each independently preferably $CR_{32}$.

In the formula (39), $Y_{42}$ to $Y_4$ are each independently preferably $CR_{32}$.

In the formula (30a), $Y_{42}$ to $Y_{47}$ are each independently preferably $CR_{32}$. A plurality of $R_{32}$ may be the same or different.

In the second compound, $X_{30}$ is preferably an oxygen atom or a sulfur atom, more preferably an oxygen atom.

In the second compound, $R_{31}$ and $R_{32}$ each independently represent a hydrogen atom or a substituent. $R_{31}$ and $R_{32}$ as the substituents are preferably each independently a group selected from the group consisting of a fluorine atom, a cyano group, a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms. $R_{31}$ and $R_{32}$ are more preferably a hydrogen atom, a cyano group, a substituted or unsubstituted aryl group having 6 to 30 ring carbon atoms, or a substituted or unsubstituted heteroaryl group having 5 to 30 ring atoms. When $R_{31}$ and $R_{32}$ as the substituents are each a substituted or unsubstituted aryl group having 6 to 30 ring carbon atoms, the aryl group is preferably a non-fused ring.

It is also preferable that the second compound is an aromatic hydrocarbon compound or an aromatic heterocyclic compound. Moreover, it is preferable that the second compound does not have a fused aromatic hydrocarbon ring.

Manufacturing Method of Second Compound

The second compound can be manufactured by methods disclosed in International Publication No. WO2012/153780, International Publication No. WO2013/038650, and the like. Furthermore, the second compound can be manufactured, for instance, by application of known substitution reactions and/or materials depending on a target compound.

Examples of the substituent in the second compound are shown below, but the invention is not limited thereto.

Specific examples of the aryl group (occasionally referred to as an aromatic hydrocarbonl group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the aryl group having a substituent include a tolyl group, xylyl group and 9,9-dimethylfluorenyl group.

As is understood from the specific examples, the aryl group includes both fused aryl group and non-fused aryl group.

Preferable examples of the aryl group include a phenyl group, biphenyl group, terphenyl group, quarterphenyl group, naphthyl group, triphenylenyl group and fluorenyl group.

Specific examples of the heteroaryl group (occasionally referred to as a heterocyclic group, heteroaromatic ring group or aromatic heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothienyl group, dibenzothienyl group, azadibenzothienyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothienyl group, carbazolyl group, pyridyl group, pyrimidinyl group, triazinyl group, azadibenzofuranyl group and azadibenzothienyl group may be preferable.

The heteroaryl group is preferably a dibenzofuranyl group, dibenzothienyl group, carbazolyl group, pyridyl group, pyrimidinyl group, triazinyl group, azadibenzofuranyl group or azadibenzothienyl group, and more preferably a dibenzofuranyl group, dibenzothienyl group, azadibenzofuranyl group and azadibenzothienyl group.

In the second compound, it is also preferable that the substituted silyl group is selected from the group consisting of a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the second compound, it is also preferable that the substituted phosphine oxide group is a substituted or unsubstituted diaryl phosphine oxide group.

Specific examples of the substituted or unsubstituted diaryl phosphine oxide group include a diphenyl phosphine oxide group and ditolyl phosphine oxide group.

In the second compound, the substituted carboxy group is exemplified by a benzoyloxy group.

Relationship Between First Compound, Fluorescent Compound and Second Compound in Emitting Layer The first compound, the fluorescent compound and the second compound in the emitting layer preferably satisfy the relationship of Numerical Formula 1 and the relationship of Numerical Formula 2. In other words, a relationship of the following numerical formula (Numerical Formula 3) is preferably satisfied.

$$S_1(M2) > S_1(M1) > S_1(FL) \quad \text{(Numerical Formula 3)}.$$

An energy gap $T_{77K}(M2)$ at 77 [K] of the second compound is preferably larger than an energy gap $T_{77K}(M1)$ at 77 [K] of the first compound. In other words, a relationship of the following numerical formula (Numerical Formula 5) is preferably satisfied.

$$T_{77K}(M2) > T_{77K}(M1) \qquad \text{(Numerical Formula 5)}.$$

An energy gap $T_{77K}(M2)$ at 77 [K] of the second compound is preferably larger than an energy gap $T_{77K}(FL)$ at 77 [K] of the fluorescent compound. In other words, a relationship of the following numerical formula (Numerical Formula 6) is preferably satisfied.

$$T_{77K}(M2) > T_{77K}(FL) \qquad \text{(Numerical Formula 6)}.$$

The first compound, the fluorescent compound and the second compound in the emitting layer preferably satisfy the relationship of Numerical Formula 4 and the relationship of Numerical Formula 5. In other words, a relationship of the following numerical formula (Numerical Formula 7) is preferably satisfied.

$$T_{77K}(M2) > T_{77K}(M1) > T_{77K}(FL) \qquad \text{(Numerical Formula 7)}.$$

When the organic EL device of the exemplary embodiment emits light, it is preferable that the fluorescent compound in the emitting layer mainly emits light.

Content Ratio of Compounds in Emitting Layer

Content ratios of the respective first compound, fluorescent compound, and second compound in the emitting layer preferably range as follows.

The content ratio of the first compound preferably ranges from 10 mass % to 80 mass %, more preferably from 10 mass % to 60 mass %, further preferably from 20 mass % to 60 mass %.

The content ratio of the fluorescent compound preferably ranges from 0.01 mass % to 10 mass %, more preferably from 0.01 mass % to 5 mass %, further preferably from 0.01 mass % to 1 mass %.

The content ratio of the second compound preferably ranges from 10 mass % to 80 mass %.

An upper limit of the total of the respective content ratios of the first compound, fluorescent compound and second compound in the emitting layer is 100 mass %. It should be noted that the emitting layer of the exemplary embodiment may further contain another material in addition to the first compound, fluorescent compound and second compound.

Figure 5:
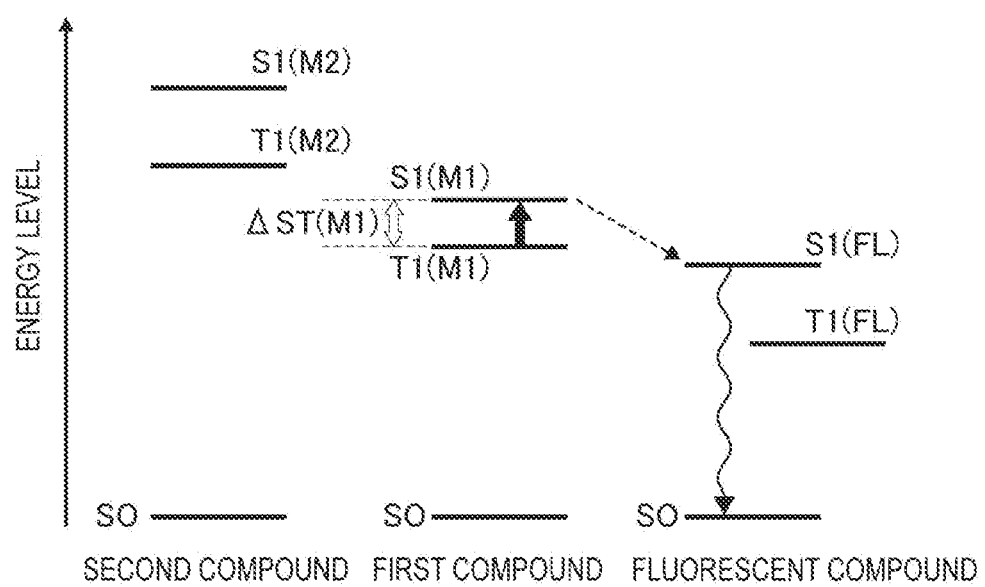
FIG. 5 shows a relationship between energy levels of a first compound, a fluorescent compound and a second compound and an energy transfer between the first compound, the fluorescent compound and the second compound in an emitting layer of an exemplary organic electroluminescence device of a second exemplary embodiment of the invention.

FIG. 5 shows an example of a relationship among energy levels of the first compound, the fluorescent compound and the second compound in the emitting layer. In FIG. 5, S0 represents a ground state. S1(M1) represents the lowest singlet state of the first compound. T1(M1) represents the lowest triplet state of the first compound. S1(FL) represents the lowest singlet state of the fluorescent compound. T1(FL) represents the lowest triplet state of the fluorescent compound. S1(M2) represents the lowest singlet state of the second compound. T1(M2) represents the lowest triplet state of the second compound. A dashed arrow directed from S1(M1) to S1(FL) in FIG. 5 represents Förster energy transfer from the lowest singlet state of the first compound to the lowest singlet state of the fluorescent compound.

As shown in FIG. 5, when a compound having a small ΔST(M1) is used as the first compound, inverse intersystem crossing from the lowest triplet state T1(M1) to the lowest singlet state S1(M1) can be caused by a heat energy. Subsequently, Förster energy transfer from the lowest singlet state S1(M1) of the first compound the fluorescent compound occurs to generate the lowest singlet state S1(FL). Consequently, fluorescence from the lowest singlet state S1(FL) of the fluorescent compound can be observed. It is inferred that the internal quantum efficiency can be theoretically raised up to 100% also by using delayed fluorescence by the TADF mechanism.

The organic EL device according to the exemplary embodiment can improve a luminous efficiency.

The organic EL device of the second exemplary embodiment, in which the emitting layer includes the first compound, the fluorescent compound, and the second compound having the singlet energy larger than that of the first compound, improves the luminous efficiency. It is inferred that an improvement in the luminous efficiency is caused by an improvement in a carrier balance of the emitting layer since the emitting layer contains the second compound.

The organic EL device according to the second exemplary embodiment is applicable to an electronic device such as a display device and a light-emitting device in the same manner as the organic EL device according to the first exemplary embodiment.

Third Exemplary Embodiment

An arrangement of an organic EL device according to a third exemplary embodiment will be described. In the description of the third exemplary embodiment, the same components as those in the first or second exemplary embodiment are denoted by the same reference signs and names to simplify or omit an explanation of the components. In the third exemplary embodiment, any materials and compounds that are not specified may be the same as those in the first or second exemplary embodiment.

The organic EL device according to the third exemplary embodiment is different in the compounds forming the emitting layer from the organic EL devices according to the first and second exemplary embodiment. The rest of the arrangement of the organic EL device according to the third exemplary embodiment is the same as in the first exemplary embodiment.

In the organic EL device of the third exemplary embodiment, the emitting layer contains the first compound and the second compound, the first compound is represented by the formula (1), and the singlet energy $S_1(M2)$ of the second compound is larger than the singlet energy $S_1(M1)$ of the first compound.

The emitting layer of the organic EL device of the third exemplary embodiment may contain a metal complex, however, preferably does not contain a heavy metal complex.

The emitting layer of the organic EL device of the third exemplary embodiment preferably does not contain a phosphorescent metal complex.

The emitting layer in the organic EL device of the third exemplary embodiment, which is different from the emitting layer in the first exemplary embodiment, does not contain a fluorescent compound.

First Compound

The same compound as described in the first exemplary embodiment is usable as the first compound in the third exemplary embodiment.

The first compound of the exemplary embodiment is also preferably a dopant material (occasionally referred to as a guest material, emitter or luminescent material).

The first compound of the third exemplary embodiment is preferably a thermally activated delayed fluorescent compound. Accordingly, in the organic EL device in the third exemplary embodiment, a thermally activated delayed fluorescent compound is preferably selected for use from the first compound of the above exemplary embodiments.

When the organic EL device of the third exemplary embodiment is driven, it is preferable that the first compound in the emitting layer mainly emits light.

The emitting layer in the organic EL device of the third exemplary embodiment preferably does not contain a compound having a singlet energy smaller than the singlet energy $S_1(M1)$ of the first compound.

The first compound of the third exemplary embodiment is preferably the compound represented by the formula (10B), more preferably the compound represented by the formula (12a), further preferably the compound represented by the formula (13b), (14a) or (16a), furthermore preferably the compound represented by the formula (13e), (13f), (14c) or (16c), still further preferably the compound represented by the formula (13e).

The emitting layer in the organic EL device of the third exemplary embodiment preferably further contains a compound having a singlet energy larger than the singlet energy $S_1(M1)$ of the first compound.

As the compound having a singlet energy larger than the singlet energy $S_1(M1)$ of the first compound, the second compound described in the second exemplary embodiment is preferably usable.

Second Compound

The second compound may be a thermally activated delayed fluorescent compound or a compound exhibiting no thermally activated delayed fluorescence.

The second compound is also preferably a host material (occasionally referred to as a matrix material).

It is also preferable in the third exemplary embodiment that the singlet energy $S_1(M1)$ of the first compound and the singlet energy $S_1(M2)$ of the second compound satisfy the relationship of the numerical formula 2.

TADF Mechanism

In the organic EL device in the exemplary embodiment, a compound having a small $\Delta ST(M1)$ is preferably used as the first compound. When $\Delta ST(M1)$ is small, inverse intersystem crossing from a triplet level of the first compound to a singlet level thereof is easily caused by heat energy given from the outside.

Figure 6:
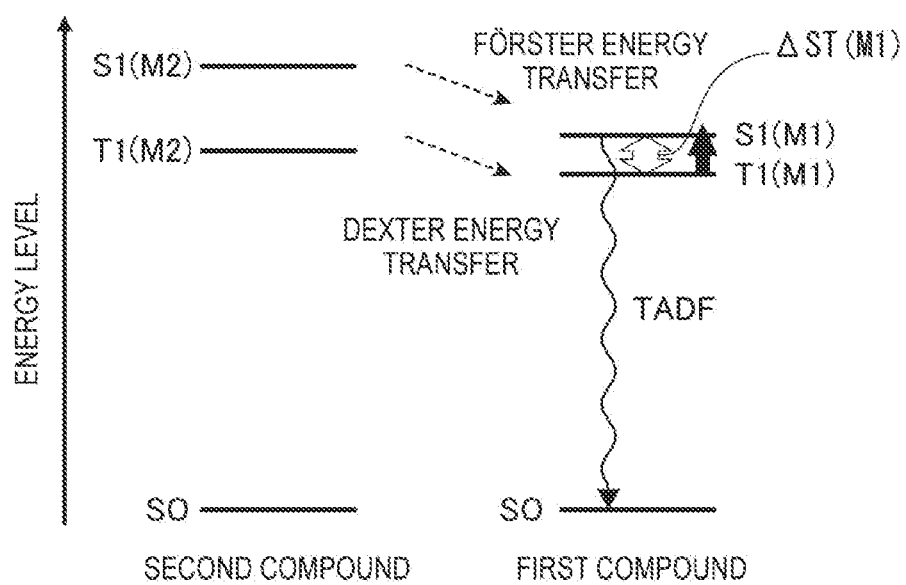
FIG. 6 shows a relationship between energy levels of the first compound and the second compound and an energy transfer between the first compound and the second compound in an emitting layer of an exemplary organic electroluminescence device of a third exemplary embodiment of the invention.

FIG. 6 shows an example of a relationship between energy levels of the first compound and the second compound in the emitting layer. In FIG. 6, S0 represents a ground state, S1(M2) represents a lowest singlet state of the second compound, T1(M2) represents a lowest triplet state of the second compound, S1(M1) represents a lowest singlet state of the first compound, and T1(M1) represents a lowest triplet state of the first compound. A dotted-line arrow shows energy transfer between the excited states in FIG. 6. An energy transfer occurs by Dexter transfer from the lowest triplet state T1(M2) of the second compound to the first compound to generate the lowest singlet state S1(M1) or the lowest triplet state T1(M1). Further, when a material having a small $\Delta ST(M1)$ is used as the first compound, inverse intersystem crossing can be caused by a heat energy from the lowest triplet state T1(M1) to the lowest singlet state S1(M1) in the first compound. As a result, fluorescence from the lowest singlet state S1(M1) of the first compound can be observed. It is inferred that the internal efficiency can be theoretically raised up to 100% also by using delayed fluorescence by the TADF mechanism.

In the exemplary embodiment, an energy gap $T_{77K}(M2)$ at 77 [K] of the second compound is preferably larger than an energy gap $T_{77K}(M1)$ at 77 [K] of the first compound.

Content Ratio of Compounds in Emitting Layer

Content ratios of the respective first and second compounds in the emitting layer preferably range as follows.

The content ratio of the first compound preferably ranges from 1 mass % to 90 mass %, more preferably from 5 mass % to 70 mass %, further preferably from 10 mass % to 50 mass %.

The content ratio of the second compound preferably ranges from 10 mass % to 99 mass %, more preferably from 30 mass % to 95 mass %, further preferably from 50 mass % to 90 mass %.

The organic EL device according to the exemplary embodiment can improve a luminous efficiency.

The organic EL device according to the third exemplary embodiment is applicable to an electronic device such as a display device and a light-emitting device in the same manner as the organic EL device according to the first exemplary embodiment.

Fourth Exemplary Embodiment

The inventors have found that a highly efficient organic EL device is obtainable by containing a compound represented by a formula (11) in an organic EL device.

A compound according to the fourth exemplary embodiment of the invention is the compound represented by the formula (11).

[Formula 73]

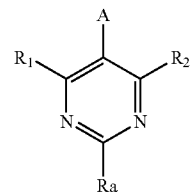

(11)

In the formula (11): Ra represents a hydrogen atom or a substituent. $R_1$ and $R_2$ are each independently a substituent. $R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, and a carboxy group, and a halogen atom. A is the group represented by one of the formulae (1a), (1b) and (1c).

A compound of the fourth exemplary embodiment is preferably represented by a formula (13bx) or (14ax).

[Formula 74]

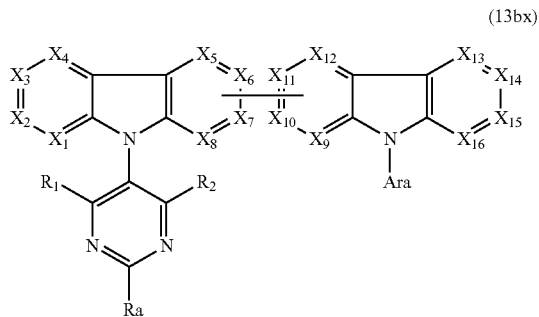

(13bx)

In the formula (13bx), $R_1$ and $R_2$ are each independently a substituent. Ra represents a hydrogen atom or a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_{16}$ each independently represent C—Rb or a nitrogen atom.

In the formula (13bx), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$.

In the formula (13bx), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded. Ara represents the same as the above-described Ara as the substituent.

[Formula 75]

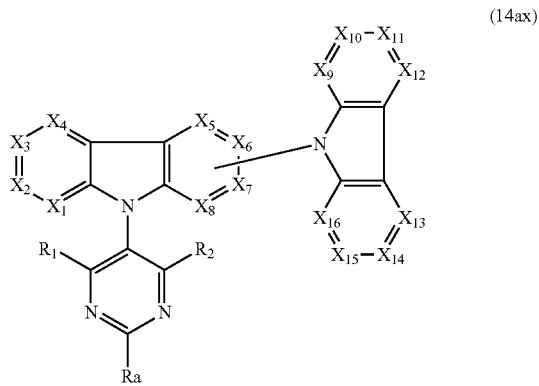

(14ax)

In the formula (14ax), $R_1$, $R_2$ and Ra are each independently a substituent. $R_1$, $R_2$ and Ra as the substituents each independently represent the same as the above-described $R_1$, $R_2$ and Ra as the substituents. At least one of $R_1$ and $R_2$ is a substituent. $X_1$ to $X_1$ each independently represent C—Rb or a nitrogen atom.

In the formula (14ax), at least one of $X_5$ to $X_8$ is a carbon atom bonded to a nitrogen atom in a five-membered ring of a nitrogen-containing fused ring including $X_9$ to $X_{16}$.

In the formula (14ax), Rb each independently represents a hydrogen atom or a substituent. Rb as the substituent represents the same as the above-described Rb as the substituent. A plurality of Rb are mutually the same or different. When a plurality of ones of $X_1$ to $X_8$ are C—Rb and Rb is a substituent, a plurality of Rb are bonded to each other to form a ring, or are not bonded. When a plurality of ones of $X_9$ to $X_{16}$ are C—Rb and Rb is a substituent, a plurality of Rb are bonded to each other to form a ring, or are not bonded.

The compound according to the fourth exemplary embodiment is more preferably represented by the formula (13bx).

In the compound of the exemplary embodiment, A is a group represented by the formula (1b), and at least one of $X_1$ to $X_4$ is C—Rb.

When Rb is a hydrogen atom or a substituent, Rb as the substituent is preferably selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, and a carboxy group, and a halogen atom.

In the compound of the exemplary embodiment, it is more preferable that A is the group represented by the formula (1b), $X_1$, $X_2$, $X_3$, and $X_4$ are C—Rb, and Rb is a hydrogen atom.

In the compound of the exemplary embodiment, it is preferable that $X_1$ to $X_{16}$ are C—Rb, in which a plurality of Rb are mutually the same or different, that, in the formula (1b), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$, and that, in the formula (1c), at least one of $X_5$ to $X_8$ is a carbon atom bonded to a nitrogen atom in a five-membered ring of a nitrogen-containing fused ring including $X_9$ to $X_{16}$.

In the compound of the exemplary embodiment, it is preferable that $X_1$ to $X_{16}$ are C—Rb, Rb each independently represents a hydrogen atom or a substituent, Rb as the substituent is selected from the group consisting of a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms, a plurality of Rb are mutually the same or different, that, in the formula (1b), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$, and that, in the formula (1c), at least one of $X_5$ to $X_8$ is a carbon atom bonded to a nitrogen atom in a five-membered ring of a nitrogen-containing fused ring including $X_9$ to $X_{16}$.

In the compound of the exemplary embodiment, it is preferable that $X_1$ to $X_{16}$ are C—Rb, Rb each independently represents a hydrogen atom or a substituent, Rb as the substituent is selected from the group consisting of a substituted or unsubstituted aryl group having 6 to 30 ring carbon atoms, and a plurality of Rb are mutually the same or different, that, in the formula (1b), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$, and that, in the formula (1c), at least one of $X_5$ to $X_8$ is a carbon atom bonded to a nitrogen atom in a five-membered ring of a nitrogen-containing fused ring including $X_9$ to $X_{16}$.

In the compound of the exemplary embodiment, it is preferable that $X_1$ to $X_{16}$ are C—Rb, Rb is a hydrogen atom, that, in the formula (1b), at least one of $X_5$ to $X_8$ is a carbon atom bonded to one of $X_9$ to $X_{12}$, and at least one of $X_9$ to $X_{12}$ is a carbon atom bonded to one of $X_5$ to $X_8$, and that, in the formula (1c), at least one of $X_5$ to $X_8$ is a carbon atom bonded to a nitrogen atom in a five-membered ring of a nitrogen-containing fused ring including $X_9$ to $X_{16}$.

In the compound of the exemplary embodiment, it is preferable that Ra is a substituent; Ra as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, and a carboxy group, and a halogen atom; and a plurality of Ra are mutually the same or different.

In the compound of the fourth exemplary embodiment, $R_1$, $R_2$ and Ra are preferably substituents at the same time.

In the compound of the fourth exemplary embodiment, $R_1$, $R_2$ and Ra are preferably each independently a substituted or unsubstituted aryl group having 6 to 30 ring carbon atoms.

In the compound of the fourth exemplary embodiment, $R_1$, $R_2$ and Ra are preferably each independently a substituted or unsubstituted phenyl group.

The compound represented by the formula (11) corresponds to a specific compound represented by the formula (1) in which both $R_1$ and $R_2$ are substituents, $Y_1$ and $Y_3$ are nitrogen atoms, and $Y_2$ is C—Ra.

As the compound of the fourth exemplary embodiment, the first compound according to one of the above exemplary embodiments, satisfying the conditions that both $R_1$ and $R_2$ are substituents, $Y_1$ and $Y_3$ are nitrogen atoms, and $Y_2$ is C—Ra, is usable. As the compound of the fourth exemplary embodiment, the first compound according to one of the above exemplary embodiments, satisfying the conditions that both $R_1$ and $R_2$ are substituents, $Y_1$ and $Y_3$ are nitrogen atoms, and $Y_2$ is C—Ra, is usable.

Moreover, among the above-described examples of the first compound in the above exemplary embodiments, a compound satisfying the conditions for the compound of the fourth exemplary embodiment is specifically used as the compound of the fourth exemplary embodiment.

In the compound of the fourth exemplary embodiment, when the plurality of Rb are substituents, it is preferable that the plurality of Rb do not form a ring.

The compound of the fourth exemplary embodiment is preferably the compound represented by the formula (12a) in which both $R_1$ and $R_2$ are substituents.

The compound of the fourth exemplary embodiment is preferably the compound represented by the formula (13bx), (14ax) or (16a), in which both $R_1$ and $R_2$ are substituents.

The compound of the fourth exemplary embodiment is more preferably the compound represented by the formula (13e), (13f), (14c) or (16c), in which both $R_1$ and $R_2$ are substituents.

The compound of the fourth exemplary embodiment is further preferably the compound represented by the formula (13e) in which both $R_1$ and $R_2$ are substituents.

The compound of the fourth exemplary embodiment can improve a luminous efficiency of the organic EL device. For instance, the luminous efficiency of the organic EL device is improvable by containing the compound of the fourth exemplary embodiment in the emitting layer of the organic EL device.

Modification of Exemplary Embodiments

It should be noted that the described exemplary embodiments are to be considered in all respects only as illustrative and not restrictive and various modifications and improvement can be made in the invention as Ion as an object of the invention is achievable.

For instance, in some embodiments, the first compound contained in the emitting layer of the organic EL device in each of the first and second exemplary embodiments is a compound not exhibiting thermally activated delayed fluorescence.

For instance, the emitting layer is not limited to a single layer, but is multi-layered emitting layers in some embodiments. When the organic EL device has a plurality of emitting layers, it is only required that at least one of the emitting layers satisfies the conditions described in the above exemplary embodiments. For instance, in some embodiments, the rest of the emitting layers is a fluorescent emitting layer or a phosphorescent emitting layer using emission by electronic transition from the triplet state directly to the ground state.

Moreover, when the organic EL device has the plurality of emitting layers, in some embodiments, the plurality of emitting layers are adjacent to each other, or provide a so-called tandem-type organic EL device in which a plurality of emitting units are layered through an intermediate layer.

Moreover, for instance, in some embodiments, a blocking layer is adjacent to at least one side of the emitting layer among a side close to the anode and a side close to the cathode. The blocking layer is preferably provided in contact with the emitting layer to block at least one of holes, electrons and excitons.

For instance, when the blocking layer is provided in contact with the side close to the cathode of the emitting layer, the blocking layer permits transport of electrons, but blocks holes from reaching a layer provided close to the cathode (e.g., the electron transporting layer) beyond the blocking layer. When the organic EL device includes an electron transporting layer, the blocking layer is preferably interposed between the emitting layer and the electron transporting layer.

When the blocking layer is provided in contact with the side close to the anode of the emitting layer, the blocking layer permits transport of holes, but blocks electrons from reaching a layer provided close to the anode (e.g., the hole transporting layer) beyond the blocking layer. When the organic EL device includes the hole transporting layer, the blocking layer is preferably interposed between the emitting layer and the hole transporting layer.

Further, the blocking layer may be provided in contact with the emitting layer to prevent an excitation energy from leaking from the emitting layer into neighboring layers. The blocking layer blocks excitons generated in the emitting layer from moving into a layer provided near the electrode (e.g., the electron transporting layer and the hole transporting layer) beyond the blocking layer.

The emitting layer is preferably bonded to the blocking layer.

Specific structure and shape of the components for implementing the invention may be designed in any manner as long as the object of the invention can be achieved.

EXAMPLES

Examples of the invention will be described below. However, it should be noted that the examples are merely illustrative and are not intended to limit the scope of the invention.

Compounds

Compounds used for manufacturing the organic EL device will be shown below.

[Formula 76]

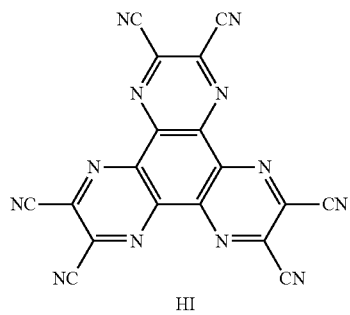

HI

[Formula 77]

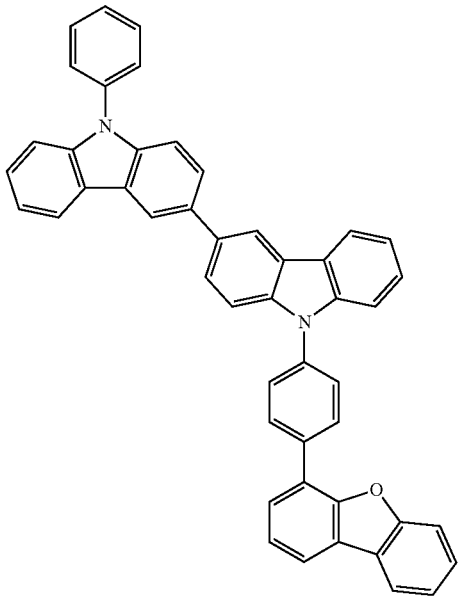

HT2

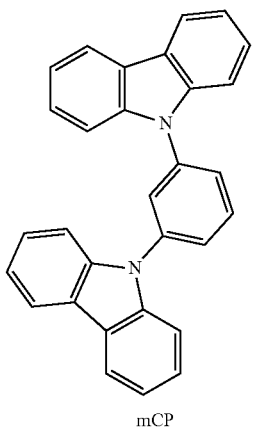

mCP

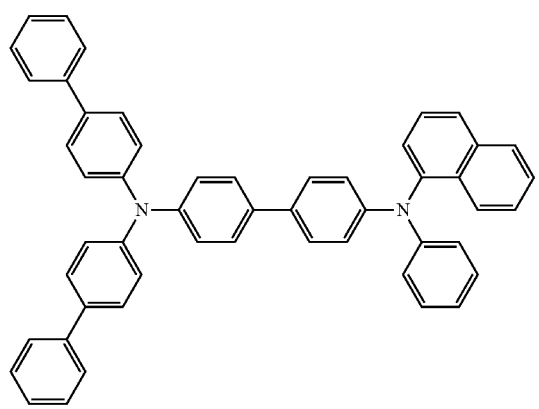

HT1

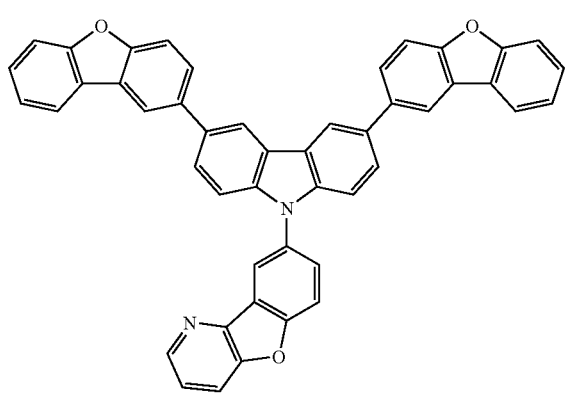

ET1

ET2
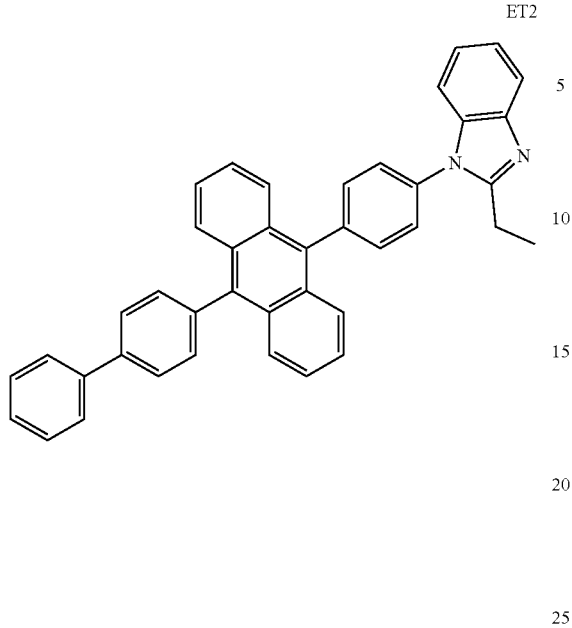
[Formula 79]
TADF3
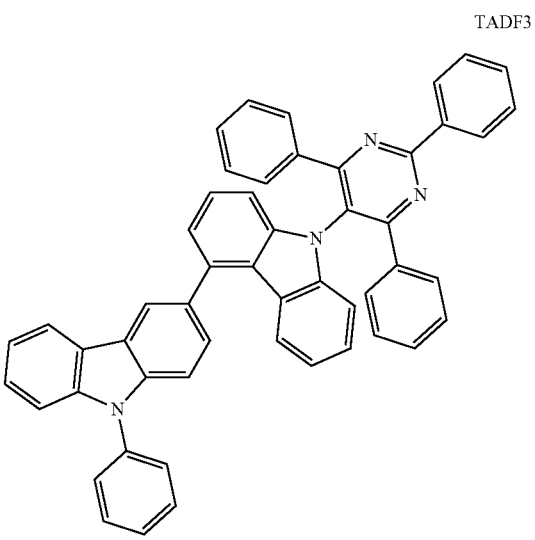
[Formula 78]
TADF1
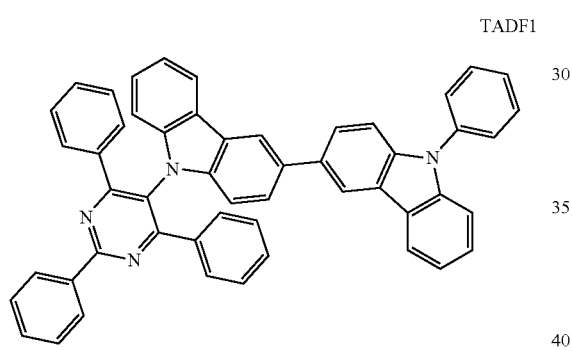
TADF4
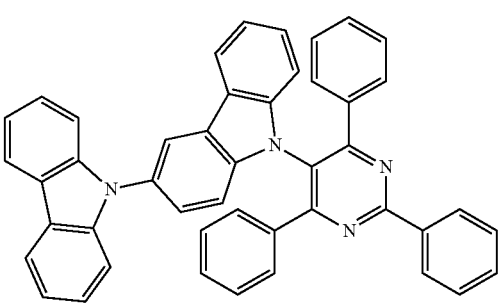
[Formula 80]
H1
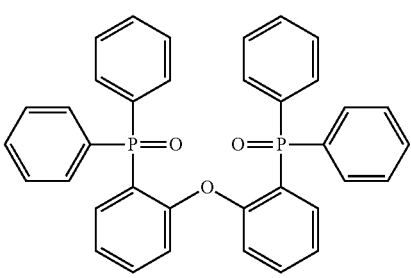
TADF2
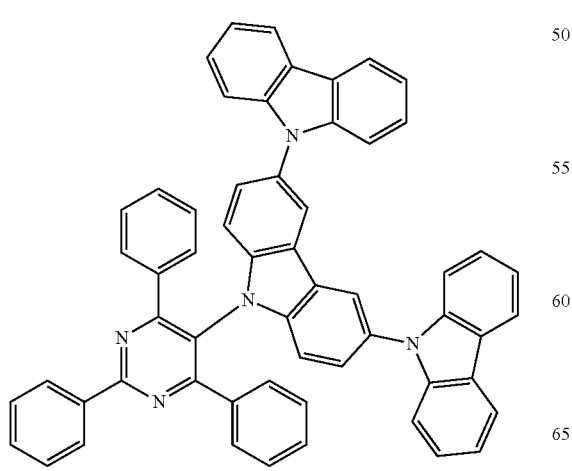
D1
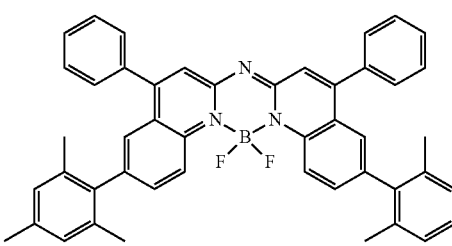

-continued

[Formula 81]

Ref-1

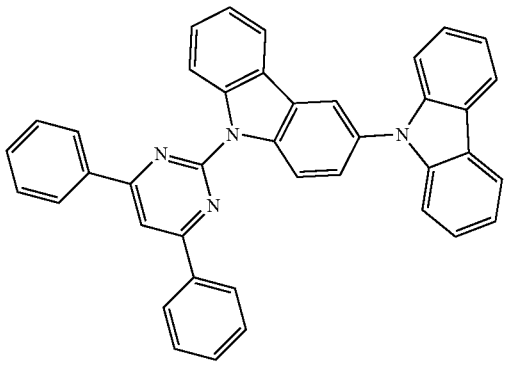

[Formula 82]

Ref-2

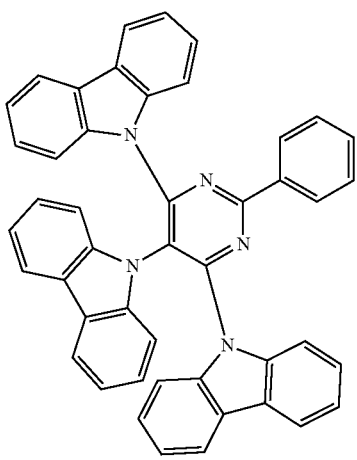

Ref-3

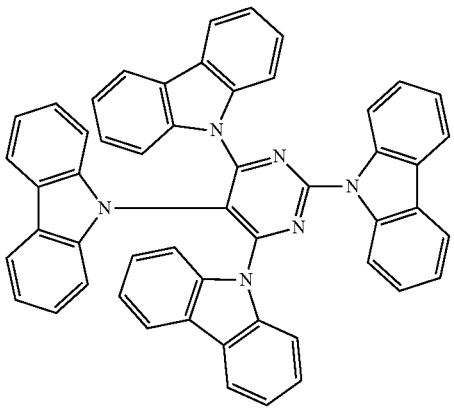

[Formula 83]

Ref-4

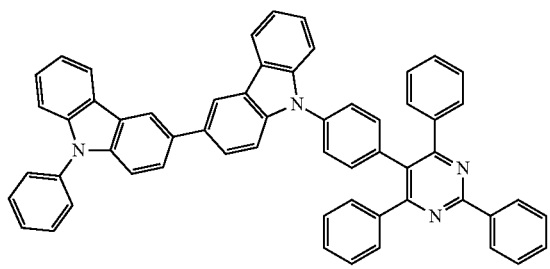

-continued

Ref-5

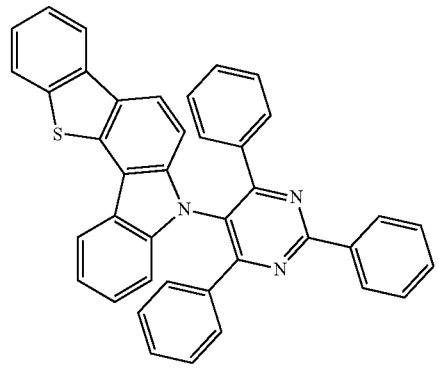

[Formula 84]

Ref-6

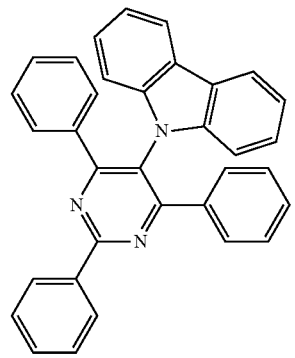

Synthesis of Compound(s)

Synthesis Example 1: Synthesis of Compound TADF1

(1-1) Synthesis of Intermediate (1)

[Formula 85]

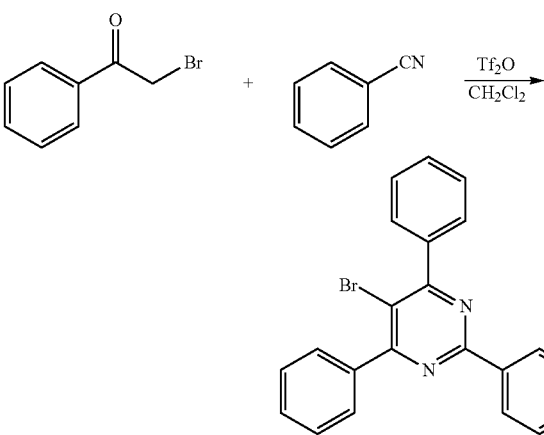

Intermediate (1)

To a three-necked flask, 18.2 g (177 mmol) of benzonitrile, 24.9 g (88 mmol) of trifluoromethanesulfonic anhydride and 100 mL of dehydrated dichloromethane were added and stirred at the room temperature under nitrogen atmosphere. Next, 16.0 g (80 mmol) of phenacyl bromide dissolved in 100 mL of dehydrated dichloromethane was dropped into the flask for one hour. Subsequently, the obtained reaction solution was stirred at the room temperature for 72 hours. 200 mL of dichloromethane was added to the reaction solution. An organic phase was washed with a sodium carbonate aqueous solution until the organic phase became neutral, and dried with anhydrous magnesium sulfate. Subsequently, a solvent was distilled away under reduced pressure. A precipitated solid was suspended in and washed with ethanol to be purified, so that 22.8 g of an intermediate (1) in a form of a white solid was obtained at a yield of 73%.

(1-2) Synthesis of Intermediate (2)

[Formula 86]

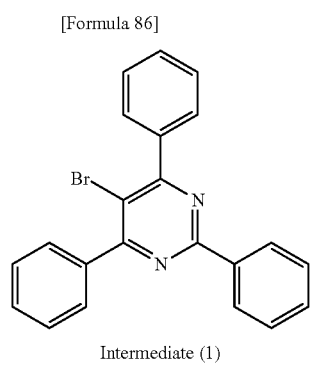

Intermediate (1)

n-BuLi
(PhSO₂)₂NF
───────────→
THF

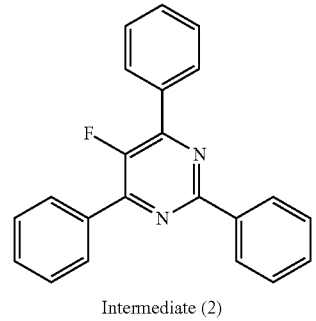

Intermediate (2)

After 10.0 g (25.8 mmol) of the intermediate (1) was put into a four-necked flask, an inside of the flask was purged with nitrogen, to which 350 mL of dehydrated tetrahydrofuran (THF) was added, dissolved and stirred at −65 degrees C. Next, 12 mL of n-butyllithium (2.6M hexane solution) was dropped into the flask and stirred for 30 minutes while keeping −60 degrees C. or less. Subsequently, 16.3 g (51.6 mmol) of N-fluorobenzene sulfonimide dissolved in 70 mL of THF was dropped into the flask. After stirring for one hour at −65 degrees C., the reaction solution was stirred for three hours while the temperature of the reaction solution was gradually returned to the room temperature. After 30 mL of methanol was added to the reaction solution, the reaction solution was condensed under reduced pressure. A precipitated solid was suspended in and washed with ethanol to be purified, so that 5.4 g of an intermediate (2) in a form of a white solid was obtained at a yield of 64%.

(1-3) Synthesis of TADF1

[Formula 87]

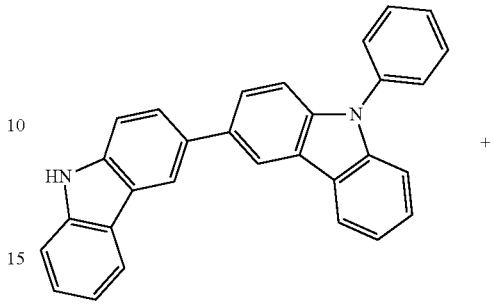

Intermediate (3)

+

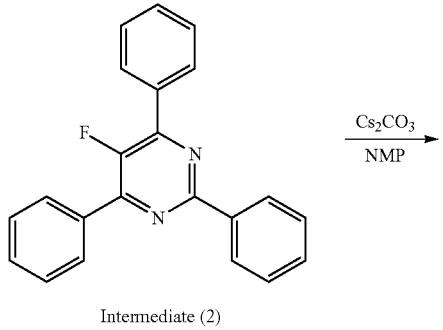

Intermediate (2)

Cs₂CO₃
──────→
NMP

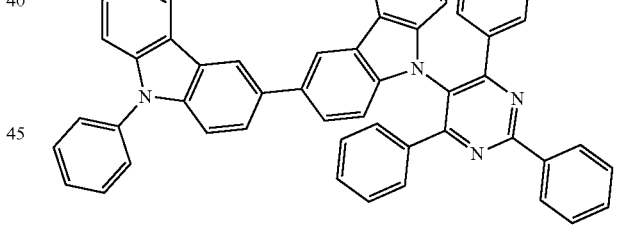

TADF1

To a three-necked flask, 0.45 g (1.1 mmol) of an intermediate (3), 0.3 g (0.92 mmol) of the intermediate (2), 0.92 g (2.8 mmol) of cesium carbonate, and 10 mL of N-methylpyrrolidone (NMP) were added and heated at 160 degrees C. with stirring for two days. The obtained reaction solution was poured into water. A precipitated solid was filtrated. The obtained solid was suspended in and washed with methanol and further suspended in and washed with ethanol to be purified, so that 0.5 g of TADF1 in a form of a white solid was obtained at a yield of 76%. A result of FD-MS (Field Desorption Mass Spectrometry) analysis showed m/e=714 relative to a molecular weight of 714, so that the obtained solid was identified as a target substance.

Synthesis Example 2: Synthesis of Compound TADF2

(2-1) Synthesis of Intermediate (4)

[Formula 88]

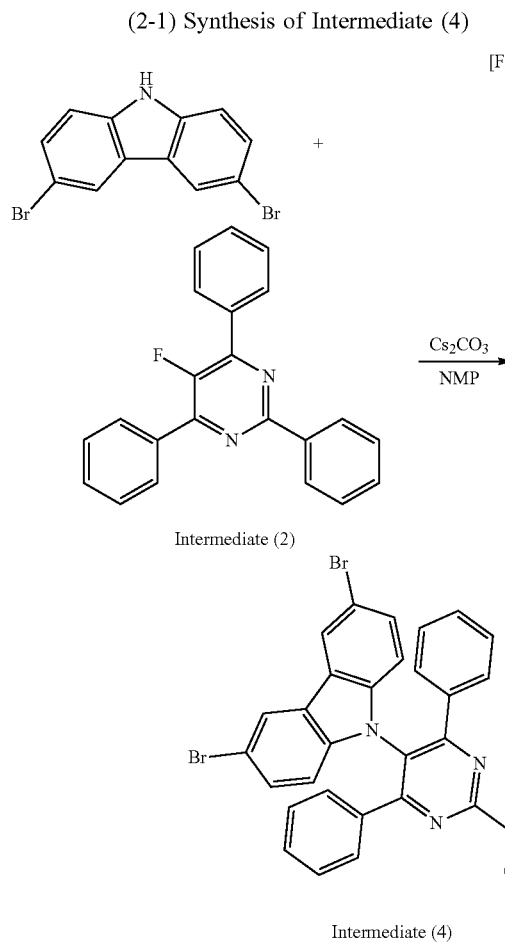

Intermediate (2)

Intermediate (4)

To a three-necked flask, 1.0 g (3.0 mmol) of 3,6-dibromocarbazole, 1.0 g (3.0 mmol) of the intermediate (2), 3.0 g (9.2 mmol) of cesium carbonate, and 15 mL of NMP were added and heated with stirring at 160 degrees C. for eight hours. The obtained reaction solution was poured into water. A precipitated solid was filtered. The obtained solid was suspended in and washed with ethanol to be purified, so that 1.5 g of an intermediate (4) in a form of a white solid was obtained at a yield of 78%.

(2-2) Synthesis of TADF2

[Formula 89]

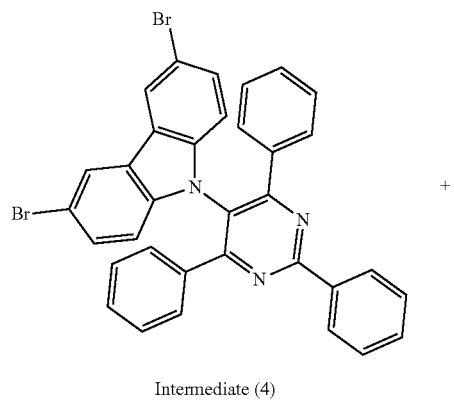

Intermediate (4)

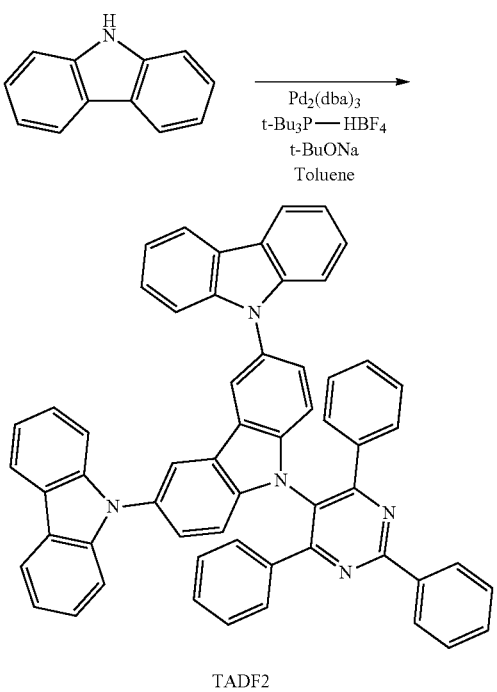

TADF2

To a three-necked flask, under argon atmosphere, 1.5 g (2.4 mmol) of the intermediate (4), 0.87 g (5.2 mmol) of carbazole, 87 mg (0.095 mmol) of $Pd_2(dba)_3$, 0.11 g (0.38 mmol) of $t-Bu_3P-HBF_4$, and 1.1 g (11.4 mmol) of t-BuONa were added, to which 25 mL of toluene was added and heated with stirring at 100 degrees C. for eight hours. 500 mL of toluene was added to the reaction solution. An undissolved substance was filtrated through silica gel. The obtained filtrate was condensed under reduced pressure. The obtained solid was suspended in and washed with ethanol and recrystallized with toluene to be purified, so that 1.2 g of TADF2 in a form of a white solid was obtained at a yield of 62%. A result of FD-MS analysis showed m/e=803 relative to a molecular weight of 803, so that the obtained solid was identified as a target substance.

Synthesis Example 3: Synthesis of Compound TADF3

[Formula 90]

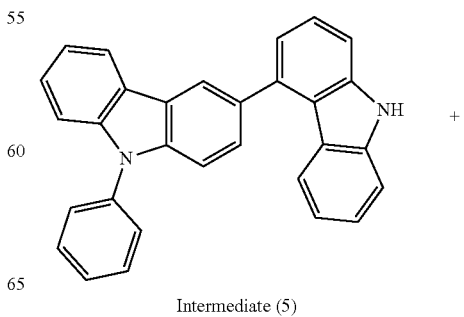

Intermediate (5)

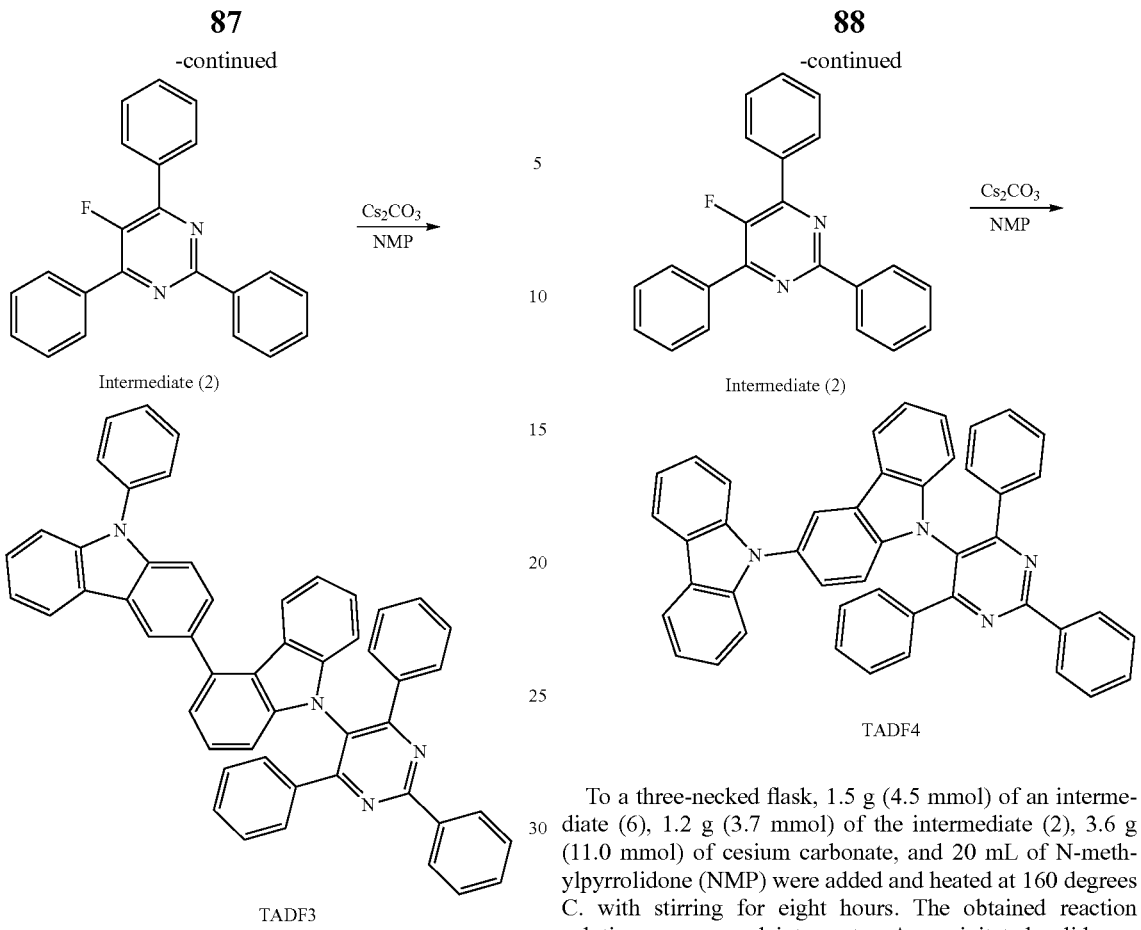

To a three-necked flask, 1.1 g (2.7 mmol) of an intermediate (5), 1.0 g (3.1 mmol) of the intermediate (2), 3.0 g (9.2 mmol) of cesium carbonate, and 15 mL of N-methylpyrrolidone (NMP) were added and heated at 160 degrees C. with stirring for eight hours. The obtained reaction solution was poured into water. A precipitated solid was filtrated. The obtained solid was suspended in and washed with methanol and further suspended in and washed with ethanol to be purified, so that 1.7 g of TADF3 in a form of a white solid was obtained at a yield of 78%. A result of FD-MS analysis showed m/e=714 relative to a molecular weight of 714, so that the obtained solid was identified as a target substance.

Synthesis Example 4: Synthesis of Compound TADF4

[Formula 91]

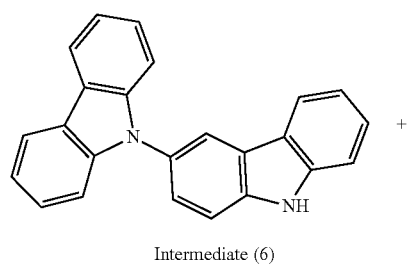

Intermediate (6)

To a three-necked flask, 1.5 g (4.5 mmol) of an intermediate (6), 1.2 g (3.7 mmol) of the intermediate (2), 3.6 g (11.0 mmol) of cesium carbonate, and 20 mL of N-methylpyrrolidone (NMP) were added and heated at 160 degrees C. with stirring for eight hours. The obtained reaction solution was poured into water. A precipitated solid was filtrated. The obtained solid was suspended in and washed with methanol and further suspended in and washed with ethanol to be purified, so that 1.7 g of TADF4 in a form of a white solid was obtained at a yield of 72%. A result of FD-MS analysis showed m/e=638 relative to a molecular weight of 638, so that the obtained solid was identified as a target substance.

Evaluation of Compounds

A method of measuring characteristics of the compounds is shown below.

Thermally Activated Delayed Fluorescence Characteristics

Thermally activated delayed fluorescence characteristics were checked by measuring transient photoluminescence (PL) using a device shown in FIG. 2. A sample was prepared by co-depositing the compounds TADF1 and TH-2 on a quartz substrate at a ratio of the compound TADF1 of 12 mass % to form a 100-nm-thick thin film. Prompt emission was observed immediately when the excited state was achieved by exciting the compound TADF1 with a pulse beam (i.e., a beam emitted from a pulse laser) having a wavelength to be absorbed by the compound TADF1, and Delay emission was observed not immediately when the excited state was achieved but after the excited state was achieved. In Examples, the delayed fluorescence means that a value of XD/XP is 0.05 or more, provided that the amount of Prompt emission is denoted by XP and the amount of Delay emission is denoted by XD.

It was confirmed that the value of XD/XP was 0.05 or more in the compound TADF1.

The amount of Prompt emission and the amount of Delay emission can be obtained according to the method as described in "Nature 492, 234-238, 2012." A device used for calculating the amount of Prompt emission and the amount of Delay emission is not limited to the device described in FIG. 2 and Cited Literatures.

The compounds TADF2, TADF3 and TADF4 were also checked in the same manner as the compound TADF1, so that it was confirmed that the value of XD/XP was 0.05 or more also in the compounds TADF2, TADF3 and TADF4.

Singlet Energy $S_1$

A singlet energy $S_1$ of each of the compounds TADF1, TADF2, TADF3, TADF4, D1, Ref-1, Ref-2, Ref-3, Ref-4, Ref-5, and Ref-6 was measured by the above solution method.

The singlet energy $S_1$ of the compound TADF1 was 3.0 eV.
The singlet energy $S_1$ of the compound TADF2 was 3.1 eV.
The singlet energy $S_1$ of the compound TADF3 was 3.1 eV.
The singlet energy $S_1$ of the compound TADF4 was 3.1 eV.
The singlet energy $S_1$ of the compound D1 was 2.7 eV.
The singlet energy $S_1$ of the compound Ref-1 was 3.2 eV.
The singlet energy $S_1$ of the compound Ref-2 was 3.1 eV.
The singlet energy $S_1$ of the compound Ref-3 was 3.1 eV.
The singlet energy $S_1$ of the compound Ref-4 was 3.3 eV.
The singlet energy $S_1$ of the compound Ref-5 was 3.1 eV.
The singlet energy $S_1$ of the compound Ref-6 was 3.1 eV.

A singlet energy of a compound H1 is 4.0 eV as described in a literature (APPLIED PHYSICS LETTERS 101, 093306 (2012)).

Energy Gap at 77 [K]

An energy gap $T_{77K}$ at 77 [K] of each of the compounds TADF1, TADF2, TADF3, TADF4, and D1 was measured by the above method.

$T_{77K}$ of the compound TADF1 was 2.8 eV.
$T_{77K}$ of the compound TADF2 was 2.8 eV.
$T_{77K}$ of the compound TADF3 was 2.8 eV.
$T_{77K}$ of the compound TADF4 was 2.8 eV.
$T_{77K}$ of the compound D1 was 2.5 eV.

Main Peak Wavelength of Compounds

A 5-μmol/L toluene solution of each of the compounds (measurement target) was prepared and put in a quartz cell. An emission spectrum (ordinate axis: luminous intensity, abscissa axis: wavelength) of each of the samples was measured at a normal temperature (300K). In Examples, the emission spectrum was measured using a spectrophotometer manufactured by Hitachi, Ltd. (device name: F-7000). It should be noted that the luminescence spectrum measuring device may be different from the above device. A peak wavelength of the emission spectrum exhibiting the maximum luminous intensity was defined as a main peak wavelength.

The main peak wavelength of the compound D1 was 462 nm.

Manufacturing of Organic EL Device

Organic EL devices were manufactured and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick.

After the glass substrate having the transparent electrode line was cleaned, the glass substrate was mounted on a substrate holder of a vacuum evaporation apparatus. Initially, the compound HI was vapor-deposited on a surface of the glass substrate where the transparent electrode line was provided in a manner to cover the transparent electrode, thereby forming a 5-nm-thick hole injecting layer.

Next, the compound HT1 was vapor-deposited on the hole injecting layer to form an 80-nm-thick first hole transporting layer on the HI film.

Next, the compound HT2 was vapor-deposited on the first hole transporting layer to form a 10-nm-thick second hole transporting layer.

Further, a compound mCP was vapor-deposited on the second hole transporting layer to form a 5-nm-thick third hole transporting layer.

Further, the compound TADF1 (the first compound), the compound D1 (the fluorescent compound) and the compound H1 (the second compound) were co-deposited on the third hole transporting layer to form a 25-nm-thick emitting layer. A concentration of the compound TADF1 was defined as 12 mass %, a concentration of the compound D1 was defined as 1 mass %, and a concentration of the compound H1 was defined as 87 mass % in the emitting layer.

Next, a compound ET1 was vapor-deposited on the emitting layer to form a 5-nm-thick first electron transporting layer.

Next, a compound ET-2 was vapor-deposited on the first electron transporting layer to form a 20-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 1 is roughly shown as follows.

ITO(130)/HI(5)/HT1(80)/HT2(10)/mCP(5)/H1:TADF1: D1 (25, 87%:12%:1%)/ET1(5)/ET2(20)/LiF(1)/Al(80)

Numerals in parentheses represent a film thickness (unit: nm). The numerals represented by percentage in the same parentheses indicate a ratio (mass %) of the second compound, the first compound and the fluorescent compound in the emitting layer.

Example 2

An organic EL device in Example 2 was manufactured in the same manner as in Example 1 except that the concentration of the compound TADF1 was defined as 24 mass %, the concentration of the compound D1 was defined as 1 mass %, and the concentration of the compound H1 was defined as 75 mass % in the emitting layer.

A device arrangement of the organic EL device of Example 2 is roughly shown as follows.

ITO(130)/HI(5)/HT1(80)/HT2(10)/mCP(5)/H1:TADF1: D1 (25, 75%:24%:1%)/ET1(5)/ET2(20)/LiF(1)/Al(80)

Example 3

An organic EL device in Example 3 was manufactured in the same manner as in Example 1 except that the concentration of the compound TADF1 was defined as 50 mass %, the concentration of the compound D1 was defined as 1 mass %, and the concentration of the compound H1 was defined as 49 mass % in the emitting layer.

A device arrangement of the organic EL device of Example 3 is roughly shown as follows.

ITO(130)/HI(5)/HT1(80)/HT2(10)/mCP(5)/H1:TADF1:
D1 (25, 49%:50%:1%)/ET1(5)/ET2(20)/LiF(1)/Al(80)

Example 4

An organic EL device of Example 4 was manufactured in the same manner as in Example 2 except that the compound TADF2 was used in place of the compound TADF1 in the emitting layer of Example 2.

A device arrangement of the organic EL device of Example 4 is roughly shown as follows.
ITO(130)/HI(5)/HT1(80)/HT2(10)/mCP(5)/H1:TADF2:
D1 (25, 75%:24%:1%)/ET1(5)/ET2(20)/LiF(1)/Al(80)

Example 5

An organic EL device of Example 5 was manufactured in the same manner as in Example 3 except that the compound TADF2 was used in place of the compound TADF1 in the emitting layer of Example 3.

A device arrangement of the organic EL device of Example 5 is roughly shown as follows.
ITO(130)/HI(5)/HT1(80)/HT2(10)/mCP(5)/H1:TADF2:
D1 (25, 49%:50%:1%)/ET1(5)/ET2(20)/LiF(1)/Al(80)

Example 6

An organic EL device of Example 6 was manufactured in the same manner as in Example 2 except that the compound TADF3 was used in place of the compound TADF1 in the emitting layer of Example 2.

A device arrangement of the organic EL device of Example 6 is roughly shown as follows.
ITO(130)/HI(5)/HT1(80)/HT2(10)/mCP(5)/H1:TADF3:
D1 (25, 75%:24%:1%)/ET1(5)/ET2(20)/LiF(1)/Al(80)

Example 7

An organic EL device of Example 7 was manufactured in the same manner as in Example 3 except that the compound TADF3 was used in place of the compound TADF1 in the emitting layer of Example 3.

A device arrangement of the organic EL device of Example 7 is roughly shown as follows.
ITO(130)/HI(5)/HT1(80)/HT2(10)/mCP(5)/H1:TADF3:
D1 (25, 49%:50%:1%)/ET1(5)/ET2(20)/LiF(1)/Al(80)

Example 8

An organic EL device of Example 8 was manufactured in the same manner as in Example 2 except that the compound TADF4 was used in place of the compound TADF1 in the emitting layer of Example 2.

A device arrangement of the organic EL device of Example 8 is roughly shown as follows.
ITO(130)/HI(5)/HT1(80)/HT2(10)/mCP(5)/H1:TADF4:
D1 (25, 75%:24%:1%)/ET1(5)/ET2(20)/LiF(1)/Al(80)

Example 9

An organic EL device of Example 9 was manufactured in the same manner as in Example 3 except that the compound TADF4 was used in place of the compound TADF1 in the emitting layer of Example 3.

A device arrangement of the organic EL device of Example 9 is roughly shown as follows.
ITO(130)/HI(5)/HT1(80)/HT2(10)/mCP(5)/H1:TADF4:
D1 (25, 49%:50%:1%)/ET1(5)/ET2(20)/LiF(1)/Al(80)

Comparative 1

An organic EL device of Comparative 1 was manufactured in the same manner as in Example 2 except that the compound Ref-2 was used in place of the compound TADF1 in the emitting layer of Example 2.

A device arrangement of the organic EL device of Comparative 1 is roughly shown as follows.
ITO(130)/HI(5)/HT1(80)/HT2(10)/mCP(5)/H1:Ref-2:D1 (25, 75%:24%:1%)/ET1(5)/ET2(20)/LiF(1)/Al(80)

Comparative 2

An organic EL device of Comparative 2 was manufactured in the same manner as in Example 2 except that the compound Ref-3 was used in place of the compound TADF1 in the emitting layer of Example 2.

A device arrangement of the organic EL device of Comparative 2 is roughly shown as follows.
ITO(130)/HI(5)/HT1(80)/HT2(10)/mCP(5)/H1:Ref-3:D1 (25, 75%:24%:1%)/ET1(5)/ET2(20)/LiF(1)/Al(80)

Comparative 3

An organic EL device of Comparative 3 was manufactured in the same manner as in Example 2 except that the compound Ref-4 was used in place of the compound TADF1 in the emitting layer of Example 2.

A device arrangement of the organic EL device of Comparative 3 is roughly shown as follows.
ITO(130)/HI(5)/HT1(80)/HT2(10)/mCP(5)/H1:Ref-4:D1 (25, 75%:24%:1%)/ET1(5)/ET2(20)/LiF(1)/Al(80)

Evaluation of Organic EL Devices

The manufactured organic EL devices were evaluated as below. The evaluation results are shown in Table 1. The ratio (%) means mass % in Table 1.

External Quantum Efficiency EQE and Main Peak Wavelength $\lambda_p$

Voltage was applied on each of the organic EL devices such that a current density was 0.1 mA/cm$^2$, where spectral radiance spectra were measured by a spectroradiometer (CS-1000 manufactured by Konica Minolta, Inc.).

The external quantum efficiency EQE (unit: %) was calculated based on the obtained spectral-radiance spectra, assuming that the spectra were provided under a Lambertian radiation.

The main peak wavelength $\lambda_p$ (unit: nm) was calculated based on the obtained spectral-radiance spectra.

TABLE 1

| | First Compound | Ratio (%) | EQE (%) @0.1 mA/cm$^2$ | Main Peak Wavelength $\lambda_P$ (nm) |
|---|---|---|---|---|
| Example 1 | TADF1 | 12 | 11.1 | 463 |
| Example 2 | TADF1 | 24 | 14.0 | 464 |
| Example 3 | TADF1 | 50 | 14.3 | 465 |
| Example 4 | TADF2 | 24 | 11.4 | 463 |
| Example 5 | TADF2 | 50 | 12.1 | 465 |
| Example 6 | TADF3 | 24 | 8.3 | 463 |
| Example 7 | TADF3 | 50 | 10.2 | 464 |
| Example 8 | TADF4 | 24 | 12.5 | 463 |
| Example 9 | TADF4 | 50 | 11.9 | 464 |
| Comp. 1 | Ref-2 | 24 | 7.8 | 463 |

TABLE 1-continued

| | First Compound | Ratio (%) | EQE (%) @0.1 mA/cm$^2$ | Main Peak Wavelength $\lambda_P$ (nm) |
|---|---|---|---|---|
| Comp. 2 | Ref-3 | 24 | 7.6 | 463 |
| Comp. 3 | Ref-4 | 24 | 7.6 | 464 |

The organic EL devices of Examples 1 to 9, in each of which the emitting layer contained the first compound represented by the formula (1) and the fluorescent compound, exhibited a higher luminous efficiency than the organic EL device of Comparatives 1 to 3.

Example 10

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick.

After the glass substrate having the transparent electrode line was cleaned, the glass substrate was mounted on a substrate holder of a vacuum evaporation apparatus. Initially, the compound HI was vapor-deposited on a surface of the glass substrate where the transparent electrode line was provided in a manner to cover the transparent electrode, thereby forming a 5-nm-thick hole injecting layer.

Next, the compound HT1 was vapor-deposited on the hole injecting layer to form an 80-nm-thick first hole transporting layer on the HI film.

Next, the compound HT2 was vapor-deposited on the first hole transporting layer to form a 10-nm-thick second hole transporting layer.

Further, a compound mCP was vapor-deposited on the second hole transporting layer to form a 5-nm-thick third hole transporting layer.

Next, on the third hole transporting layer, the compound TADF1 (the first compound) and the compound H1 (the second compound) were co-deposited to form a 25-nm-thick emitting layer. The concentration of the compound TADF1 in the emitting layer was set at 12 mass % and the concentration of the compound H1 in the emitting layer was set at 88 mass %.

Next, a compound ET1 was vapor-deposited on the emitting layer to form a 5-nm-thick first electron transporting layer.

Next, a compound ET-2 was vapor-deposited on the first electron transporting layer to form a 20-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 10 is roughly shown as follows.
ITO(130)/HI(5)/HT1(80)/HT2(10)/mCP(5)/H1:TADF1 (25, 88%:12%)/ET1(5)/ET2(20)/LiF(1)/Al(80)

Numerals in parentheses represent a film thickness (unit: nm). The numerals represented by percentage in the same parentheses indicate a ratio (mass %) of the second compound and the first compound in the emitting layer.

Example 11

An organic EL device in Example 11 was manufactured in the same manner as in Example 10 except that the concentration of the compound TADF1 was defined as 24 mass %, and the concentration of the compound H1 was defined as 76 mass % in the emitting layer.

A device arrangement of the organic EL device of Example 11 is roughly shown as follows.
ITO(130)/HI(5)/HT1(80)/HT2(10)/mCP(5)/H1:TADF1 (25, 76%:24%)/ET1(5)/ET2(20)/LiF(1)/Al(80)

Example 12

An organic EL device of Example 12 was manufactured in the same manner as in Example 11 except that the compound TADF2 was used in place of the compound TADF1 in the emitting layer of Example 11.

A device arrangement of the organic EL device of Example 12 is roughly shown as follows.
ITO(130)/HI(5)/HT1(80)/HT2(10)/mCP(5)/H1:TADF2 (25, 76%:24%)/ET1(5)/ET2(20)/LiF(1)/Al(80)

Example 13

An organic EL device of Example 13 was manufactured in the same manner as in Example 11 except that the compound TADF4 was used in place of the compound TADF1 in the emitting layer of Example 11.

A device arrangement of the organic EL device of Example 13 is roughly shown as follows.
ITO(130)/HI(5)/HT1(80)/HT2(10)/mCP(5)/H1:TADF4 (25, 76%:24%)/ET1(5)/ET2(20)/LiF(1)/Al(80)

Comparative 4

An organic EL device of Comparative 4 was manufactured in the same manner as in Example 11 except that the compound Ref-1 was used in place of the compound TADF1 in the emitting layer of Example 11.

A device arrangement of the organic EL device of Comparative 4 is roughly shown as follows.
ITO(130)/HI(5)/HT1(80)/HT2(10)/mCP(5)/H1:ref-1 (25, 76%:24%)/ET1(5)/ET2(20)/LiF(1)/Al(80)

Comparative 5

An organic EL device of Comparative 5 was manufactured in the same manner as in Example 11 except that the compound Ref-2 was used in place of the compound TADF1 in the emitting layer of Example 11.

A device arrangement of the organic EL device of Comparative 5 is roughly shown as follows.
ITO(130)/HI(5)/HT1(80)/HT2(10)/mCP(5)/H1:ref-2 (25, 76%:24%)/ET1(5)/ET2(20)/LiF(1)/Al(80)

Comparative 6

An organic EL device of Comparative 6 was manufactured in the same manner as in Example 11 except that the compound Ref-3 was used in place of the compound TADF1 in the emitting layer of Example 11.

A device arrangement of the organic EL device of Comparative 6 is roughly shown as follows.
ITO(130)/HI(5)/HT1(80)/HT2(10)/mCP(5)/H1:ref-3 (25, 76%:24%)/ET1(5)/ET2(20)/LiF(1)/Al(80)

Comparative 7

An organic EL device of Comparative 7 was manufactured in the same manner as in Example 11 except that the compound Ref-4 was used in place of the compound TADF1 in the emitting layer of Example 11.

A device arrangement of the organic EL device of Comparative 7 is roughly shown as follows.

ITO(130)/HI(5)/HT1(80)/HT2(10)/mCP(5)/H1:ref-4 (25, 76%:24%)/ET1(5)/ET2(20)/LiF(1)/Al(80)

Comparative 8

An organic EL device of Comparative 8 was manufactured in the same manner as in Example 11 except that the compound Ref-5 was used in place of the compound TADF1 in the emitting layer of Example 11.

A device arrangement of the organic EL device of Comparative 8 is roughly shown as follows.

ITO(130)/HI(5)/HT1(80)/HT2(10)/mCP(5)/H1:ref-5 (25, 76%:24%)/ET1(5)/ET2(20)/LiF(1)/Al(80)

Comparative 9

An organic EL device of Comparative 9 was manufactured in the same manner as in Example 11 except that the compound Ref-6 was used in place of the compound TADF1 in the emitting layer of Example 11.

A device arrangement of the organic EL device of Comparative 9 is roughly shown as follows.

ITO(130)/HI(5)/HT1(80)/HT2(10)/mCP(5)/H1:ref-6 (25, 76%:24%)/ET1(5)/ET2(20)/LiF(1)/Al(80)

Evaluation of Organic EL Devices

The manufactured organic EL devices were evaluated in terms of the external quantum efficiency EQE and main peak wavelength λp by the same method described above. The evaluation results are shown in Table 2. The ratio (%) means mass % in Table 2.

TABLE 2

| | First Compound | Ratio (%) | EQE (%) @0.1 mA/cm² | Main Peak Wavelength $\lambda_P$ (nm) |
|---|---|---|---|---|
| Example 10 | TADF1 | 12 | 15.2 | 473 |
| Example 11 | TADF1 | 24 | 15.8 | 480 |
| Example 12 | TADF2 | 24 | 9.8 | 467 |
| Example 13 | TADF4 | 24 | 8.7 | 468 |
| Comp. 4 | Ref-1 | 24 | 6.6 | 472 |
| Comp. 5 | Ref-2 | 24 | 1.7 | 440 |
| Comp. 6 | Ref-3 | 24 | 3.7 | 440 |
| Comp. 7 | Ref-4 | 24 | 1.2 | 445 |
| Comp. 8 | Ref-5 | 24 | 1.8 | 458 |
| Comp. 9 | Ref-6 | 24 | <1.0 | unmeasurable |

The organic EL devices of Examples 10 to 13, in each of which the emitting layer contained the first compound represented by the formula (1) and the second compound having a larger singlet energy $S_1(M2)$ than the singlet energy $S_1(M1)$ of the first compound, exhibited a higher luminous efficiency than the organic EL device of Comparatives 4 to 9.

EXPLANATION OF CODES

1 . . . organic EL device, 2 . . . substrate, 3 . . . anode, 4 . . . cathode, 5 . . . emitting layer, 6 . . . hole injecting layer, 7 . . . hole transporting layer, 8 . . . electron transporting layer, 9 . . . electron injecting layer.

The invention claimed is:

1. An organic electroluminescence device, comprising:
an anode;
an emitting layer; and
a cathode, wherein
the emitting layer comprises a first compound and a fluorescent compound,
a singlet energy $S_1(M1)$ of the first compound is larger than a singlet energy $S_1(FL)$ of the fluorescent compound, and
the first compound is represented by a formula (1):

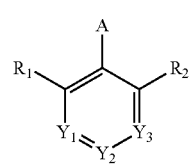

(1)

wherein $Y_1$, $Y_2$ and $Y_3$ each independently represent C—Ra or a nitrogen atom;
at least one of $Y_1$, $Y_2$ and $Y_3$ is a nitrogen atom;
$R_1$, $R_2$ and Ra each independently represent a hydrogen atom or a substituent;
$R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom;
a plurality of Ra are mutually the same or different;
at least one of $R_1$ and $R_2$ is the substituent; and
A is a group represented by one of a formula (1b) and a formula (1c):

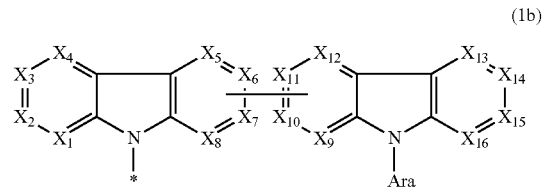

(1b)

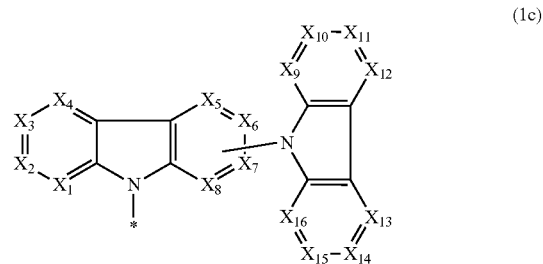

(1c)

wherein, in the formulae (1b) and (1c), $X_1$ to $X_{16}$ each independently represent C—Rb or a nitrogen atom;

in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$;

in the formula (1c), at least one of $X_5$ to $X_8$ is a carbon atom bonded to a nitrogen atom in a five-membered ring of a nitrogen-containing fused ring including $X_9$ to $X_{16}$;

Rb each independently represents a hydrogen atom or a substituent, Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom;

a plurality of Rb are mutually the same or different;

when a plurality of ones of $X_1$ to $X_8$ are C—Rb and Rb is a substituent, a plurality of Rb are bonded to each other to form a ring, or are not bonded;

when a plurality of ones of $X_9$ to $X_{16}$ are C—Rb and Rb is a substituent, a plurality of Rb are bonded to each other to form a ring, or are not bonded;

Ara is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group; and

* represents a bonding position with a carbon atom in a cyclic structure of the first compound.

2. The organic electroluminescence device according to claim 1, wherein
the emitting layer further comprises a second compound, and
a singlet energy $S_1(M2)$ of the second compound is larger than the singlet energy $S_1(M1)$ of the first compound.

3. The organic electroluminescence device according to claim 1, wherein
the first compound is a thermally activated delayed fluorescent compound.

4. The organic electroluminescence device according to claim 1, wherein
the first compound is represented by a formula (11):

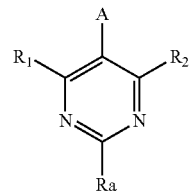

(11)

wherein Ra represents a hydrogen atom or a substituent;
$R_1$ and $R_2$ are each independently a substituent;
$R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and
A is the group represented by one of the formula (1b) and the formula (1c).

5. The organic electroluminescence device according to claim 1, wherein
the first compound is represented by a formula (13) or a formula (14):

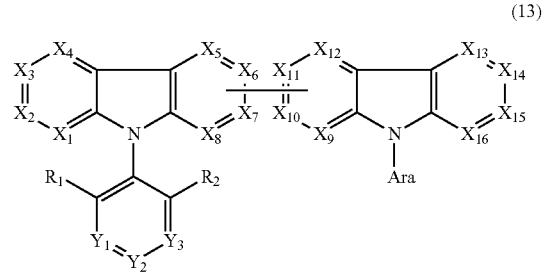

(13)

wherein $Y_1$, $Y_2$ and $Y_3$ each independently represent C—Ra or a nitrogen atom;
at least one of $Y_1$, $Y_2$ and $Y_3$ is a nitrogen atom;
$R_1$, $R_2$ and Ra each independently represent a hydrogen atom or a substituent;
$R_1$, $R_2$ and Ra as the substituents each independently represent the same as the above-described $R_1$, $R_2$ and Ra as the substituents;
a plurality of Ra are mutually the same or different;
at least one of $R_1$ and $R_2$ is the substituent;

$X_1$ to $X_{16}$ each independently represent C—Rb or a nitrogen atom;

at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$;

Rb each independently represents a hydrogen atom or a substituent;

Rb as the substituent represents the same as the above-described Rb as the substituent;

a plurality of Rb are mutually the same or different;

when a plurality of ones of $X_1$ to $X_8$ are C—Rb and Rb is a substituent, a plurality of Rb are bonded to each other to form a ring, or are not bonded;

when a plurality of ones of $X_9$ to $X_{16}$ are C—Rb and Rb is a substituent, a plurality of Rb are bonded to each other to form a ring, or are not bonded; and Ara represents the same as the above-described Ara as the substituent,

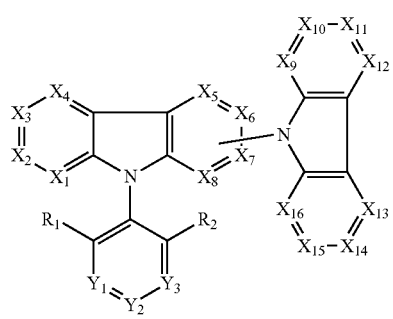

(14)

wherein $Y_1$, $Y_2$ and $Y_3$ each independently represent C—Ra or a nitrogen atom;

at least one of $Y_1$, $Y_2$ and $Y_3$ is a nitrogen atom;

$R_1$, $R_2$ and Ra each independently represent a hydrogen atom or a substituent;

$R_1$, $R_2$ and Ra as the substituents each independently represent the same as the above-described $R_1$, $R_2$ and Ra as the substituents;

a plurality of Ra are mutually the same or different;

at least one of $R_1$ and $R_2$ is the substituent;

$X_1$ to $X_{16}$ each independently represent C—Rb or a nitrogen atom;

at least one of $X_5$ to $X_8$ is a carbon atom bonded to a nitrogen atom in a five-membered ring of a nitrogen-containing fused ring including $X_9$ to $X_{16}$;

Rb each independently represents a hydrogen atom or a substituent;

Rb as the substituent represents the same as the above-described Rb as the substituent;

a plurality of Rb are mutually the same or different;

when a plurality of ones of $X_1$ to $X_8$ are C—Rb and Rb is a substituent, a plurality of Rb are bonded to each other to form a ring, or are not bonded; and when a plurality of ones of $X_9$ to $X_{16}$ are C—Rb and Rb is a substituent, a plurality of Rb are bonded to each other to form a ring, or are not bonded.

6. The organic electroluminescence device according to claim 5, wherein
the first compound is represented by the formula (13).

7. The organic electroluminescence device according to claim 5, wherein
the first compound is represented by a formula (13b) or a formula (14a):

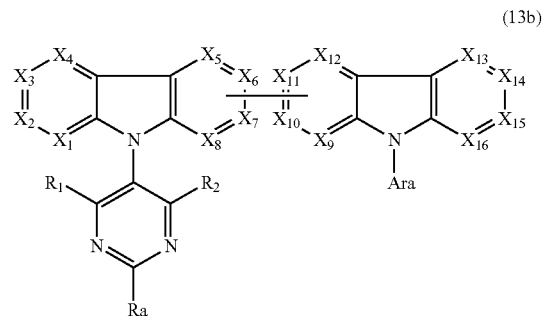

(13b)

wherein $R_1$, $R_2$ and Ra each independently represent a hydrogen atom or a substituent;

$R_1$, $R_2$ and Ra as the substituents each independently represent the same as the above-described $R_1$, $R_2$ and Ra as the substituents;

at least one of $R_1$ and $R_2$ is the substituent;

$X_1$ to $X_{16}$ each independently represent C—Rb or a nitrogen atom;

at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$;

Rb each independently represents a hydrogen atom or a substituent;

Rb as the substituent represents the same as the above-described Rb as the substituent;

a plurality of Rb are mutually the same or different;

when a plurality of ones of $X_1$ to $X_8$ are C—Rb and Rb is a substituent, a plurality of Rb are bonded to each other to form a ring, or are not bonded;

when a plurality of ones of $X_9$ to $X_{16}$ are C—Rb and Rb is a substituent, a plurality of Rb are bonded to each other to form a ring, or are not bonded; and Ara represents the same as the above-described Ara as the substituent,

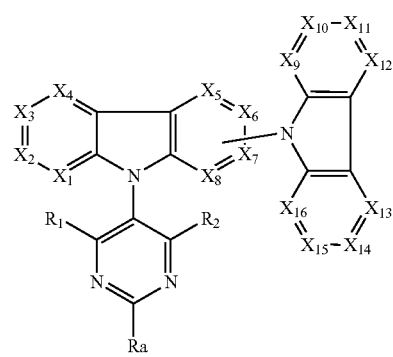

(14a)

wherein $R_1$, $R_2$ and Ra each independently represent a hydrogen atom or a substituent;

$R_1$, $R_2$ and Ra as the substituents each independently represent the same as the above-described $R_1$, $R_2$ and Ra as the substituents;

at least one of $R_1$ and $R_2$ is the substituent;

$X_1$ to $X_{16}$ each independently represent C—Rb or a nitrogen atom;

at least one of $X_5$ to $X_8$ is a carbon atom bonded to a nitrogen atom in a five-membered ring of a nitrogen-containing fused ring including $X_9$ to $X_{16}$;

Rb each independently represents a hydrogen atom or a substituent;

Rb as the substituent represents the same as the above-described Rb as the substituent;

a plurality of Rb are mutually the same or different;

when a plurality of ones of $X_1$ to $X_8$ are C—Rb and Rb is a substituent, a plurality of Rb are bonded to each other to form a ring, or are not bonded; and when a plurality of ones of $X_9$ to $X_{16}$ are C—Rb and Rb is a substituent, a plurality of Rb are bonded to each other to form a ring, or are not bonded.

8. The organic electroluminescence device according to claim 1, wherein

A is the group represented by the formula (1b), and when Rb is a hydrogen atom or a substituent, Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

9. The organic electroluminescence device according to claim 1, wherein

A is the group represented by the formula (1b), and $X_1$, $X_2$, $X_3$, and $X_4$ are C—Rb in which Rb is a hydrogen atom.

10. The organic electroluminescence device according to claim 1, wherein $X_1$ to $X_{16}$ are C—Rb, a plurality of Rb are mutually the same or different, in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$, and in the formula (1c), at least one of $X_5$ to $X_8$ is a carbon atom bonded to a nitrogen atom in a five-membered ring of a nitrogen-containing fused ring including $X_9$ to $X_{16}$.

11. The organic electroluminescence device according to claim 1, wherein $X_1$ to $X_{16}$ are C—Rb, Rb each independently represents a hydrogen atom or a substituent, Rb as the substituent is selected from the group consisting of a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms, a plurality of Rb are mutually the same or different, in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$, and in the formula (1c), at least one of $X_5$ to $X_8$ is a carbon atom bonded to a nitrogen atom in a five-membered ring of a nitrogen-containing fused ring including $X_9$ to $X_{16}$.

12. The organic electroluminescence device according to claim 1, wherein $X_1$ to $X_{16}$ are C—Rb, Rb each independently represents a hydrogen atom or a substituent, Rb as the substituent is selected from the group consisting of a substituted or unsubstituted aryl group having 6 to 30 ring carbon atoms, a plurality of Rb are mutually the same or different, in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$, and in the formula (1c), at least one of $X_5$ to $X_8$ is a carbon atom bonded to a nitrogen atom in a five-membered ring of a nitrogen-containing fused ring including $X_9$ to $X_{16}$.

13. The organic electroluminescence device according to claim 1, wherein $X_1$ to $X_{16}$ are C—Rb, Rb is a hydrogen atom, in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$, and in the formula (1c), at least one of $X_5$ to $X_8$ is a carbon atom bonded to a nitrogen atom in a five-membered ring of a nitrogen-containing fused ring including $X_9$ to $X_{16}$.

14. The organic electroluminescence device according to claim 1, wherein

Ra is a substituent,

Ra as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom, and a plurality of Ra are mutually the same or different.

15. The organic electroluminescence device according to claim 1, wherein $R_1$, $R_2$ and Ra are each independently a substituted or unsubstituted aryl group having 6 to 30 ring carbon atoms.

16. The organic electroluminescence device according to claim 1, wherein $R_1$, $R_2$ and Ra are each independently a substituted or unsubstituted phenyl group.

17. The organic electroluminescence device according to claim 1, further comprising:
a hole transporting layer between the anode and the emitting layer.

18. The organic electroluminescence device according to claim 1, further comprising:
an electron transporting layer between the cathode and the emitting layer.

19. An electronic device comprising the organic electroluminescence device according to claim 1.

20. An organic electroluminescence device, comprising:
an anode;
an emitting layer; and
a cathode, wherein
the emitting layer comprises a first compound and a second compound,
a singlet energy $S_1(M2)$ of the second compound is larger than a singlet energy $S_1(M1)$ of the first compound, and
the first compound is represented by a formula (1):

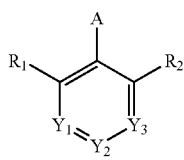

(1)

wherein $Y_1$, $Y_2$ and $Y_3$ each independently represent C—Ra or a nitrogen atom;
at least one of $Y_1$, $Y_2$ and $Y_3$ is a nitrogen atom;
$R_1$, $R_2$ and Ra each independently represent a hydrogen atom or a substituent;
$R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, and a carboxy group, and a halogen atom;
a plurality of Ra are mutually the same or different;
at least one of $R_1$ and $R_2$ is the substituent; and
A is a group represented by one of a formula (1b) and a formula (1c):

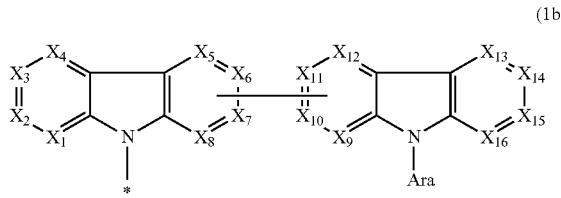

(1b)

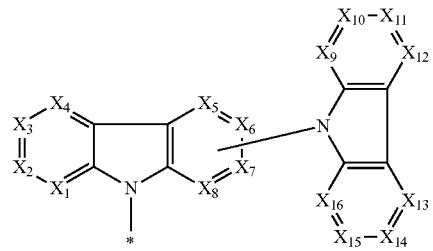

(1c)

wherein in the formulae (1b) and (1c), $X_1$ to $X_{16}$ each independently represent C—Rb or a nitrogen atom, and
in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$,
in the formula (1c), at least one of $X_5$ to $X_8$ is a carbon atom bonded to a nitrogen atom in a five-membered ring of a nitrogen-containing fused ring including $X_9$ to $X_{16}$,
Rb each independently represents a hydrogen atom or a substituent, Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, and a carboxy group, and a halogen atom;
a plurality of Rb are mutually the same or different;
when a plurality of ones of $X_1$ to $X_8$ are C—Rb and Rb is a substituent, a plurality of Rb are bonded to each other to form a ring, or are not bonded;
when a plurality of ones of $X_9$ to $X_{16}$ are C—Rb and Rb is a substituent, a plurality of Rb are bonded to each other to form a ring, or are not bonded;
Ara is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group; and
* represents a bonding position with a carbon atom in a cyclic structure of the first compound.

21. The organic electroluminescence device according to claim 20, wherein the first compound is a thermally activated delayed fluorescent compound.

22. An electronic device, comprising the organic electroluminescence device according to claim 20.

23. A compound, represented by a formula (11):

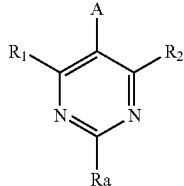

(11)

wherein Ra represents a hydrogen atom or a substituent;
$R_1$ and $R_2$ are each independently a substituent;
$R_1$, $R_2$ and Ra as the substituents are each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and A is a group represented by one of a formula (1b) and a formula (1c):

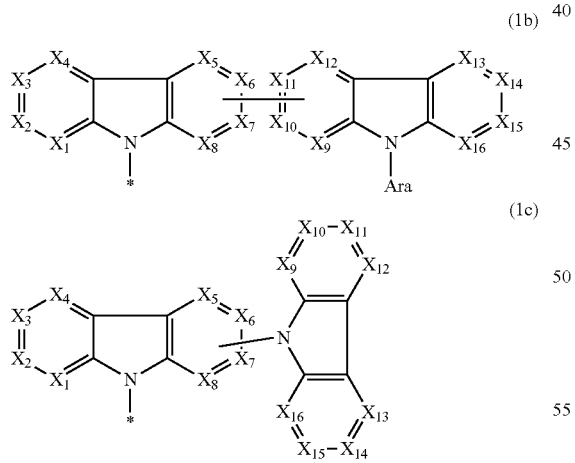

(1b)

(1c)

wherein, in the formulae (1b) and (1c), —$X_1$ to $X_{16}$ each independently represent C—Rb or a nitrogen atom;
in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$;
in the formula (1c), at least one of $X_5$ to $X_8$ is a carbon atom bonded to a nitrogen atom in a five-membered ring of a nitrogen-containing fused ring including $X_9$ to $X_{16}$;

Rb each independently represents a hydrogen atom or a substituent;
Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom;
a plurality of Rb are mutually the same or different;
when a plurality of ones of $X_1$ to $X_8$ are C—Rb and Rb is a substituent, a plurality of Rb are bonded to each other to form a ring, or are not bonded;
when a plurality of ones of $X_9$ to $X_{16}$ are C—Rb and Rb is a substituent, a plurality of Rb are bonded to each other to form a ring, or are not bonded;
Ara is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group; and
* represents a bonding position with a carbon atom in a cyclic structure of the compound represented by the formula (11).

24. The compound according to claim 23, wherein the compound is represented by a formula (13bx) or a formula (14ax):

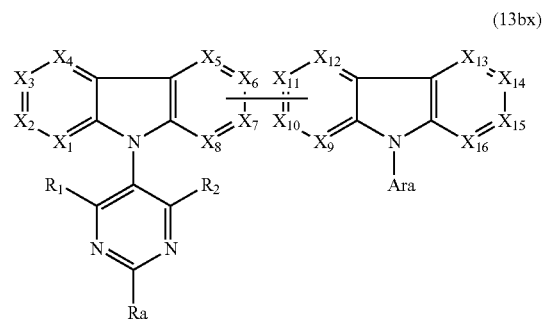

(13bx)

wherein $R_1$ and $R_2$ are each independently a substituent;
Ra represents a hydrogen atom or a substituent;
$R_1$, $R_2$ and Ra as the substituents each independently represent the same as the above-described $R_1$, $R_2$ and Ra as the substituents;
at least one of $R_1$ and $R_2$ is the substituent;

$X_1$ to $X_{16}$ each independently represent C—Rb or a nitrogen atom;

at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$;

Rb each independently represents a hydrogen atom or a substituent;

Rb as the substituent represents the same as the above-described Rb as the substituent;

a plurality of Rb are mutually the same or different;

when a plurality of ones of $X_1$ to $X_8$ are C—Rb and Rb is a substituent, a plurality of Rb are bonded to each other to form a ring, or are not bonded;

when a plurality of ones of $X_9$ to $X_{16}$ are C—Rb and Rb is a substituent, a plurality of Rb are bonded to each other to form a ring, or are not bonded; and Ara represents the same as the above-described Ara as the substituent,

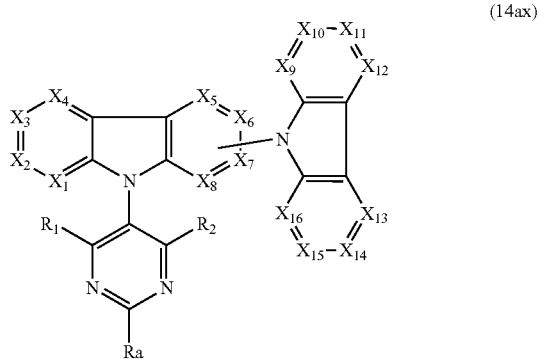

(14ax)

wherein $R_1$ and $R_2$ are each independently a substituent;

Ra represents a hydrogen atom or a substituent;

$R_1$, $R_2$ and Ra as the substituents each independently represent the same as the above-described $R_1$, $R_2$ and Ra as the substituents;

at least one of $R_1$ and $R_2$ is the substituent;

$X_1$ to $X_{16}$ each independently represent C—Rb or a nitrogen atom;

at least one of $X_5$ to $X_8$ is a carbon atom bonded to a nitrogen atom in a five-membered ring of a nitrogen-containing fused ring including $X_9$ to $X_{16}$;

Rb each independently represents a hydrogen atom or a substituent;

Rb as the substituent represents the same as the above-described Rb as the substituent;

a plurality of Rb are mutually the same or different;

when a plurality of ones of $X_1$ to $X_8$ are C—Rb and Rb is a substituent, a plurality of Rb are bonded to each other to form a ring, or are not bonded; and when a plurality of ones of $X_9$ to $X_{16}$ are C—Rb and Rb is a substituent, a plurality of Rb are bonded to each other to form a ring, or are not bonded.

25. The compound according to claim 24, wherein the compound is represented by the formula (13bx).

26. The compound according to claim 23, wherein:

A is the group represented by the formula (1b); at least one of $X_1$ to $X_4$ is C—Rb; and when Rb is a hydrogen atom or a substituent, Rb as the substituent is selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom.

27. The compound according to claim 23, wherein A is the group represented by the formula (1b), and $X_1$, $X_2$, $X_3$, and $X_4$ are C—Rb in which Rb is a hydrogen atom.

28. The compound according to claim 23, wherein:

$X_1$ to $X_{16}$ are C—Rb;

a plurality of Rb are mutually the same or different;

in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$; and in the formula (1c), at least one of $X_5$ to $X_8$ is a carbon atom bonded to a nitrogen atom in a five-membered ring of a nitrogen-containing fused ring including $X_9$ to $X_{16}$.

29. The compound according to claim 23, wherein:

$X_1$ to $X_{16}$ are C—Rb;

Rb each independently represents a hydrogen atom or a substituent;

Rb as the substituent is selected from the group consisting of a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms;

a plurality of Rb are mutually the same or different;

in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$; and in the formula (1c), at least one of $X_5$ to $X_8$ is a carbon atom bonded to a nitrogen atom in a five-membered ring of a nitrogen-containing fused ring including $X_9$ to $X_{16}$.

30. The compound according to claim 23, wherein:

$X_1$ to $X_{16}$ are C—Rb;

Rb each independently represents a hydrogen atom or a substituent;

Rb as the substituent is selected from the group consisting of a substituted or unsubstituted aryl group having 6 to 30 ring carbon atoms;

a plurality of Rb are mutually the same or different;

in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$; and in the formula (1c), at least one of $X_5$ to $X_8$ is a carbon atom bonded to a nitrogen atom in a five-membered ring of a nitrogen-containing fused ring including $X_9$ to $X_{16}$.

31. The compound according to claim 23, wherein:
$X_1$ to $X_{16}$ are C—Rb;
Rb is a hydrogen atom; in the formula (1b), at least one of $X_5$ to $X_8$ is a carbon atom bonded to one of $X_9$ to $X_{12}$ while at least one of $X_9$ to $X_{12}$ is a carbon atom bonded to one of $X_5$ to $X_8$; and
in the formula (1c), at least one of $X_5$ to $X_8$ is a carbon atom bonded to a nitrogen atom in a five-membered ring of a nitrogen-containing fused ring including $X_9$ to $X_{16}$.

32. The compound according to claim 23, wherein:
Ra is a substituent;
Ra as the substituent is each independently selected from the group consisting of a substituted or unsubstituted alkyl group having 1 to 30 carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heteroaryl group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, and a halogen atom; and
a plurality of Ra are mutually the same or different.

33. The compound according to claim 23, wherein $R_1$, $R_2$ and Ra are each independently a substituted or unsubstituted aryl group having 6 to 30 ring carbon atoms.

34. The compound according to claim 23, wherein $R_1$, $R_2$ and Ra are each independently a substituted or unsubstituted phenyl group.

* * * * *